United States Patent
Rosser

(10) Patent No.: US 11,292,832 B2
(45) Date of Patent: Apr. 5, 2022

(54) COMPOSITIONS AND METHODS FOR TREATMENT OF DISEASES INVOLVING CXCL1 FUNCTION

(71) Applicant: Charles J. Rosser, Stevenson Ranch, CA (US)

(72) Inventor: Charles J. Rosser, Stevenson Ranch, CA (US)

( * ) Notice: Subject to any disclaimer, the term of this patent is extended or adjusted under 35 U.S.C. 154(b) by 0 days.

(21) Appl. No.: 16/982,456

(22) PCT Filed: Jan. 28, 2020

(86) PCT No.: PCT/US2020/015457
§ 371 (c)(1),
(2) Date: Sep. 18, 2020

(87) PCT Pub. No.: WO2020/160022
PCT Pub. Date: Aug. 6, 2020

(65) Prior Publication Data
US 2021/0301007 A1   Sep. 30, 2021

Related U.S. Application Data

(60) Provisional application No. 62/797,573, filed on Jan. 28, 2019.

(51) Int. Cl.
| | | |
|---|---|---|
| *C07K 16/24* | (2006.01) | |
| *A61P 35/00* | (2006.01) | |
| *A61K 45/06* | (2006.01) | |
| *A61K 39/00* | (2006.01) | |

(52) U.S. Cl.
CPC .............. *C07K 16/24* (2013.01); *A61K 45/06* (2013.01); *A61P 35/00* (2018.01); *A61K 2039/505* (2013.01)

(58) Field of Classification Search
None
See application file for complete search history.

(56) References Cited

U.S. PATENT DOCUMENTS

| | | |
|---|---|---|
| 9,309,312 B2 | 4/2016 | Kanamori et al. |
| 2011/0171213 A1 | 7/2011 | Houhou et al. |
| 2011/0263436 A1 | 10/2011 | Tu et al. |
| 2016/0108117 A1 | 4/2016 | Pages et al. |
| 2016/0152699 A1 | 6/2016 | Beidler et al. |

OTHER PUBLICATIONS

Miyake et al (Theranostics, Jan. 25, 2019, 9:853-867).*
Bandapalli et al (Cytokine, 2012, 57:46-53).*
International Search Report for Application No. PCT/US2020/15457 dated Jun. 10, 2020.
Miyake, Makito, et al., "Monoclonal antibody against CXCL1 (HL2401) as a novel agent in suppressing IL6 expression and tumoral growth," Theranostics, (2019), vol. 9, No. 3: 853-867.

* cited by examiner

*Primary Examiner* — Laura B Goddard
(74) *Attorney, Agent, or Firm* — McBee Moore Woodward & Vanik IP, LLC

(57) ABSTRACT

The present disclosure relates to antibodies, for example monoclonal antibodies, and their use in clinical patient evaluation and therapy. The present disclosure further relates to a method for modulating the activity of human CXCL-1 protein (hereinafter, referred to as CXCL1). In an aspect, antibodies described herein are capable of being used as a medicament for the prevention and/or treatment of diseases involving CXCL1 function, for example, pathological angiogenesis and inflammatory diseases.

19 Claims, 33 Drawing Sheets
(17 of 33 Drawing Sheet(s) Filed in Color)
Specification includes a Sequence Listing.

Numbering & Regions

| Variable light chain | D | I | V | L | T | Q | S | P | A | S | L | A | V | S | L | G | Q | R | A |
|---|---|---|---|---|---|---|---|---|---|---|---|---|---|---|---|---|---|---|---|
| Chothia numbering | L1 | L2 | L3 | L4 | L5 | L6 | L7 | L8 | L9 | L10 | L11 | L12 | L13 | L14 | L15 | L16 | L17 | L18 | L19 |

CHOTHIA REGIONS: LFR1

| S | G | K | A | S | Q | S | V | D | Y | D | G | D | S | Y | W | Y | Q |
|---|---|---|---|---|---|---|---|---|---|---|---|---|---|---|---|---|---|
| L22 | L23 | L24 | L25 | L26 | L27 | L28 | L29 | L30 | L30A | L30B | L30C | L30D | L31 | L32 | L33 | L34 | L35 | L36 | L37 | L38 |

CDR-L1 / LFR2

| P | G | Q | P | P | K | L | L | I | Y | A | A | S | N | L | E | S | R | A |
|---|---|---|---|---|---|---|---|---|---|---|---|---|---|---|---|---|---|---|
| L40 | L41 | L42 | L43 | L44 | L45 | L46 | L47 | L48 | L49 | L50 | L51 | L52 | L53 | L54 | L55 | L56 | L57 | L58 | L59 | L60 | L61 |

CDR-L2 / LFR3

| S | G | S | G | T | D | F | T | L | N | I | L | P | V | E | D | D | G | A | T |
|---|---|---|---|---|---|---|---|---|---|---|---|---|---|---|---|---|---|---|---|
| L63 | L64 | L65 | L66 | L67 | L68 | L69 | L70 | L71 | L72 | L73 | L74 | L75 | L76 | L77 | L78 | L79 | L80 | L81 | L82 | L83 | L84 | L85 |

| Y | Y | C | Q | Q | S | E | D | P | W | T | F | G | G | G | T | K | L | E | I | K |
|---|---|---|---|---|---|---|---|---|---|---|---|---|---|---|---|---|---|---|---|---|
| L86 | L87 | L88 | L89 | L90 | L91 | L92 | L93 | L94 | L95 | L96 | L97 | L98 | L99 | L100 | L101 | L102 | L103 | L104 | L105 | L106 | L107 |

CDR-L3 / LFR4

FIG. 1F

Numbering & Regions

| Variable Heavy chain | E | V | K | L | V | E | S | G | A | E | L | V | K | P | G | A | S | V | K | L |
|---|---|---|---|---|---|---|---|---|---|---|---|---|---|---|---|---|---|---|---|---|
| Chothia numbering | H1 | H2 | H3 | H4 | H5 | H6 | H7 | H8 | H9 | H10 | H11 | H12 | H13 | H14 | H15 | H16 | H17 | H18 | H19 | H20 |

CHOTHIA REGIONS — HFR1

| S | C | K | A | S | G | Y | T | F | T | S | Y | Y | I | W | V | K | Q | P | Q |
|---|---|---|---|---|---|---|---|---|---|---|---|---|---|---|---|---|---|---|---|
| H21 | H22 | H23 | H24 | H25 | H26 | H27 | H28 | H29 | H30 | H31 | H32 | H33 | H34 | H35 | H36 | H37 | H38 | H39 | H40 |

CDR-H1 — HFR2

| P | G | Q | G | L | E | W | I | G | E | I | D | P | S | H | G | P | T | F | N | E | K | F | K | N |
|---|---|---|---|---|---|---|---|---|---|---|---|---|---|---|---|---|---|---|---|---|---|---|---|---|
| H41 | H42 | H43 | H44 | H45 | H46 | H47 | H48 | H49 | H50 | H51 | H52 | H52A | H53 | H54 | H55 | H56 | H57 | H58 | H59 | H60 | H61 | H62 | H63 | H64 | H65 |

CDR-H2 — HFR3

| K | A | T | L | T | V | D | K | S | S | S | T | A | Y | M | Q | L | S | S | L | T | S | D |
|---|---|---|---|---|---|---|---|---|---|---|---|---|---|---|---|---|---|---|---|---|---|---|
| H66 | H67 | H68 | H69 | H70 | H71 | H72 | H73 | H74 | H75 | H76 | H77 | H78 | H79 | H80 | H81 | H82 | H82A | H82B | H82C | H83 | H84 | H85 |

| D | S | A | V | Y | Y | C | T | R | E | S | G | T | G | A | M | D | Y | W | G | Q | G | T |
|---|---|---|---|---|---|---|---|---|---|---|---|---|---|---|---|---|---|---|---|---|---|---|
| H86 | H87 | H88 | H89 | H90 | H91 | H92 | H93 | H94 | H95 | H96 | H97 | H98 | H99 | H100 | H100A | H101 | H102 | H103 | H104 | H105 | H106 | H107 |

CDR-H3 — HFR4

| T | L | T | V | S | S |
|---|---|---|---|---|---|
| H108 | H109 | H110 | H111 | H112 | H113 |

FIG. 1G

```
Hum2401    QVQLVESGGGLVQPGGSLRLSCAASGYTFTSYYIHWVRQAPGKGLEWIGEIDPSHGQTE
HumBB2401  QVQLVQSGAEVKKPGASVRLSCAASGYTFTSYYIHWVRQAPGQGLEWIGEIDPSHGQTE
           *****: **.::.::**.:***:*************************************

Hum2401    NEKFKNRFTISRDNSKNTLYLQMNSLRAEDTAVYYCTRESGTGMDYWGQGTLVTVSSGG
HumBB2401  NEKFKNRATLTVDKSKSTAYMELSSLRSEDTAVYYCTRESGTGMDYWGQGTLVTVSSGG
           *******.:*:.::**.* *:*:***:********************************

Hum2401    GGSGGGGSGGGGSGGGGSDIQMTQSPSSLSASVGDRATISCKASQSVDYDGDSYMNWYQQ
HumBB2401  GGSGGGGSGGGGSGGGGSDIQMTQSPSSLSASVGDRATISCKASQSVDYDGDSYMNWYQQ
           ************************************************************

Hum2401    KPGQAPKLLIYAASNLESGIPSRFSGSGSGTDFTLTISSLQPEDFATYYCQQSHEDPWTF
HumBB2401  KPGQAPKLLIYAASNLESGIPSRFSGSGSGTDFTLTISSLQPEDFATYYCQQSHEDPWTF
           ************************************************************

Hum2401    GQGTKVEIKRASCAEDKLISEEDLNGAHHHHHH
HumBB2401  GQGTKVEIKRASCAEDKLISEEDLNGAHHHHHH
           *********************************
```

FIG. 10

Western: Anti-His antibody

COMPOSITIONS AND METHODS FOR TREATMENT OF DISEASES INVOLVING CXCL1 FUNCTION

CROSS-REFERENCE TO RELATED APPLICATIONS

This application is the National Stage entry of International Application No. PCT/US20/15457, filed 28 Jan. 2020, which claims priority to U.S. Provisional Application No. 62/797,573, filed on Jan. 28, 2019. The content of the aforementioned applications are herein incorporated by reference in their entirety.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "3000047-002001 Sequence_Listing_ST25.txt" created on 16 Sep. 2020, and 39,116 bytes in size) is submitted concurrently with the instant application, and the entire contents of the Sequence Listing are incorporated herein by reference.

BACKGROUND

1. Field

The present disclosure relates to antibodies, for example monoclonal antibodies, and their use in clinical patient evaluation and therapy. The present disclosure further relates to a method for modulating the activity of human chemokine (C-X-C motif) ligand 1, CXCL-1 protein (hereinafter, referred to as CXCL1). In an aspect, antibodies described herein are capable of being used as a medicament for the prevention and/or treatment of diseases involving CXCL1 function, for example, pathological angiogenesis, inflammatory diseases and cancers.

2. Background

Angiogenesis is a process involving the growth of new blood vessels from pre-existing vessels. In healthy adults, angiogenesis is quiescent in most of the organs, however, angiogenesis may occur in certain pathological conditions, such as during benign or malignant tumor growth, retinal disorders and wound healing. Targeting angiogenesis for treating cancer was proposed in the 1970s and clinical studies have resulted in the development of a number of therapeutic compounds, including humanized monoclonal antibodies to target this essential aspect of tumor development. One humanized monoclonal antibody (mAb), bevacizumab that targets the angiogenic factor VEGF (Vascular Endothelial Growth Factor) has obtained Food and Drug Agency (FDA) approval for treating cancers in association with standard chemotherapeutic agents. However, targeting VEGF alone has been only partially successful. Evasion of treatment could arise via various mechanisms so there remains a need for additional anti-angiogenic compounds that can be used alone or in combination with anti-cancer treatments, including other mAbs to improve clinical management and outcomes for cancer patients.

Chemokines, also referred as to as chemotactic cytokines, are known to be critical mediators of the inflammatory response by regulating the recruitment of cells from both the innate and adaptive immune systems to diseased tissues. Dysregulated expression and activity of certain chemokines have been implicated in cancer initiation and progression. Specifically, chronic chemokine exposure is associated with macrophage and T cell accumulation, chronic activation of macrophages, abnormal angiogenesis and DNA damage due to the presence of reactive oxygen species. Furthermore, chemokines have been known to regulate pivotal processes during tumor progression including primary tumor growth, tumor angiogenesis and development of metastatic disease. Chemokines may also enhance epithelial-stromal interactions facilitating tumor growth and invasion.

For example, chemokines characterized by an ELR motif such as human CXCL1/growth-related oncogene (GRO) is known to induce angiogenesis in vitro and in vivo. CXCL1 binds to and activates the chemokine receptor CXCR2, which is considered the key receptor in the angiogenic reaction. CXCL1 is potently active on neutrophils, inducing a marked recruitment of these cells into inflammatory sites. Neutrophils can synthesize and store molecules with known angiogenic activity, including vascular endothelium growth factor (VEGF-A), CXCL8/IL-8, CXCL1/GRO, and hepatocyte growth factor, suggesting that neutrophils can play a key role in the angiogenic process induced by CXC-ELR$^+$ chemokines including CXCL1.

Human CXCL1 also functions as a tumor-related factor. It has been shown that the amount of human CXCL1 fluctuates at the gene level and at the protein level in the tissue or blood of patients with malignant tumors, such as urothelial cancer, large-bowel cancer, ovary cancer, or malignant melanoma.

U.S. Pat. No. 9,309,312 discloses purified anti-human CXCL1 monoclonal antibodies or purified antigen-binding fragments thereof, which specifically recognize several amino acid sequence regions of CXCL1 protein. U.S. Pat. No. 9,309,312 also discloses using these antibodies or fragments in an immunoassay method for measuring a human CXCL1 protein.

US 20160108117 discloses antibodies or fragments thereof directed to CXCL1, said antibody or fragment being capable of binding to the human chemokine CXCL1 with an equilibrium dissociation constant (KD) of at most 16 nM, as determined by surface plasmon resonance. US 20160108117 also discloses using these antibodies or fragments in an in vitro diagnostic and/or prognostic method of a pathological angiogenesis disease or a disease characterized by undesirable excessive neovascularization in a subject.

Advantageously, the novel materials and methods provided here for blocking CXCL1 overcome shortfalls of current angiogenesis inhibitor drugs. Anti-CXCL1 mAbs of the present disclosure could address the aforementioned limitations.

There remains a need to develop better methods and compositions that can treat and/or prevent diseases involving pathological angiogenesis. A solution to this technical problem is provided by the embodiments characterized in the claims.

BRIEF SUMMARY

In an aspect, the disclosure provides for anti-human chemokine CXCL1 monoclonal antibodies or antigen-binding fragments thereof. In another aspect, the antibodies are isolated or recombinant.

In yet another aspect, the disclosure provides for anti-human chemokine CXCL1 monoclonal antibodies or antigen-binding fragments thereof wherein the antibodies or the antigen-binding fragments thereof bind to human chemokine CXCL1 protein having the amino acid sequence of (SEQ ID NO: 5)
ASVATELRCQCLQTLQGIHPKNIQSVNVKSPGPHCAQTEVIATLKNGRKA

CLNPASPIVKKIIEKMLNSDKSN.

In another aspect, an antibody described herein comprises an immunoglobulin heavy chain having the amino acid sequence of SEQ ID NO: 2 or a variant thereof and an immunoglobulin light chain having the amino acid sequence of SEQ ID NO: 4 or a variant thereof.

The disclosure further provides for an antibody or the antigen-binding fragment thereof, wherein the variant of the immunoglobulin heavy chain comprises at least one amino acid addition, substitution, insertion, and/or deletion in the amino acid sequence of SEQ ID NO: 2. In another aspect, the variant of the immunoglobulin light chain comprises at least one amino acid addition, substitution, insertion, and/or deletion in the amino acid sequence of SEQ ID NO: 4.

In another aspect, an antibody or antigen-binding fragment described herein is produced by using hybridoma clone HL2401.

In an aspect, an antibody or antigen-binding fragment thereof described herein is labeled with a toxin. In another aspect, an antibody or antigen-binding fragment thereof described herein is labeled with a radionucleotide, a fluorescent dye, a fluorescent protein, an enzyme, biotin and/or (strept)avidin. In yet another aspect, the radionucleotide is $^{64}Cu$, $^{111}In$, $^{99}Tc$, $^{14}C$, $^{131}I$, $^{3}H$, $^{32}P$, or $^{35}S$. In an aspect, the fluorescent dye is fluorescein isothiocyanate (FITC), rhodamine, Texas red, Cy3, or Cy5. In another aspect, the fluorescent protein is phycoerythrin (PE), allophycocyanin (APC), or green fluorescent protein (GFP). An enzyme described herein may be selected from the group consisting of horseradish peroxidase, alkaline phosphatase, or glucose oxidase.

In an aspect, the disclosure provides for an isolated nucleic acid molecule encoding an antibody or an antigen-binding fragment thereof described herein.

The disclosure further provides for a vector comprising a nucleic acid molecule described herein.

In an aspect, the disclosure further provides for a host cell comprising a nucleic acid molecule or vector described herein.

The disclosure further provides for a pharmaceutical composition comprising at least one active ingredient selected from the group consisting of an antibody or an antigen-binding fragment thereof described herein, a pharmaceutically acceptable carrier, and optionally, pharmaceutically acceptable excipient(s) and/or stabilizer(s).

The disclosure further provides for a method of treating a patient or individual by administering a compound, composition, antibody, or antigen-binding fragment thereof to a patient or individual in need thereof. In an aspect, the patient or individual has a pathological angiogenesis disease or a disease caused by excessive neovascularization. In another aspect, the pathological angiogenesis disease or the disease caused by excessive neovascularization is selected from the group consisting of cancers with abnormal angiogenesis, ophthalmological diseases with abnormal angiogenesis, rheumatoid arthritis, psoriasis, angioma, endometriosis, and kaposi sarcoma.

The disclosure further provides for a method of detecting human CXCL1 in a sample using an antibody or antigen-binding fragment thereof described herein.

In another aspect, an antibody described herein comprises a heavy chain variable domain comprising complementarity-determining region (CDR) 1 consisting of the amino acid sequence of SEQ ID NO: 6, CDR2 consisting of the amino acid sequence of SEQ ID NO: 7, and CDR3 consisting of the amino acid sequence of SEQ ID NO: 8, and a light chain variable domain comprising CDR1 consisting of the amino acid sequence of SEQ ID NO: 9, CDR2 consisting of the amino acid sequence of SEQ ID NO: 10, and CDR3 consisting of the amino acid sequence of SEQ ID NO: 11.

In another aspect, the light chain variable domain comprises the amino acid sequence of SEQ ID NO: 12 or 34.

In another aspect, the heavy chain variable domain comprises the amino acid sequence selected from the group consisting of SEQ ID NO: 14, 18, 36, or 38.

In another aspect, the antibody comprises the amino acid sequence selected from the group consisting of SEQ ID NO: 16, 20, 22, and 24.

In another aspect, the light chain variable domain comprises a signal peptide comprising the amino acid sequence of SEQ ID NO: 26.

In another aspect, the light chain variable domain comprises the amino acid sequence of SEQ ID NO: 28.

In another aspect, the heavy chain variable domain comprises a signal peptide comprising the amino acid sequence of SEQ ID NO: 27.

In another aspect, the heavy chain variable domain comprises the amino acid sequence of SEQ ID NO: 30 or 32.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1F shows numbering and regions the complementarity-determining regions (CDRs) in the light chain (VL) of the HL2401 clone.

FIG. 1G shows numbering and regions the CDRs in the heavy chain (VH) of the HL2401 clone.

FIG. 10 shows sequence alignment according to another embodiment of the present disclosure.

DETAILED DESCRIPTION

Figure 1A:
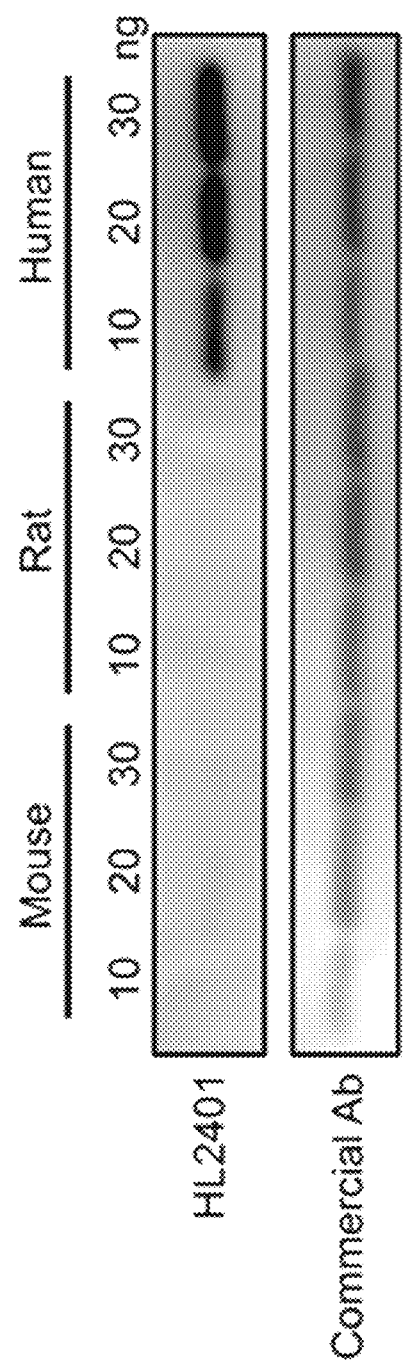
FIG. 1A shows anti-CXCL1 neutralizing monoclonal mouse antibody (HL2401) binds to recombinant human CXCL1, but not mouse and rat CXCL1.

The present disclosure demonstrates the increased angiogenic potential of human prostate cancer cells that overexpressed the Bcl2 proto-oncogene. Specifically, increased Bcl2 expression enhanced the tumorigenic and angiogenic ability of human prostate cancer xenografts. For example, culturing human endothelial cells (HUVEC and HDMEC) in conditioned media from Bcl2-overexpressing human prostate cancer cells resulted in increased rates of proliferation and the expression of key anti-apoptotic genes/proteins. This possibly provides a survival advantage over endothelial cells grown in conditioned media from cancer cells with low Bcl2 expression. Comparative genomic profiling of the treated and untreated endothelial cells revealed approximately 250 differentially expressed genes ($p<0.001$). After validation studies, CXCL1, a chemokine, stood out among several secreted proteins of interest (fold-change 3.96, $p<2.22E-16$).

CXCL1, a secreted growth factor that interacts with the G-protein-coupled receptor CXCR2, plays an important role not only in angiogenesis but also in inflammation and is a known chemo-attractant for neutrophils. Through a series of investigations, the present inventors showed that CXCL1 influences neo-angiogenesis through regulation of EGF and ERK 1/2 signaling, and cellular proliferation via increases in cyclin D3 and cdk4 levels, and have confirmed the role of CXCL1 in tumor establishment and survival in in vitro and in vivo studies.

Given the role of CXCL1 in angiogenesis, it is possible to inhibit angiogenesis, thus treat diseases, by blocking the binding of CXCL1 to CXCR2. Therefore, pharmaceutical agents blocking the CXCL1 pathway are capable of treating many angiogenesis-dependent diseases, including but not limited to, cancer.

Monoclonal antibodies (mAbs) have become a new class of therapeutic agents due to their ability to bind with high-specificity to a target, their long plasma half-life, and their low toxicity/side effects. Furthermore, with the advent of full human antibody technology, immunogenicity issues are avoided. Therefore, monoclonal antibodies have become a mainstay for pharmaceutical compositions.

Currently, no mAb containing amino acid sequence identical or similar to the present disclosure has been disclosed for the inhibition of angiogenesis and the treatment of cancers and other angiogenesis-dependent diseases.

The present disclosure provides mAb that specifically bind to CXCL1. The CXCL1 mAb can not only bind but also neutralize CXCL1.

In one embodiment, the present disclosure describes antibodies, or portions thereof, binding to CXCL1.

In another embodiment, the antibodies can be used to block angiogenesis, including treating angiogenesis-dependent diseases. Such disorders include, but are not limited to, retinopathy, age related macular degeneration, chronic articular rheumatism and psoriasis, disorders associated with inappropriate or inopportune invasion of vessels such as diabetic retinopathy, neovascular glaucoma, restenosis, capillary proliferation in atherosclerotic plaques and osteoporosis, and cancer associated disorders, such as solid tumors, solid tumor metastases, angiofibromas, retrolental fibroplasia, hemangiomas, Kaposi's sarcoma and all cancers which may require neovascularization to support tumor growth.

In another embodiment, the present disclosure also provides nucleic acids comprising nucleotide sequences encoding such antibodies; vectors comprising such nucleic acids; host cells and organisms comprising such nucleic acids and/or vectors; and compositions, such as pharmaceutically acceptable compositions and kits, comprising such proteins, nucleic acids, vectors, and/or cells and typically one or more additional ingredients that can be active ingredients or inactive ingredients that promote formulation, delivery, stability, or other characteristics of the composition (e.g., various carriers).

In another embodiment, the present disclosure also provides amino acid comprising amino acid sequences encoding such antibodies.

In another embodiment, the present disclosure further provides uses of antibodies or fragments thereof in the modulation of CXCL1-mediated biological activities, for example, inhibiting vascular endothelial cell proliferation and angiogenesis in the treatment of angiogenesis-dependent diseases related thereto.

Advantageously, the materials and methods provided herein for blocking binding of CXCL1 to its cognate receptor, i.e., CXCR2, overcome shortfalls of current angiogenesis inhibitor drugs. The antibodies of the present disclosure target an independent angiogenic pathway different from that of the classical VEGF/VEGFR pathway. The CXCL1 chemokine pathway is both angiogenic and inflammatory. Moreover, the CXCL1 chemokine can induce an autocrine proliferation pathway because tumor cells express the receptors CXCR1 and CXCR2. Thus, by inhibiting the CXCL1 chemokine, the antibodies or fragments thereof of the present disclosure may inhibit angiogenesis, inflammation, and proliferation.

In another embodiment, the mAbs according to the present disclosure may be used as a medicament. In particular, the mAbs can be used for the treatment of angiogenesis-dependent diseases.

The term "human CXCL1" as used herein refers to a protein or a natural mutant thereof comprising the amino acid sequence according to Genbank NM_001511. The term "natural mutant" refers to a mutant existing in the nature. Examples of such a mutant include a mutant comprising an amino acid sequence having a deletion, a substitution, an addition, or an insertion of one or several amino acids in the aforementioned amino acid sequence of human CXCL1 and a mutant having 95% or more, preferably 98% or more, and more preferably 99% or more amino acid sequence identity with the aforementioned amino acid sequence of human CXCL1. Here, the term "identity" refers to the percentage (%) of the total number of amino acid residues of the amino acid sequence in question that are identical to amino acid residues of the amino acid sequence of human CXCL1 when the two amino acid sequences are aligned such that the highest possible degree of agreement between them is achieved. In this case, sequence alignment can be carried out by introducing or not introducing gaps, and the number of gaps introduced is included when the percentage is calculated. Also, the term "several" refers to an integer between 2 and 10, such as between 2 and 7, 2 and 5, 2 and 4, and 2 and 3. Specific examples of a natural mutant include mutants based on polymorphism such as SNP (single nucleotide polymorphism) and splicing mutants. The above substitution is preferably a conservative amino acid substitution. If the substitution is a conservative amino acid substitution, a mutant resulting from the conservative amino acid substitution may have a structure or properties substantially equivalent to those of human CXCL1 having the above amino acid sequence. As conservative amino acids, nonpolar amino acids (glycine, alanine, phenylalanine, valine, leucine, isoleucine, methionine, proline, and tryptophan) and polar amino acids (amino acids other than nonpolar amino acids), charged amino acids (acidic amino acids (aspartic acid and glutamic acid) and basic amino acids (arginine, histidine, and lysine)) and non-charged amino acids (amino acids other than charged amino acids), aromatic amino acids (phenylalanine, tryptophan, and tyrosine), branched amino acids (leucine, isoleucine, and valine), and aliphatic amino acids (glycine, alanine, leucine, isoleucine, and valine), are known, for example.

In an embodiment, conservative substitutions may include those, which are described by Dayhoff in "The Atlas of Protein Sequence and Structure. Vol. 5", Natl. Biomedical Research, the contents of which are incorporated by reference in their entirety. For example, in an aspect, amino acids, which belong to one of the following groups, can be exchanged for one another, thus, constituting a conservative exchange: Group 1: alanine (A), proline (P), glycine (G), asparagine (N), serine (S), threonine (T); Group 2: cysteine (C), serine (S), tyrosine (Y), threonine (T); Group 3: valine (V), isoleucine (I), leucine (L), methionine (M), alanine (A), phenylalanine (F); Group 4: lysine (K), arginine (R), histidine (H); Group 5: phenylalanine (F), tyrosine (Y), tryptophan (W), histidine (H); and Group 6: aspartic acid (D), glutamic acid (E). In an aspect, a conservative amino acid substitution may be selected from the following of T→A, G→A, A→I, T→V, A→M, T→I, A→V, T→G, and/or T→S.

In a further embodiment, a conservative amino acid substitution may include the substitution of an amino acid by another amino acid of the same class, for example, (1) nonpolar: Ala, Val, Leu, Ile, Pro, Met, Phe, Trp; (2) uncharged polar: Gly, Ser, Thr, Cys, Tyr, Asn, Gln; (3) acidic: Asp, Glu; and (4) basic: Lys, Arg, His. Other conservative amino acid substitutions may also be made as follows: (1) aromatic: Phe, Tyr, His; (2) proton donor: Asn, Gln, Lys, Arg, His, Trp; and (3) proton acceptor: Glu, Asp, Thr, Ser, Tyr, Asn, Gln (see, for example, U.S. Pat. No. 10,106,805, the contents of which are incorporated by reference in their entirety).

In another embodiment, conservative substitutions may be made in accordance with Table 1. Methods for predicting tolerance to protein modification may be found in, for example, Guo et al., Proc. Natl. Acad. Sci., USA, 101(25): 9205-9210 (2004), the contents of which are incorporated by reference in their entirety.

In an aspect, sequences described herein may include 1, 2, 3, 4, 5, 10, 15, 20, 25, or 30 amino acid or nucleotide mutations, substitutions, deletions.

The term "antibody" herein is used in the broadest sense and specifically includes full-length monoclonal antibodies, polyclonal antibodies, multi-specific antibodies (e.g., bi-specific antibodies), and antibody fragments, so long as they exhibit the desired biological activity. Various techniques relevant to the production of antibodies are provided in Harlow et al. Antibodies: A laboratory Manual, Cold Spring Harbor Laboratory Press, Cold Spring Harbor, N.Y. 1988.

The term "monoclonal antibody" as used herein refers to a polypeptide containing an immunoglobulin- or its fragment-derived framework region (FR) and a complementarity determining region (CDR) and being capable of specifically binding to and recognizing an antigen. Therefore, the term "anti-human CXCL1 monoclonal antibody" in the present disclosure refers to a polypeptide capable of specifically binding to human CXCL1 or a fragment thereof and recognizing the human CXCL1 or a fragment thereof. The term "specifically binding" refers to binding to only a target antigen (human CXCL1 or a fragment thereof in the present disclosure).

A typical immunoglobulin molecule consists of a tetramer in which two sets, each consisting of two polypeptide chains referred to as a heavy chain and a light chain, are connected to each other via disulfide bond. A heavy chain comprises a heavy chain variable region (VH) on the N-terminus and a heavy chain constant region (CH) on the C-terminus. A light chain comprises a light chain variable region (VL) on the N-terminus and a light chain constant region (CL) on the C-terminus. Of these regions, VH and VL are particularly important since they are involved in the binding specificity of the antibody. VH and VL each comprises about 110 amino acid residues, wherein three complementarity determining regions (CDR1, CDR2, and CDR3) directly involved in binding specificity with an antigen and four framework regions (FR1, FR2, FR3, and FR4) functioning as framework structures for variable regions are present. A complementary determining region is known to form conformation complementary to an antigen molecule and determine the specificity of the relevant antibody (E. A. Kabat et al., 1991, Sequences of proteins of immunological interest, Vol. 1, eds. 5, NIH publication). Whereas amino acid sequences of constant regions remain almost unchanged among antibodies of the same species, amino acid sequences of complementary determining regions are highly variable among antibodies. Hence, complementary strand determining regions are also referred to as hypervariable regions. In a variable region, such complementarity determining regions (CDRs) and framework regions are arranged in the direction from an amino terminus to a carboxy terminus in order of FR1, CDR1, FR2, CDR2, FR3, CDR3, and FR4. VL and VH form a dimer with each other so as to form an antigen binding site within an immunoglobulin molecule. Regarding immunoglobulin, IgG, IgM, IgA, IgE, and IgD classes are known. The antibody of the present disclosure may be of any class and is preferably IgG.

An antibody useful in the present disclosure may be derived from every animal source including birds and mammals. Examples of such the animal or bird source include mice, rats, guinea pigs, rabbits, goats, donkeys, sheep, camels, horses, chickens, and humans. Also, "monoclonal antibody" in the present disclosure may be chemically synthesized or synthesized using a recombinant DNA method. For example, recombinant antibodies such as chimeric antibodies and humanized antibodies are also encompassed in the present disclosure.

A "humanized" antibody is a human/non-human chimeric antibody that contains minimal sequence derived from non-human immunoglobulin. For the most part, humanized antibodies are human immunoglobulins (recipient antibody) in which resides from a hypervariable region of the recipient are replaced by residues from a hypervariable region of a non-human species (donor antibody) such a mouse, rat, rabbit having the desired specificity, affinity and capacity.

The term "hypervariable" region when used herein refers to the amino acid residues of an antibody that are responsible for antigen-binding. The hypervariable region generally comprises amino acid residues from a "complementarity-determining region" or "CDR"" (residues 24-34 (L1), 50-56 (L2) and 89-97 (L3) in the light-chain variable domain and 31-35 (H1), 50-65 (H2) and 95-102 (H3) in the heavy-chain variable domain and/or those residues from a typervariable loop" (residues 26-32 (L1), 50-52 (L2) and 91-96 (L3) in the light chain variable domain and 26-32 (H1), 53-55 (H2) and 96-101 (H3) in the heavy-chain variable domain.

The term "fragment thereof" in "monoclonal antibody or a fragment thereof" as used herein refers to a partial region of the antibody and specifically refers to a polypeptide chain or a complex thereof having activity substantially equivalent to the antigen-specific binding activity of the antibody. Examples of such a fragment include an antibody portion containing at least one of the above antigen binding sites and specifically, a polypeptide chain or a complex thereof having at least one VL and at least one VH. Specific examples of such a polypeptide chain or a complex thereof include many sufficiently characterized antibody fragments and the like generated via cleavage of immunoglobulin with various peptidases. More specific examples of such antibody fragments include Fab, F(ab')2, and Fab'. Fab is a fragment generated by cleaving an IgG molecule with papain, by which cleavage is carried out at a position closer to the N-terminal side than the disulfide linkage of a hinge part. Fab is composed of a polypeptide comprising VH and CH1 which is adjacent to VH among the 3 domains (CH1, CH2, and CH3) composing CH and a light chain. F(ab')2 is a dimer of Fab', which is generated by cleaving an IgG molecule with pepsin at a position closer to the C-terminal side than the disulfide linkage of the hinge part. Fab' has a structure substantially equivalent to that of Fab, although the H chain is somewhat longer than that of Fab since it contains the hinge part (Fundamental Immunology, Paul ed., 3d ed., 1993). Fab' can be obtained by reducing F(ab')2 under mild conditions and then cleaving the disulfide linkage in the hinge region. All of these antibody fragments contain antigen binding sites, so that they are capable of specifically binding to antigens (that is, human CXCL1 or a fragment thereof in the present disclosure).

The above "fragment thereof" in the present disclosure may be chemically synthesized or synthesized using a recombinant DNA method. An example of such a fragment is an antibody fragment newly synthesized using a recombinant DNA method. Specific examples of such a fragment include, but are not limited to, a monomeric polypeptide molecule prepared by artificially linking one or more VL and one or more VH of the antibody of the present disclosure via a linker peptide or the like having an appropriate length and sequence and a multimeric polypeptide thereof. Examples of such a polypeptide include single chain Fv (scFv: single chain fragment of variable region) (see Pierce catalog and Handbook, 1994-1995, Pierce Chemical co., Rockford, Ill.) and synthetic antibodies such as a diabody, a triabody, and a tetrabody. In an immunoglobulin molecule, VL and VH are generally separately located on different polypeptide chains (a light chain and a heavy chain). Single chain Fv is a synthetic antibody fragment that has a structure in which these variable regions are linked with a flexible linker having a sufficient length and the linked regions are contained in a single polypeptide chain. Within single chain Fv, both variable regions can be self-assembled to form a single functional antigen binding site. Single chain Fv can be obtained by incorporating a recombinant DNA encoding the single chain Fv into a phage genome using a known technique and then causing the expression of the DNA. A diabody is a molecule having a structure based on the dimeric structure of single chain Fv (Holliger et al., 1993, Proc. Natl. Acad. Sci. U.S.A., 90: 6444-6448). For example, when the length of the above linker is shorter than about 12 amino acid residues, two variable sites within single chain Fv cannot undergo self-assembly. However, the two variable sites are caused to form a diabody and specifically two single chain Fvs are caused to interact with each other, enabling the assembling of VL of one Fv chain and VH of the other Fv chain. Hence, two functional antigen binding sites can be formed (Marvin et al., 2005, Acta Pharmacol. Sin., 26: 649-658). Moreover, a cysteine residue is added to the C-terminus of single chain Fv, so that disulfide bond of the two Fv chains can be formed and thereby formation of a stable diabody become possible (Olafsen et al, 2004, Prot. Engr. Des. Sel., 17: 21-27). As described above, a diabody is a divalent antibody fragment. However, each antigen binding site is not required to bind to the same epitope and may have bi-specificity such that the antigen binding sites recognize and specifically bind to different epitopes. A triabody and a tetrabody have a trimeric structure and a tetrameric structure, respectively, based on a single chain Fv structure in a manner similar to a diabody. A triabody and a tetrabody are a trivalent antibody fragment and a quadrivalent antibody fragment, respectively, or may be multiple specific antibodies.

Furthermore, examples of the above "fragment thereof" include antibody fragments that are identified using phage display libraries (e.g., see McCafferty et al., 1990, Nature, Vol. 348, 522-554) and have antigen-binding capacity. In addition, also see Kuby, J., Immunology, 3rd ed., 1998, W. H. Freeman & Co., New York, for example.

The antibody or a fragment thereof of the present disclosure can be modified. The term "modified or modification" used herein refers to both functional modification required for the antibody or a fragment thereof of the present disclosure to have activity of specifically binding to human CXCL1 (e.g., glycosylation) and modification for labeling required for detection of the antibody or a fragment thereof of the present disclosure. In one embodiment, antibodies or fragments thereof bind to the extracellular domains of two or more targets of a protein selected from the group consisting of the above-mentioned proteins, and the affinity value (Kd) is less than $1 \times 10$ μM. Also, glycosylation of the antibody of the present disclosure may be altered for adjusting the affinity of an antibody for a target antigen. Such alteration can be achieved by, for example, changing one or more glycosylation sites within the antibody sequence. More specifically, for example, one or more amino acid substitutions are introduced into an amino acid sequence composing one or more glycosylation sites within FR so as to remove the glycosylation sites, so that deglycosylation can be achieved at the sites. Such deglycosylation is effective for increasing the affinity of an antibody for an antigen (U.S. Pat. Nos. 5,714,350 and 6,350,861). Optionally, the antibody carries a further effector function such as an immune stimulating domain or toxin.

A "pharmaceutical composition" is a composition suitable for administration to a human being in a medical setting. Preferably, a pharmaceutical composition is sterile and produced according to GMP guidelines.

The present disclosure contemplates pharmaceutical (or therapeutic) composition useful for practicing the therapeutic methods described herein. Therapeutic compositions of the present disclosure contain a physiologically tolerable carrier together with a therapeutically effective amount of an antibody as described herein, dissolved or dispersed therein as an active ingredient. In a preferred embodiment, the therapeutic composition is not immunogenic or has reduced immunogenicity when administered to a mammal or human patient for therapeutic purposes. A therapeutically effective amount is an amount of an antibody of the disclosure sufficient to produce a measurable inhibition of angiogenesis in the tissue being treated, i.e., an angiogenesis-inhibiting amount. Inhibition of angiogenesis can be measured in situ by immunohistochemistry, or by other methods known to one skilled in the art.

The pharmaceutical compositions may contain the antibodies either in the free form or in the form of a pharmaceutically acceptable salt. As used herein, "a pharmaceutically acceptable salt" refers to a derivative of the disclosed antibodies wherein the antibodies may be modified by making acid or base salts of the agent. For example, acid salts are prepared from the free base (typically wherein the neutral form of the drug has a neutral –NH2 group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, ptoluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on antibodies may be prepared using a pharmaceutically acceptable base such as sodium hydroxide, potassium hydroxide, ammonium hydroxide, calcium hydroxide, trimethylamine or the like. In an especially preferred embodiment, the pharmaceutical compositions comprise the antibodies as salts of acetic acid (acetates), trifluoro acetates or hydrochloric acid (chlorides).

Pharmaceutical composition according to the disclosure may contain adjuvant selected from the group consisting of colony-stimulating factors, such as Granulocyte Macrophage Colony Stimulating Factor (GM-CSF, sargramostim), cyclophosphamide, imiquimod, resiquimod, and interferon-alpha. In a preferred embodiment, the pharmaceutical composition according to the disclosure the adjuvant is selected from the group consisting of colony-stimulating factors, such as Granulocyte Macrophage Colony Stimulating Factor (GM-CSF, sargramostim), cyclophosphamide, imiquimod and resiquimod. In a preferred embodiment of the pharmaceutical composition according to the disclosure, the adjuvant is cyclophosphamide, imiquimod or resiquimod. Even more preferred adjuvants are Montanide IMS 1312, Montanide ISA 206, Montanide ISA 50V, Montanide ISA-51, poly-ICLC (Hiltonal®) and anti-CD40 mAB, or combinations thereof.

The medicament of the disclosure may also include one or more adjuvants. Adjuvants are substances that non-specifically enhance or potentiate the immune response (e.g., immune responses mediated by CDS-positive T cells and helper-T (TH) cells to an antigen, and would thus be considered useful in the medicament of the present disclosure. Suitable adjuvants include, but are not limited to, 1018 ISS, aluminum salts, AMPLIVAX®, AS15, BCG, CP-870, 893, CpG7909, CyaA, dSLIM, flagellin or TLR5 ligands derived from flagellin, FLT3 ligand, GM-CSF, IC30, IC31, Imiquimod (ALDARA®), resiquimod, ImuFact IMP321, Interleukins as IL-2, IL-13, IL-21, Interferon-alpha or -beta, or pegylated derivatives thereof, IS Patch, ISS, ISCOMATRIX, ISCOMs, JuvImmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-17 4, OM-197-MPEC, ONTAK, OspA, PepTel® vector system, poly(lactide co-glycolide) [PLG]-based and dextran microparticles, talactoferrin SRL 172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995). Also, cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich et al., 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including antibodies or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 81 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present disclosure. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and derivatives thereof (e.g. AmpliGen®, Hiltonal®, poly-(ICLC), poly(IC-R), poly(I:C12U), non-CpG bacterial DNA or RNA as well as immunoactive small molecules and antibodies such as cyclophosphamide, sunitinib, Bevacizumab®, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g., anti-CD40, anti-TGFbeta, anti-TNFalpha receptor) and SC58175, which may act therapeutically and/or as an adjuvant. The amounts and concentrations of adjuvants and additives useful in the context of the present disclosure can readily be determined by the skilled artisan without undue experimentation.

Preferred adjuvants are anti-CD40, imiquimod, resiquimod, GM-CSF, cyclophosphamide, sunitinib, bevacizumab, interferon-alpha, CpG oligonucleotides and derivatives, poly-(1:C) and derivates, RNA, sildenafil, and particulate formulations with PLG or virosomes. In a preferred embodiment, the pharmaceutical composition according to the disclosure the adjuvant is selected from the group consisting of colony-stimulating factors, such as Granulocyte Macrophage Colony Stimulating Factor (GM-CSF, sargramostim), cyclophosphamide, imiquimod, resiquimod, and interferon-alpha.

In a preferred embodiment, the pharmaceutical composition according to the disclosure the adjuvant is selected from the group consisting of colony-stimulating factors, such as Granulocyte Macrophage Colony Stimulating Factor (GM-CSF, sargramostim), cyclophosphamide, imiquimod and resiquimod. In a preferred embodiment of the pharmaceutical composition according to the disclosure, the adjuvant is cyclophosphamide, imiquimod or resiquimod. Even more preferred adjuvants are Montanide IMS 1312, Montanide ISA 206, Montanide ISA 50V, Montanide ISA-51, poly-ICLC (Hiltonal®) and anti-CD40 mAB, or combinations thereof.

This composition is used for parenteral administration, such as subcutaneous, intradermal, intramuscular or oral administration. For this, the antibodies and optionally other molecules are dissolved or suspended in a pharmaceutically acceptable, preferably aqueous carrier. In addition, the composition can contain excipients, such as buffers, binding agents, blasting agents, diluents, flavors, lubricants, etc. The antibodies can also be administered together with immune stimulating substances, such as cytokines. An extensive listing of excipients that can be used in such a composition, can be, for example, taken from A. Kibbe, Handbook of Pharmaceutical Excipients (Kibbe, 2000). The composition can be used for a prevention, prophylaxis and/or therapy of adenomatous or cancerous diseases. Exemplary formulations can be found in, for example, EP2112253.

Method for Preparing Monoclonal Antibody and Hybridoma

One embodiment of the present disclosure provides a neutralizing IgG mAb to CXCL1. Specifically, mAb to CXCL1 may be prepared by first immunizing an appropriate animal, such as mouse, with CXCL1 protein. Hybridomas are then produced and screened for the production of CXCL1-reactive IgG antibodies using standard techniques (e.g., ELISA).

In order to generate a fully human anti-CXCL1 antibody, the DNA sequences of the heavy (SEQ ID NO: 1) and light (SEQ ID NO: 2) chains of this antibody were obtained by PCR using cDNA that had been reverse-transcribed from the RNA of antibody hybridoma as templates. As is well known in the art, individual amino acids can be encoded by different DNA sequences. Hence, the amino acid sequences of this antibody can be encoded by different DNA sequences, e.g., SEQ ID. NO: 1 encoding the amino acid sequence of the heavy chain (SEQ ID. NO: 2) and SEQ ID. NO: 3 encoding the amino acid sequence of the light chain (SEQ ID. NO: 4). These DNA sequences fall within the scope of the present disclosure. Furthermore, based on the common knowledge of antibody structure, some amino acids in an antibody may be substituted, deleted, or added, without detracting the biological activities of the antibody. In some cases, changes in the amino acid sequence of an antibody may even improve the biological activities and/or improve certain properties compared to the original antibody. Therefore, it is possible to modify the amino acid sequences of this anti-CXCL1 antibody to obtain antibody variants with similar, or even improved, biochemical or biological properties. These modified antibodies are within the scope of the present disclosure.

Anti-CXCL1 mAb of the present disclosure can be "humanized" through genetic engineering techniques known to those of ordinary skills in the art. After selecting high-affinity anti-CXCL1 IgG antibody-producing clones (e.g., HL2401) that are capable of neutralizing CXCL1, the cells are genetically engineered so that the hypervariable regions from a non-human antibody combining site derived from an anti-CXCL1 antibody can be 'grafted' onto the framework regions of human IgG antibody. This technique is known as complementary-determining region (CDR) grafting, which provides the production of a humanized IgG antibody having a pre-selected non-human antibody binding site specific for a given epitope on CXCL1. These IgG antibodies are then mass produced in HEK293 cells and then purified.

Similar to the above, humanized CXCL1 mAb was screened; a) for the production of CXCL1-reactive IgG antibodies using standard techniques (e.g., ELISA), b) for inhibition of in vitro tube formation and c) for inhibition of interaction between CXCL1 and CXCR2.

Antibodies of the disclosure are preferably administered to a subject in a pharmaceutically acceptable carrier. Typically, an appropriate amount of a pharmaceutically-acceptable salt is used in the formulation to render the formulation isotonic. Examples of the pharmaceutically acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered. The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. A typical daily dosage of the antibody used alone might range from about 1 (μg/kg to up to 100 mg/kg of body weight or more per day, depending on the factors mentioned above. Following administration of antibodies, preferably for treating retinopathy, age related macular degeneration, chronic articular rheumatism and psoriasis, disorders associated with inappropriate or inopportune invasion of vessels such as diabetic retinopathy, neovascular glaucoma, restenosis, capillary proliferation in atherosclerotic plaques and osteoporosis, and cancer associated disorders, such as solid tumors, solid tumor metastases, angiofibromas, retrolental fibroplasia, hemangiomas, Kaposi's sarcoma and all cancers which require neovascularization to support tumor growth, the efficacy of the therapeutic antibody can be assessed in various ways well known to the skilled practitioner. For instance, the size, number, and/or distribution of cancer in a subject receiving treatment may be monitored using standard tumor imaging techniques. A therapeutically-administered antibody that arrests tumor growth, results in tumor shrinkage, and/or prevents the development of new tumors, compared to the disease course that would occurs in the absence of antibody administration, is an efficacious antibody for treatment of cancer.

One embodiment of the present disclosure provides a method for detection of CXCL1 in a sample using the antibodies or fragments thereof described herein. In an aspect, the CXCL1 is human CXCL1. In particular, the present disclosure provides a method for detecting human CXCL1 in a sample, comprising the step of incubating the sample with the antibody and/or fragment thereof according to the invention.

In some embodiments, the sample is a biological sample.

The term "biological sample" encompasses a variety of sample types obtained from an organism that may be used in a diagnostic or monitoring assay. The term encompasses blood and other liquid samples of biological origin, solid tissue samples, such as a biopsy specimen, or tissue cultures or cells derived there from and the progeny thereof. Additionally, the term "biological sample" may encompass circulating tumor or other cells. The term "biological sample" specifically encompasses a clinical sample, and further includes cells in cell culture, cell supernatants, cell lysates, serum, plasma, urine, amniotic fluid, biological fluids including aqueous humour and vitreous for eye samples, and tissue samples. The term "biological sample" also encompasses samples that have been manipulated in any way after procurement, such as treatment with reagents, solubilization, or enrichment for certain components.

In some embodiments, the biological sample can be selected from a bodily fluid, a fraction thereof, a tissue extract, and a cell extract. In particular, the biological sample can be selected from a plasma sample and a tumor extract.

In some embodiments, the method for detecting human CXCL1 in a sample further comprises the step of detecting the binding of the antibody or fragment thereof according to the invention to human CXCL1.

The method for detecting human CXCL1 in a sample according to the invention can be based on various techniques, well known by one skilled in the art, including, but not limited to:

a western blot assay (CXCL1 or fragment thereof present in a cell lysate or in a solution being immobilized on a membrane, the membrane being thereafter incubated with the antibody of the invention, preferably labeled, in appropriate conditions well known in the art), an ELISA assay (CXCL1 or fragment thereof being immobilized on a microtiter plate, the said plate being thereafter incubated with the antibody of the invention, preferably labeled, in appropriate conditions well known in the art), an immunohistochemistry assay (the antibody, preferably labeled, being used to stain a sample containing fixed cells or tissues expressing CXCL1 or a fragment thereof, in appropriate conditions well known in the art), a flow cytometry assay (the antibody, preferably labeled, being used to stain a sample containing fixed or living cells expressing CXCL1 or a fragment thereof, in appropriate conditions well known in the art), In one embodiment of the method for detecting human CXCL1 in a sample according to the invention, the antibody of the invention is coated on a solid support.

These detection techniques are described, for example, in Sambrook, Fritsch and Maniatis—"Molecular Cloning A Laboratory Manual Second Edition Cold Spring Harbor Laboratory, 1989, the content of which is incorporated by reference in its entirety. Any other detection techniques requiring the use of an antibody are herein encompassed.

The presence and/or the amount of human CXCL1 in the sample can be determined by one or more of these techniques. Some of these techniques require labeling the antibody of the invention with a detectable marker, preferably a fluorescent or a luminescent marker.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multifunctional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the expression of the proteins in situ. Examples of the above antibody labels may include fluorescent dyes, e.g., fluorescein isothiocyanate (FITC), rhodamine, Texas red, Cy3, and Cy5, fluorescent proteins, e.g., phycoerythrin (PE), allophycocyanin (APC), and green fluorescent protein (GFP), enzymes, e.g., horseradish peroxidase, alkaline phosphatase, and glucose oxidase, and biotin or (strept)avidin. The antibody may be labeled with a radionucleotide, such as $^{64}$Cu, $^{111}$In, $^{99}$Tc, $^{14}$C, $^{131}$I, $^{3}$H, $^{32}$P or $^{35}$S, so that the tumor can be localized using immunoscintiography.

The present disclosure also provides a method for purifying human CXCL1 from a sample, comprising the step of incubating the sample with the antibody and/or fragment thereof according to the invention.

The method for purifying human CXCL1 from a sample according to the invention can be based on various techniques, well known by one skilled in the art, including, but not limited to flow cytometry assays, immunoprecipitation assays. These detection techniques are described, for example, in Sambrook, Fritsch and Maniatis—"Molecular Cloning A Laboratory Manual Second Edition Cold Spring Harbor Laboratory, 1989.

The present disclosure also provides a kit useful for carrying out the methods for detecting and/or purifying human CXCL1 in a sample according to the invention, the kit comprising: at least one antibody or fragment thereof according to the invention; and at least one reagent for detecting the antibody or fragment thereof according to the invention.

The reagent for detecting the antibody or fragment thereof according to the invention can be selected from the group consisting of ELISA reagents, Western blot reagents, and dot blot reagents.

The present disclosure also provides for in vitro or ex vitro diagnostic and/or prognostic method, and particularly to an in vitro diagnostic and/or prognostic method of a disease related to CXCL1, particularly of a pathological angiogenesis disease, in particular of clear cell renal cell carcinoma, in a subject, the method comprising: determining the expression and/or the level of expression of CXCL1 in a biological sample of the subject using at least one antibody and/or fragment thereof according to the invention.

Treatment of Pathologic Angiogenesis

The present disclosure provides for a method for the inhibition of angiogenesis in tissues, and thereby inhibiting events in the tissues, which depend upon angiogenesis. Generally, the method comprises administering to the tissue a composition comprising an angiogenesis-inhibiting amount of an antibody of the present disclosure.

As described earlier, angiogenesis includes a variety of processes involving neovascularization of a tissue including "sprouting", vasculogenesis, or vessel enlargement, all of which angiogenesis processes involve disruption of extracellular matrix collagen in blood vessels. With the exception of traumatic wound healing, corpus leuteum formation and embryogenesis, it is believed that the majority of angiogenesis processes are associated with disease processes and therefore the use of the present therapeutic methods is selective for the disease.

There are a variety of diseases in which angiogenesis is believed to be important, referred to as angiogenic diseases, including but not limited to, inflammatory disorders such as immune and non-immune inflammation, chronic articular rheumatism and psoriasis, disorders associated with inappropriate or inopportune invasion of vessels such as diabetic retinopathy, neovascular glaucoma, restenosis, capillary proliferation in atherosclerotic plaques and osteoporosis, and cancer associated disorders, such as solid tumors, solid tumor metastases, angiofibromas, fibroplasia, hemangiomas, Kaposi's sarcoma and the like cancers which require neovascularization to support tumor growth. Other suitable tumors include melanoma, carcinoma, sarcoma, fibrosarcoma, glioma and astrocytoma. Thus, methods, which inhibit angiogenesis in a diseased tissue, ameliorate symptoms of the disease and, depending upon the disease, can contribute to cure of the disease.

In some aspects, the antibodies or the antigen-binding fragment thereof of the disclosure are administered alone or in combination with anti-cancer treatments, such as, for example one or more chemotherapeutic agent, one or more immunotherapeutic agent, or combinations thereof.

As described herein, any of a variety of tissues, or organs comprised of organized tissues, can support angiogenesis in disease conditions including skin, muscle, gut, connective tissue, joints, bones and the like tissue in which blood vessels can invade upon angiogenic stimuli. Tissue, as used herein, also encompasses all bodily fluids, secretions and the like, such as serum, blood, cerebrospinal fluid, plasma, urine, synovial fluid, vitreous tumor.

Representative Routes of Administration

The antibodies of the disclosure can be administered parentally by injection or by gradual infusion over time. Although the tissue to be treated can typically be accessed in the body by systemic administration and therefore most often treated by intravenous administration of therapeutic compositions, other tissues and delivery means are contemplated where there is a likelihood that the tissue targeted contains the target molecule. Thus, antibodies and derivatives, thereof can be administered intravenously, intraperitoneally, intramuscularly, subcutaneously, intracaviatary, intravesically, transdermally, topically, intraocually, orally, or intranasally.

The description herein of any aspect or embodiment of the present disclosure using terms such as "comprising", "having", "including" or "containing" with reference to an element or elements is intended to provide support for a similar aspect or embodiment of the disclosure that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

EXAMPLES

The present disclosure may be further demonstrated through the following examples. It should be understood that the scope of this disclosure is not limited to the examples. Furthermore, those with skill in the art may modify or alter this disclosure after reading this disclosure; these modified variants should be regarded as equivalent to embodiments and fall into the scope of this disclosure.

The following examples, if not described in detail, use techniques commonly known to those with skill in the art and may follow the experimental protocols or conditions described by references such as Molecular Cloning, A Laboratory Manual (Sambrook, etc., Cold Spring Harbor Laboratory Press) or Antibodies: A Laboratory Manual, (Ed Harlow and David Lane, Cold Spring Harbor Laboratory Press), etc., or based on manufacture's instruction.

All patents, patent applications, provisional applications, and publications referred to or cited herein are incorporated by reference in their entirety, including all figures and tables, to the extent they are not inconsistent with the explicit teachings of this specification.

Following are examples, which illustrate procedures for practicing the disclosure. These examples should not be construed as limiting.

Example 1

Preparation of Human Anti-CXCL1 Antibody

Balb/cByJ mice were immunized multiple times with human recombinant CXCL1 protein. The anti-CXCL1 antibody titers in mouse sera were determined by the ELISA assay. After high anti-CXCL1 antibody titer in serum was reached, spleens were dissected and splenocytes isolated to fuse with myeloma cells to generate hybridoma cells. The fused hybridomas were grown in selection medium to generate hybridoma clones.

A mouse monoclonal antibody against CXCL1 was produced using a standard protocol of the Hybridoma and Protein Core Laboratories, University of Florida Interdisciplinary Center for Biotechnology Research (ICBR) (Chang et al, 2013). Two female Balb/cByJ mice were immunized with approximately 100 μg of native CXCL1 protein having the amino acid sequence of ASVATELRCQCLQTLQGIHPKNIQSVNVKSPGPH-CAQTEVIATLKNGRKACLNPASPIVKKII EKMLNSDKSN (SEQ ID NO: 5) diluted in sterile physiologic phosphate buffered saline (PBS) and emulsified in Ribi MPL+TDM adjuvant. The immunogen was administered on days 1, 21, 44, and 192. The test bleeds were collected 11 to 14 days after the second and third immunizations. The presence of anti-CXCL1 antibodies in the post-immunized serum was determined by western blots and ELISA. Six days after the fourth immunization, mouse #1 was euthanized and the splenic lymphocytes were collected and fused with mouse myeloma cells to form hybridoma cells (Uehara et al, 2005). The cultured media of the growing hybridoma mass cultures were collected and screened for anti-CXCL1 antibody production by ELISA. The mass cultures that tested positive by ELISA were subsequently tested for biologic effect in a proliferation assay utilizing HUVEC cells. The cultures that showed reactivity to CXCL1 in ELISA and exhibited anti-proliferative effects were grown out, and further cloned by limiting dilution. The cultured media collected from each clone were tested again by ELISA. The monoclonal antibodies were isotyped by ELISA and IsoStrip tested following manufacturer's protocol. The cultured medium of the final selected hybridoma clone was harvested, and purified through a protein G column (GE Healthcare Protein G Sepharose 4 Fast Flow). The concentration of the purified monoclonal anti-CXCL1 antibody (HL2401) was determined by Bradford Protein Assay and stored at 4° C. for future validation. A gel clot LAL assay from Lonza (Basel, Switzerland) ensured the antibody was free of endotoxins.

The hybridoma cell clones were grown in 96-well plates in RPMI-1640 complete medium. Supernatants were collected from each hybridoma clone and assayed for specific antibodies using ELISA. In this assay, ELISA plates were coated with soluble recombinant human CXCL1 and blocked with 2% BSA. Then, hybridoma supernatants were properly diluted and added to each well, followed by HRP-conjugated goat anti-mouse IgG. The plates were then incubated with HRP substrate and OD values read at a wavelength of 650 nm using a microplate reader.

A number of hybridoma clones that secrete anti-CXCL1 antibodies were identified. The hybridoma clones that secrete specific antibodies against CXCL1 were expanded to 6-well plates, and then T-175 flasks. Supernatants were harvested from the flasks. Isotypes of the antibodies secreted from hybridoma clones were determined using an IgG isotyping kit and concentrations of antibodies in the supernatants were measured by an ELISA assay using the corresponding antibody subtypes as a standard. Antibody concentration in the hybridoma supernatants were normalized and diluted. The antibody supernatants were used to compare relative binding affinities of antibodies to CXCL1 by an ELISA assay. By this approach, several monoclonal antibodies clones that show high affinity to CXCL1 were identified.

After the hybridoma clones expressing anti-CXCL1 antibodies were identified in the initial screening and inhibition of tube formation in secondary screen, the ability of the antibodies to block CXCL1-CXCR2 binding were examined in a tertiary screen. In this tertiary screening assay, 96-well ELISA plates were coated with human recombinant CXCL1 and blocked with BSA. In a separate 96-well plate, anti-CXCL1 antibodies at various concentrations were mixed with recombinant human CXCR2. The mixtures were incubated at 37° C. for one hour and then transferred to the ELISA plate that was blocked with BSA. After rinse, HRP-conjugated goat anti-human IgG was added to each well, followed by HRP substrate and OD reading at 650 in a microplate reader. By this methodology, a monoclonal antibody clone, designated as HL2401 that is capable of completely blocking CXCL1-CXCR2 binding was identified. HL2401 was confirmed as IgG by antibody isotyping.

FIG. 1A shows anti-CXCL1 neutralizing monoclonal mouse antibody (HL2401) binds to recombinant human CXCL1, but not mouse and rat CXCL1. In contrast, a commercial antibody shows cross reactions with mouse, rat, and human CXCL1. This result shows the superior specificity of HL2401 to that of the commercial antibody.

Figure 1B:
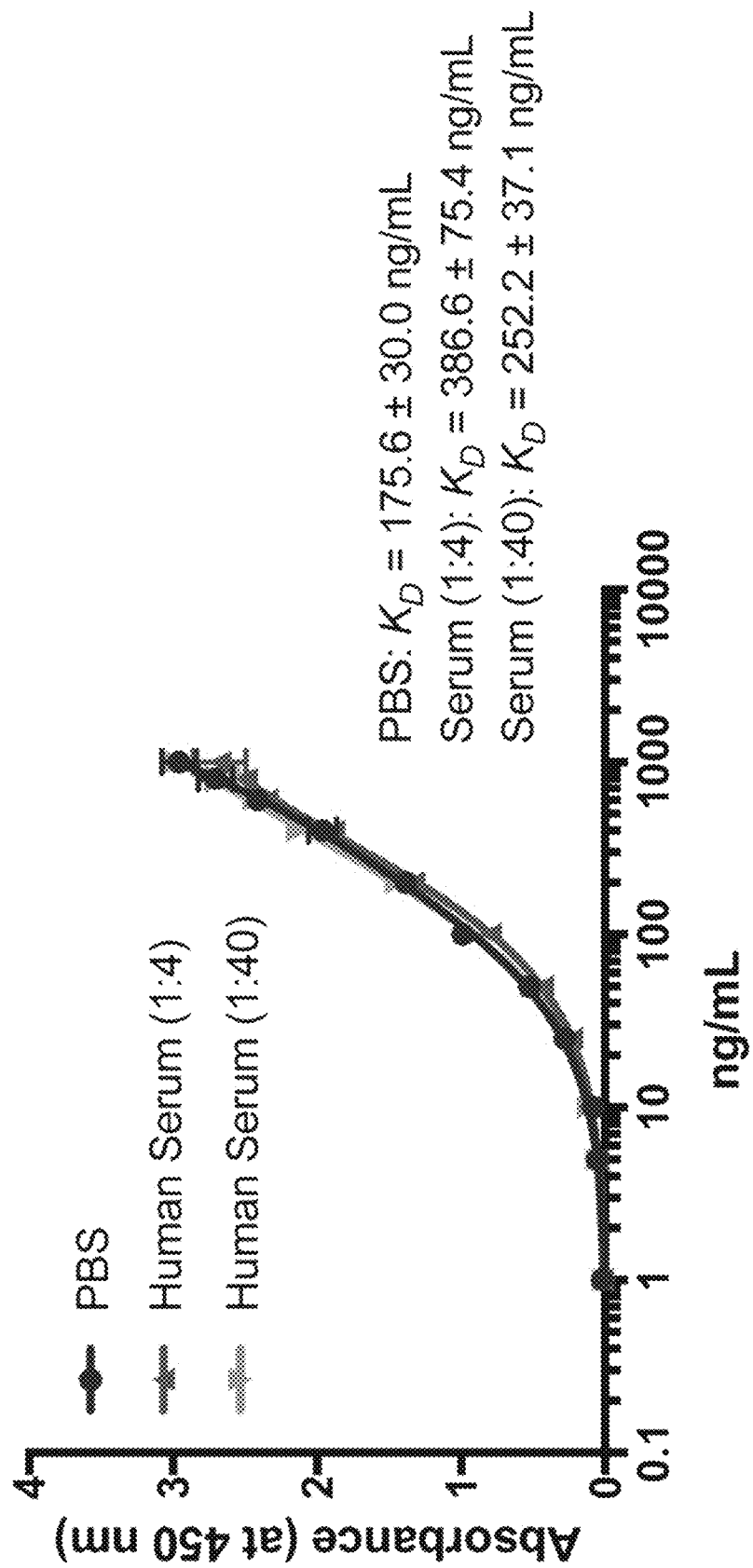
FIG. 1B shows the apparent affinity-binding constant (KD) value for CXCL1 in PBS and serum.

FIG. 1B shows the apparent affinity-binding constant ($K_D$) value for CXCL1 in PBS and serum (1:4 dilution and 1:40 dilution) were 175.6±30.0 ng/mL, 386.6±75.4 ng/and 252.2±37.1 ng/mL, respectively.

Figure 1C:
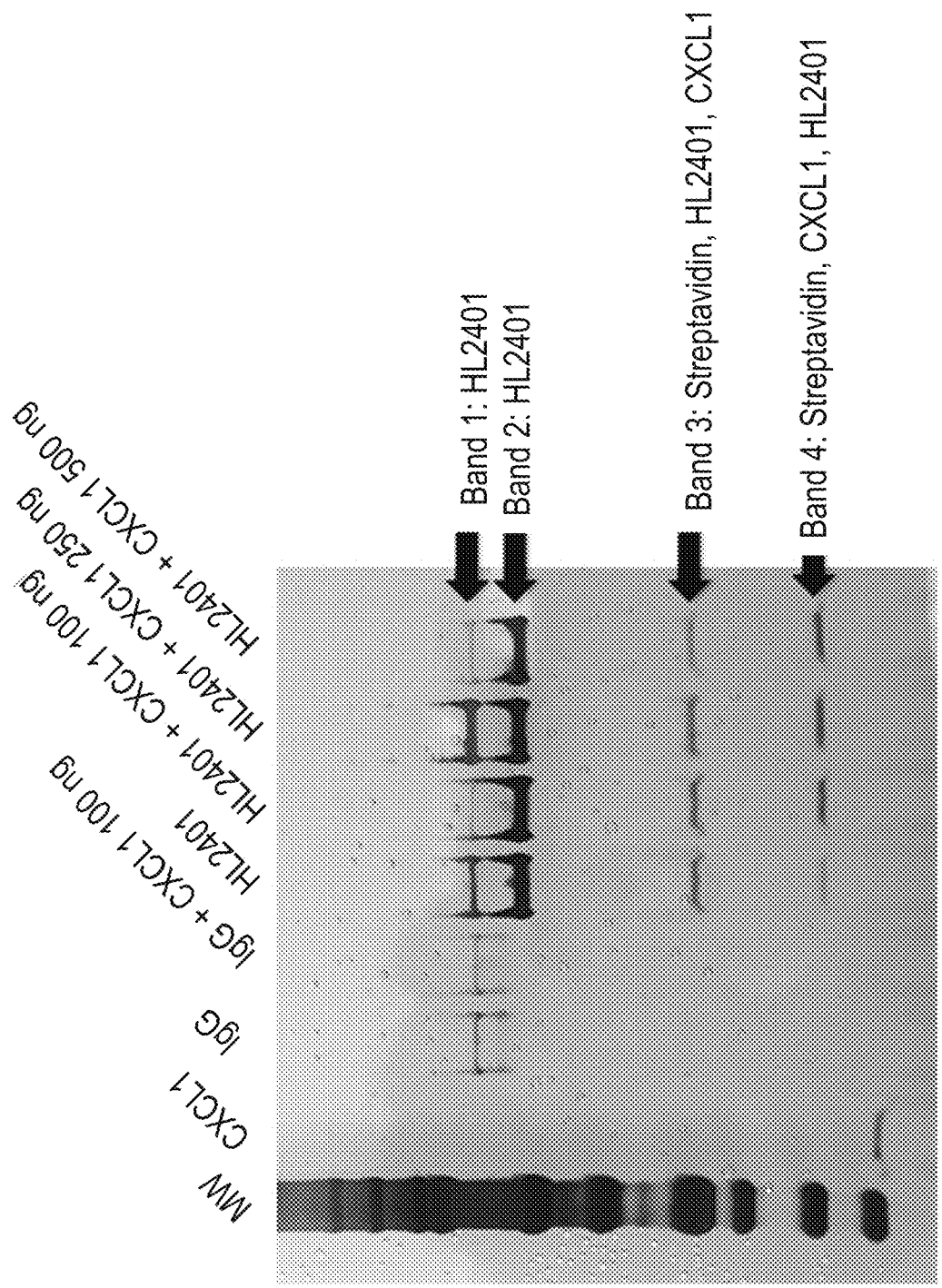
FIG. 1C shows immunoprecipitation followed by LC/MS-MS analysis confirmed that HL2401 binds specifically to CXCL1.

FIG. 1C shows immunoprecipitation followed by LC/MS-MS analysis confirmed that HL2401 binds specifically to CXCL1. That is, CXCL1 is only immunoprecipitated with HL2401 and not with the control antibody, e.g., IgG.

Amino acid sequence of the mAb variable region

Total RNA was prepared from hybridoma cells using RNA extraction kit. The synthesize cDNA using Super-Script® Ill One-Step RT-PCR System (Invitrogen™) according to the manufacturer's instructions. The cDNA was then used as the template for PCR by using set of primers designed as previously described (Yuan et al. 2004). The PCR products were purified using the Qiagen PCR clean up system (Qiagen) and ligated into pCRTM2.1 vector. The selected positive clones were sequenced using the BigDye Terminator v3.1 Cycle Sequencing kit (Applied Bio-systems). The amino acid sequences were determined from the nucleotide sequence using IMGT and designated CDRs of light and heavy chain of isolated immunoglobulin genes.

Figure 1D:
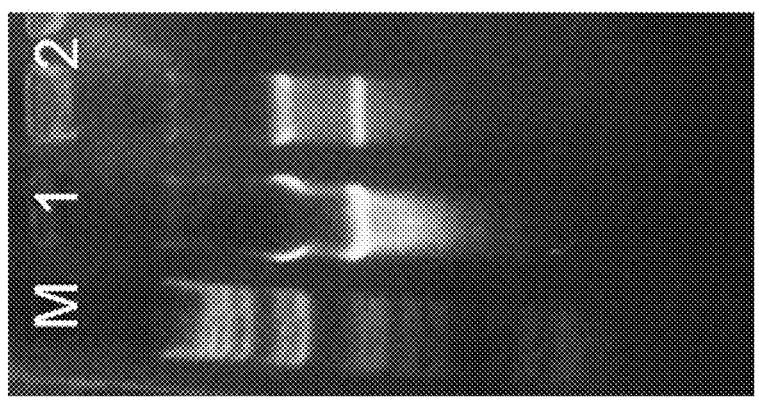
FIG. 1D shows total RNA extraction using HL2401hybridoma cell line.

FIG. 1D shows total RNA extraction using HL2401hybridoma cell line.

Figure 1E:
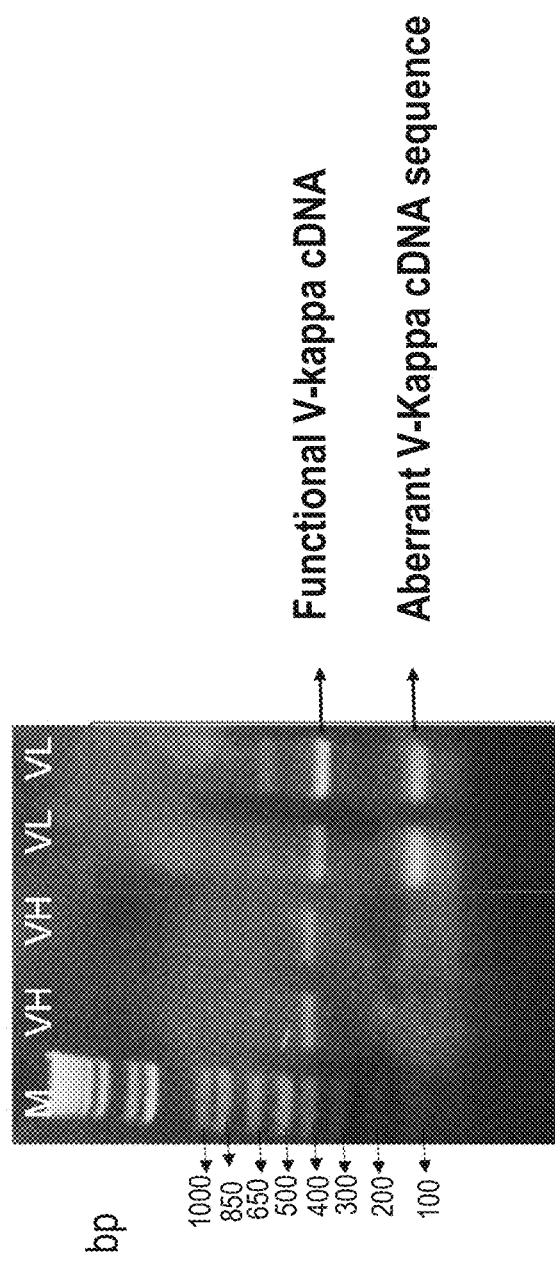
FIG. 1E shows PCR amplification using HL2401 cDNA as template.

FIG. 1E shows PCR amplification using HL2401 cDNA as template. Lane 1 and 2 indicated variable heavy chain and Lane 3 and 4 indicated variable light chain. The light chain lanes represented segments of aberrant pseudogene PCR products.

TABLE 1

Summary of CDRs denotation of HL2401 hybridoma cell

| HL2401 clone | Heavy chain (VH) | Light chain (VL) |
|---|---|---|
| CDR1 | SYYIY (SEQ ID NO: 6) | KASQSVDYDGDSYVN (SEQ ID NO: 9) |
| CDR2 | EIDPSHGGPTFN (SEQ ID NO: 7) | AASNLES (SEQ ID NO: 10) |
| CDR3 | TRESGTGAMDY (SEQ ID NO: 8) | QQSSEDPWT (SEQ ID NO: 11) |

Amino acid sequences were deduced from DNA sequences. CDRs were selected as described according to kabat numbering.

FIG. 1F shows numbering & regions the CDRs in the light chain (VL) of the HL2401 clone.

FIG. 1G shows numbering & regions the CDRs in the heavy chain (VH) of the HL2401 clone.

Classification of Variable Region Genes

Variable Region of Heavy Chain

| Result summary: | Productive IGH rearranged sequence: |
|---|---|
| V-GENE and allele | Musmus IGHV1S81*02 |
| J-GENE and allele | Musmus IGHJ4*01 F |

Variable Region of Light Chain

| Result summary: | Productive IGK rearranged sequence: |
|---|---|
| V-GENE and allele | Musmus IGKV3-4*01 F |
| J-GENE and allele | Musmus IGKJ1*01 F |

The light chain variable region of the HL2401 antibody gene belonged to the immunoglobulin mouse kappa, $V_K$III (IGKV3) subgroup and contained $J_{K1}$ gene segments.

The heavy chain belonged to the immunoglobulin mouse $V_H$ I (IGVH$_1$) subgroup gene family with $J_{H4}$ segments.

Figure 1H:
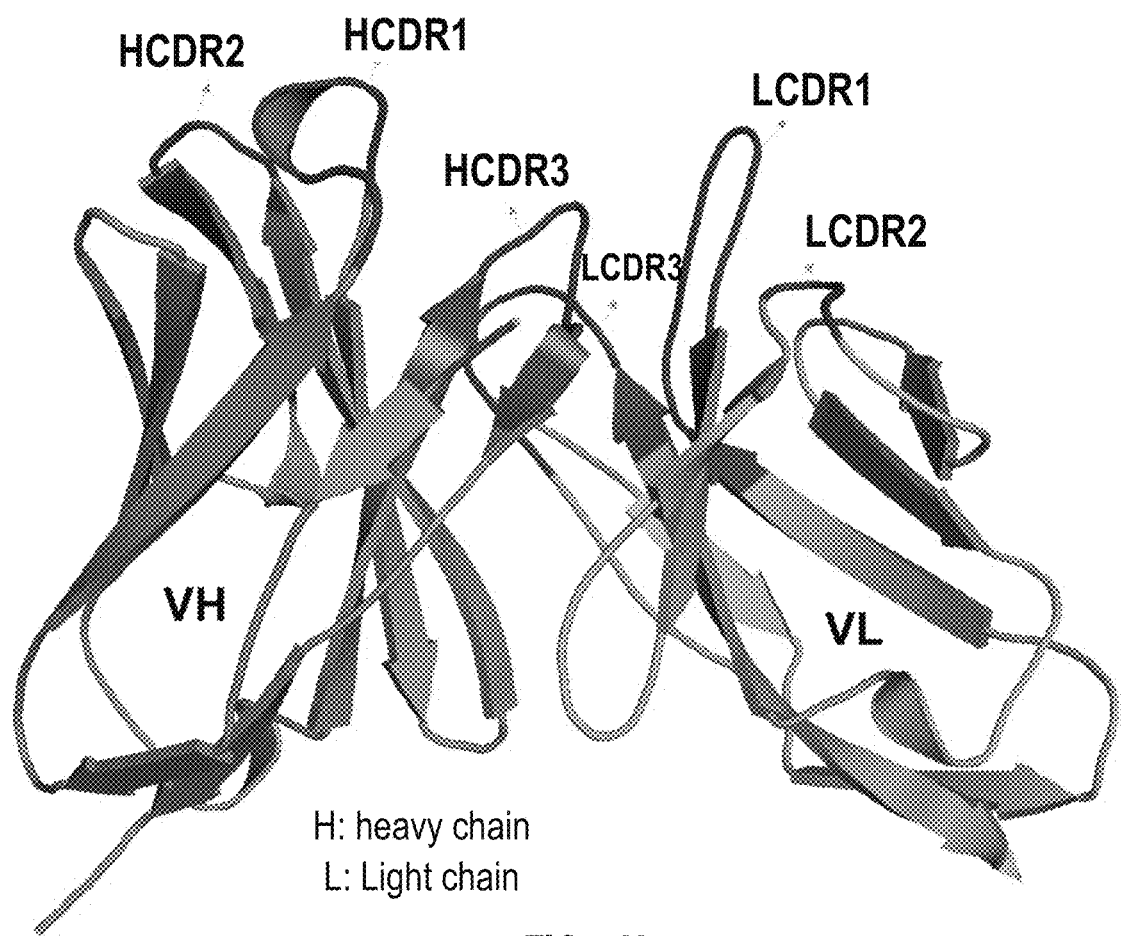
FIG. 1H shows homology modelling of mouse sequence using Rosetta homology modelling server.

FIG. 1H shows homology modelling of mouse sequence using Rosetta homology modelling server. The diagram was generated using PyMole molecular graphic system. VH represents for variable heavy chain and VL represents for variable light chain.

Construction of scFv and test biological activity against Human CXCL-1 antigen

The clone of variable heavy chain and light chain of HL2401 antibody gene were amplified using mouse primers. The amplified VH and VL domain were purified using PCR purification Kit. The resultant VH and VL fragments were overlapping using pull through PCR and amplified as scFv (Single chain Fragment variable region). The gene encoding the scFv is VH-linker-VL with a standard 20 amino acid linker (Gly4Ser) 3 GGGAR. The amplified gene was digested with BssHII and NheI restriction enzymes and insert into a pET-based vector (PAB-myc) containing a pelB promotor for controlling periplasmic protein expression (Novagen, Madison, Wis.) along with 6×histidine tag at the C-termini for purification by metal affinity chromatography and transformed into DH5α bacterial strain. The transformed clones were amplified in LB with ampicillin broth overnight. The plasmids DNA were prepared and sent for DNA sequencing. The correct sequence of scFv plasmid was transform T7 Shuffle bacterial strain and the transformed bacteria were used for soluble protein production.

Figure 1I:
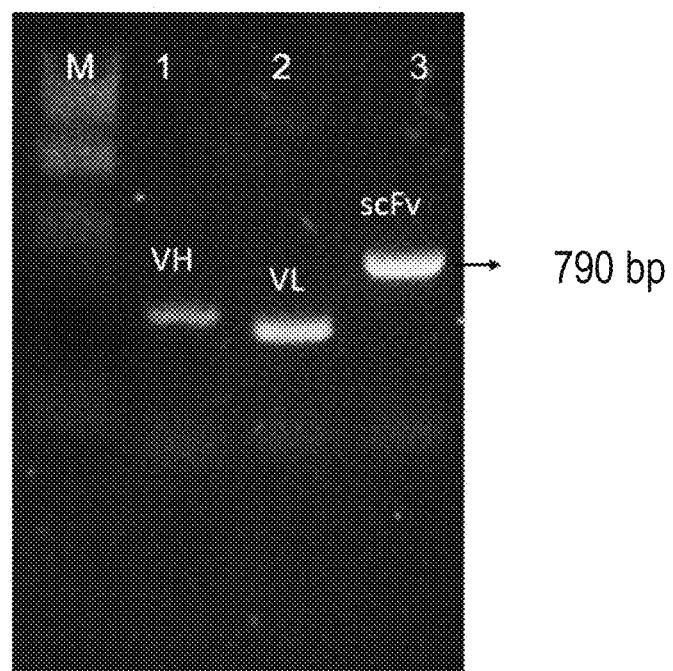
FIG. 1I shows agarose gel electrophoresis of the amplified VH, VL and scFv fragments.

FIG. 1I shows agarose gel electrophoresis of the amplified VH, VL and scFv fragments (VH: variable heavy chain; VL: variable light chain; ScFv: single chain fragment variable region).

Induction of ScFv proteins in bacterial host

The HL2401_scFv clone was transformed into T7 shuffle bacterial strain. T7 shuffle cells and was grown in 1.4 L 2×YT plus ampicillin medium at 37° C. until log-phage (OD600=0.5), induced with 0.3 mM IPTG, and allowed to grow at 30° C. for an additional 16 hrs. After induction, the bacteria were harvested by centrifugation at 8000 g for 15 min at 4° C., and the pellets were stored in −20° C. for at least 2 hrs. The frozen pellets were briefly thawed and suspended in 40 ml of lysis buffer (1 mg/ml lysozyme in PBS plus EDTA-free protease inhibitor cocktail (Thermo Scientific, Waltham, Mass.). The lysis mixture was incubated on ice for an hour, and then 10 mM MgCL2 and 1 ug/ml DNase I were added and the mixture was incubated at 25° C. for 20 min. The final lysis mixture was centrifuged at 12000 g for 20 min and the supernatants were collected. This supernatant was termed the periplasmic extract used for Nickle column affinity chromatography.

Western Blots Analysis Using HL2401 scFv Protein

Purified recombinant human CXCL1 protein was used as antigen target in Western blot analyses. 500 ng human CXCL1 protein and 1 µg purified protein as negative control were loaded onto 4-20% gradient Tris-glycine SDS-PAGE and transferred onto nitrocelluler membranes. The membrane was blocked using 3% skimmed milk in PBS for 3 h at room temperature. After that, the membrane was incubated with partial purified HL2401_scFv protein overnight at 4° C. The membrane was washed with sodium phosphate buffered saline with 0.05% tween 20 buffer (PBST) 3 times. The washed membrane was incubated with anti-c Myc mouse IgG for 1 h at room temperature to recognize the c-Myc tag on the scFv and identify the position of antigens bound by the scFv. After washing with PBST, the membrane was incubated with the goat anti-mouse IgG (H+L) HRP conjugate diluted (1:3000 v/v) in PBS for 1 h at RT, and specific immunoreactive bands were visualized with a mixture of TMB substrate.

Figure 1J:
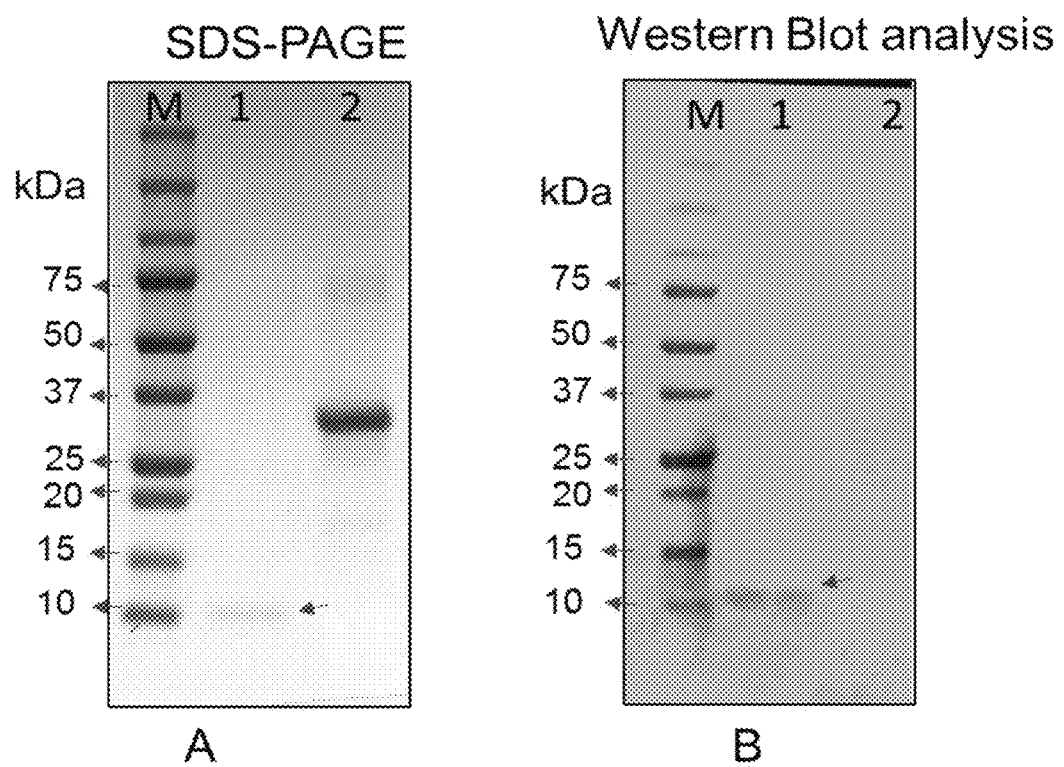
FIG. 1J shows Western blot analysis using HL2401 scFv protein.

FIG. 1J shows Western blot analysis using HL2401 scFv protein. Lane M indicates molecular weight markers. Lane 1 indicates human CXCL1 protein. Lane 2 indicates negative control.

Figure 1K:
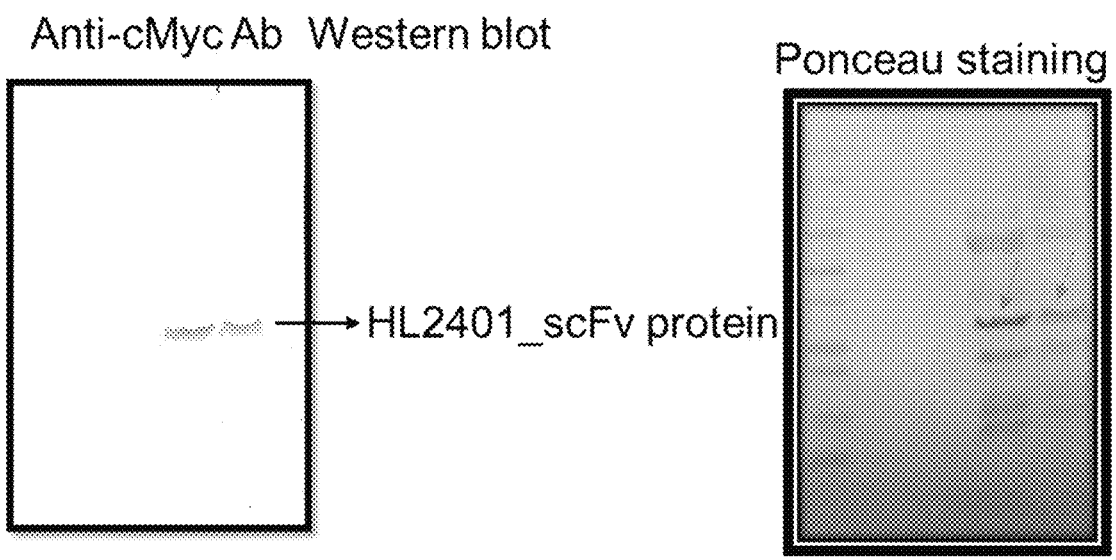
FIG. 1K anti-Myc tag monoclonal antibody.

Western blot analysis detected approximately 11 kDa band using TMB stained. In addition, this Western blot data confirmed antibody specificity to target protein. On the other hand, as shown in FIG. 1K, an anti-Myc tag monoclonal antibody was used to recognize the Myc tag on the expressed of scFv protein. The antigen loaded membrane was incubated with anti-myc-HRP (1/2000) antibody and specific immunoreactive bands were visualized with a mixture of TMB substrate. HL2401_scFv protein expressed in E. coli and partially purified that was detected by anti-cMyc antibody.

ELISA test for confirm the binding activity of HL2401_scFv protein

The human CXCL1 protein was coated onto 96-well, 30 ng for well at 4° C. overnight. The plate was blocked by 3% skim milk in PBS 2 h at room temperature. The plate was washed with PBST and applied anti-human CXCL1 scFv antibody at different dilution concentration. The anti-Myc mouse monoclonal antibody with HRP conjugate antibody was applied and developed with TMB solution.

Figure 1L:
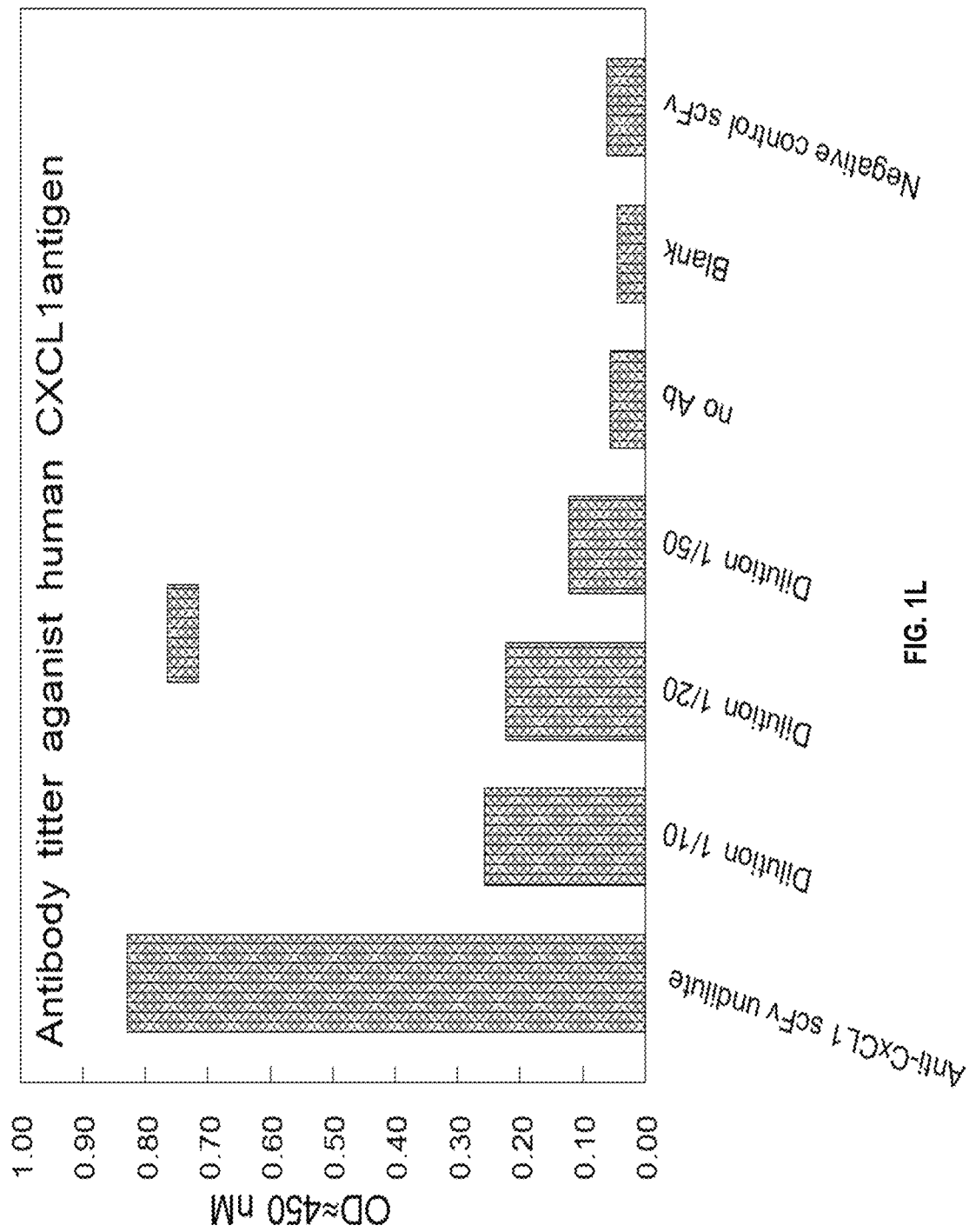
FIG. 1L shows ELISA signal that indicates HL2401_scFv protein interacting with human CXCL1 protein.

FIG. 1L shows ELISA signal that indicates HL2401_scFv protein interacting with human CXCL1 protein.

Example 2

FIGS. 2C, 2D, and 3A-3C show CXCL1 expression stimulates cell proliferation, cellular migration and invasion and endothelial tube formation.

To determine the effect of CXCL1 on key tumor cell and endothelial cell processes, human cell lines T24, DU145 and PC3 were first tested for their expression levels of CXCL1 and its receptor, CXCR2.

Figures 2A, 2B:
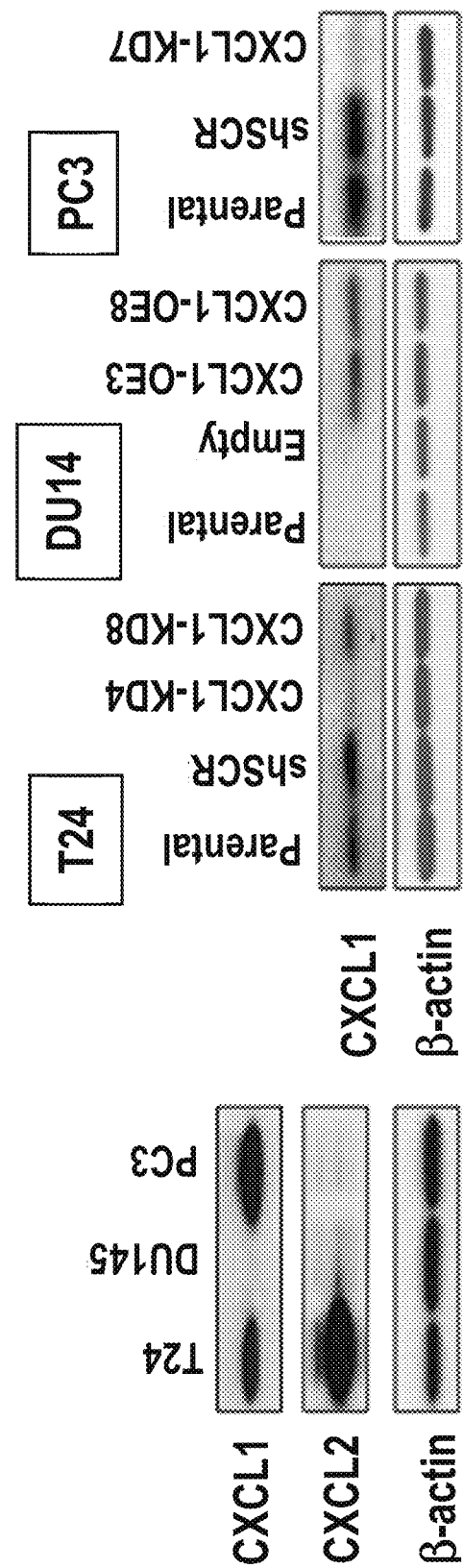
FIG. 2A shows human cell lines T24, DU145 and PC3 express a range of CXCL1 levels.
FIG. 2B shows CXCL1 protein is expressed in stably transfected cells.

FIG. 2A shows bladder cancer cell line (T24) and prostate cancer cell line (PC3) express high levels of CXCL1. On the other hand, CXCR2, the receptor for CXCL1, was highly expressed in T24 cells.

To test the effect of CXCL1 expression on cellular functions, tumor cell lines, e.g., DU145, which do not express detectable CXCL1, were stably transfected with CXCL1 to generate CXCL1-expressing tumor cells. On the other hand, tumor cell lines, e.g., T24 and PC3 cells, which highly express CXCL1, were stably transfected with CXCL1-targeting shRNA vectors to knockdown their endogenous CXCL1 expression. Plasmids with sequence verified human CXCL1 cDNA cloned within pCMV6-Empty vector and plasmid with vector alone (Origene Technologies) were transfected into DU145 cells using Fugene HD transfection reagent (Roche Diagnostics) to create DU145-CXCL1 and DU145-Empty. Similarly, CXCL1 short hairpin RNA (shRNA) cloned within pRS vector was transfected into T24 and PC3 cells as well as CXCL1 plasmid scramble (Scr) non-effective shRNA construct within pRS vector (Origene) using Fugene HD. Stable transfectants were selected with 1,200 μg/ml of G418 (Life Technologies, Inc., Carlsbad, Calif.) for DU145 clones and 0.25 μg/ml of puromycin (Life Technologies) for T24 and PC3 clones for 14 days and subcloned by limiting dilution in 96-well plates. Integration of the transfected gene into the genome was confirmed by RT-PCR. Stable cell lines were maintained in media containing 500 μg/ml of G418 for DU145 clones and in media containing 0.25 μg/ml of puromycin for T24 and PC3 clones.

FIG. 2B shows reduced CXCL1 protein expression is confirmed in cell lines stably transfected with CXCL1-targeting shRNA vectors, i.e., T24-CXCL1-KD4 and T24-CXCL1-KD8; and PC3-CXCL1-KD7. On the other hand, CXCL1 expression is confirmed in DU145 cells stably transfected with CXCL1 (DU145-CXCL1-OE3 and DU145-CXCL1-OE8).

To determine the effect of CXCL1 on tumor cell migration or invasion, an in vitro migration and invasion assay was performed. Migration assays were performed in 6 well two-tier invasion chambers (Collaborative Biomedical Products, Bedford, Mass., USA) (Gomes Giacoia et al, 2014). Polycarbonate membranes were coated with 4 mg/mL growth factor reduced Matrigel (BD Biosciences, San Jose, Calif.) as described for invasion assays, control inserts (migration only) contained no coating. Two separate experimental designs were tested. First, DU145-CXCL1-OE3 and DU145-CXCL1-OE 8, DU145-Empty, T24-CXCL1-KD4 and T24-CXCL1-KD8, T24-shSCR, PC3-CXCL1-KD7, and PC3-shSCR cells were added to each insert at a density of $10^5$ cells/ml/well in RPMI media. The lower chamber contained RPMI media with 10% FBS as a chemoattractant. The cells were maintained in a humidified incubator in 5% $CO_2$ at 37° C. for 24 hours. After the designated time, the cells on the top of the polycarbonate membrane were removed. The cells attached to the bottom of the membrane were stained for 1 hour with cell viability indicator Calcein AM Fluorescent Dye (BD Biosciences, Franklin Lakes, N.J.) and quantified using the FLUOstar OPTIMA at 495 mm excitation and 515 nm emission (BMG LABTECH Inc., Cary, N.C.).

Figure 2C:
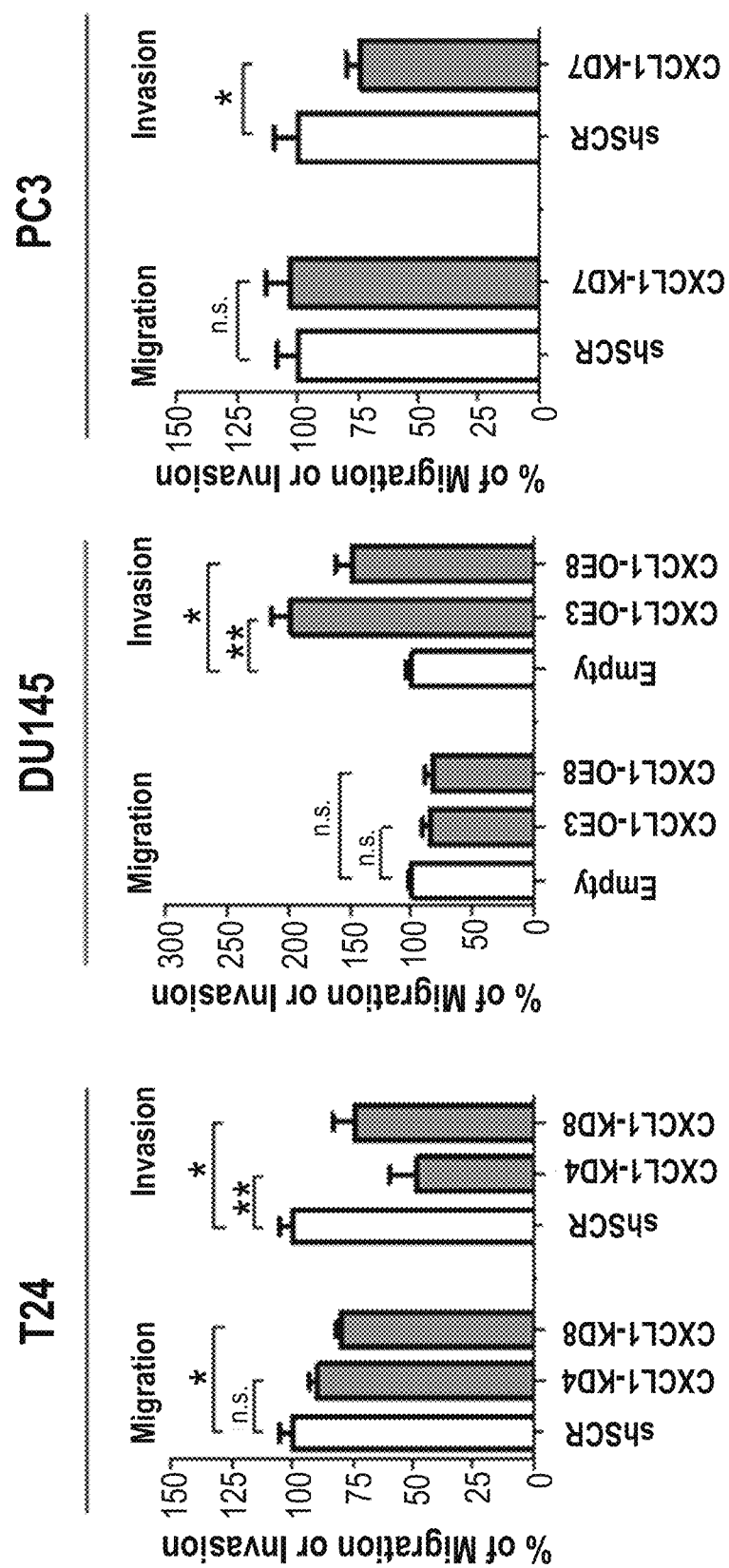
FIG. 2C shows, in an in vitro migration and invasion assay, the migratory potential of stably transfected cells.

FIG. 2C shows, in an in vitro migration and invasion assay, the migratory potential of DU145-CXCL1-OE3 and DU145-CXCL1-OE8 clones was not enhanced compared to the DU145-Empty control. However, the invasive potential of DU145-CXCL1-OE3 and DU145-CXCL1-OE8 clones was significantly enhanced by at least 50% compared to DU145-Empty (p<0.01). Similarly, the migratory potential of PC3-CXCL1-KD7 cells was not reduced compared to PC3-shSCR, but the invasive potential was significantly reduced by 27% in PC3-CXCL1-KD7 compared to PC3-shSCR (p<0.01). The same phenomenon was also observed in the migration and invasion assays of T24 clones. Specifically, T24-CXCL1-KD8 cells (p<0.01) but not T24-CXCL1-KD4 cells showed an inhibition in cell migration, however both T24-CXCL1-KD4 and T24-CXCL1-KD8 clones demonstrated a significant inhibition (at least 25%) of invasive potential compared to T24-shSCR (p<0.01). These results suggest that CXCL1 expression may play an important role in tumor cell invasion and, possibly, tumor cell migration.

To test the effect of CXCL1 on endothelial cell behaviour, a capillary tube formation assay was performed. Human umbilical vein endothelial cell (HUVEC) tube formation assay is one of the most widely used in vitro model in angiogenesis research. HUVEC cells express CXCR2 and undergo cell proliferation and sprouting in response to CXCL1 stimulation. Briefly, Matrigel (BD Biosciences) was added to 96-well plates (50 μl per well) and allowed to solidify for 30 min at 37° C. HUVEC cells were incubated in serum- and growth factor-free EBM2 basal media containing 0.1% delipidated BSA for 5 hrs. HUVECs were seeded on top of Matrigel in triplicates at a density of $10^4$ cells per well in conditioned media and incubated for 6 hrs.

Images were acquired with a Nikon ECLIPS E400 microscope (Nikon, Melville, N.Y.). The total length of tube-like structures in at least 4 viewed fields per well was measured using ImageJ. At least three independent experiments consisting of each condition tested in triplicate wells was used to calculate mean±SD values.

Figure 2D:
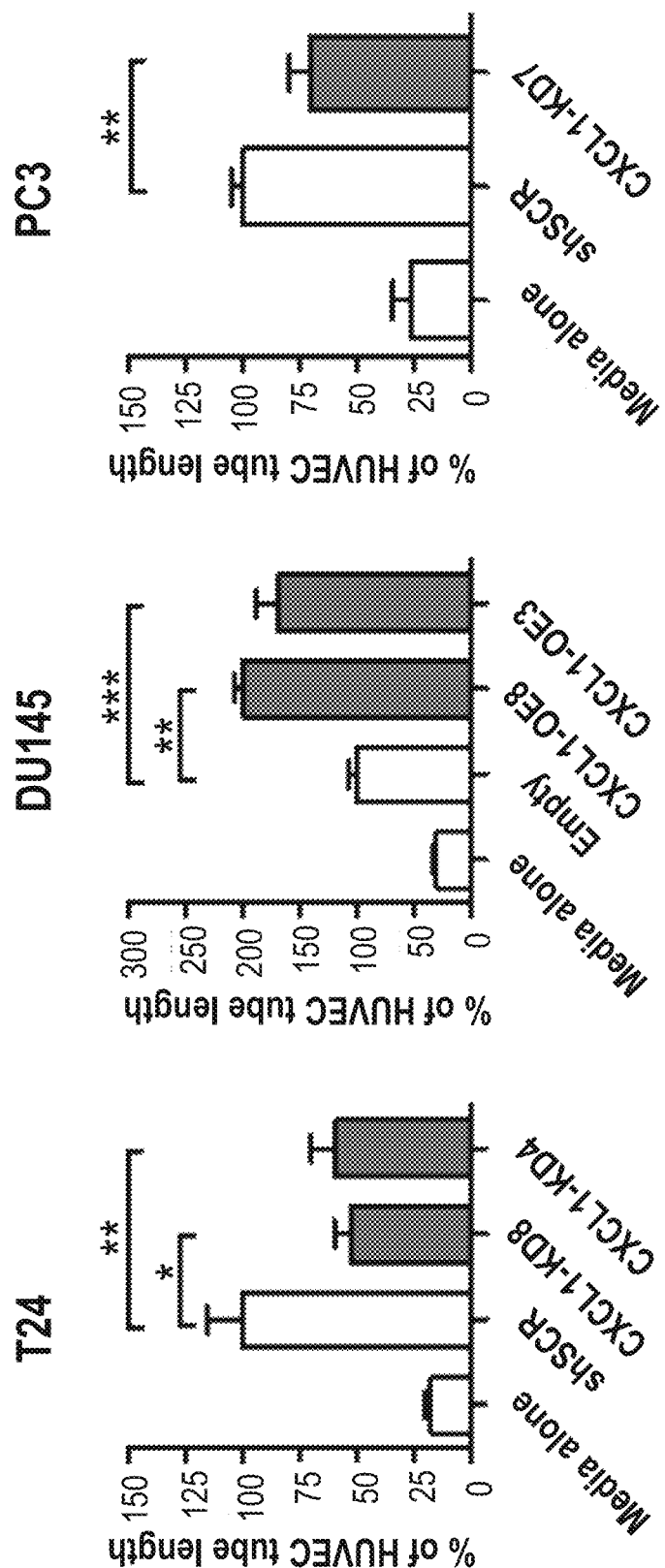
FIG. 2D shows, in a tube-formation assay, the total length of structures formed by Human umbilical vein endothelial cells (HUVEC) affected by stably transfected cells.

HUVEC cultures were treated with conditioned media from the cell lines shown in FIG. 2B. FIG. 2D shows, in a tube-formation assay, the total length of structures formed by HUVECs on growth factor reduced Matrigel was significantly enhanced (~60%) when treated with media from DU145-CXCL1-OE3 and DU145-CXCL1-OE8 clones. In contrast, the total length of tube-like structures was significantly reduced when treated with conditioned media from CXCL1-knockdown T24 (T24-CXCL1-KD4 and T24-CXCL1-KD8) and PC3 (PC3-CXCL1-KD7) cells (~50% and ~28%, respectively). These results suggest that CXCL1 may promote angiogenesis by inducing endothelial cell tube formation.

Example 3

Targeting CXCL1 Inhibits Proliferation, Cellular Invasion and Endothelial Tube Formation To test whether CXCL1 inhibitors, such as anti-CXCL1 neutralizing monoclonal mouse antibody (HL2401), could affect proliferation, a cell proliferation assay was performed. Briefly, $10^3$ cells (T24, DU145, and PC3) per well were plated in 96-microwell plates and incubated for 6, 24, 48 and 72 hours with the indicated concentration of HL2401 for 72 hrs. Each condition was tested in triplicate wells. Cell proliferation was determined by incorporation of 3-(4,5-dimethylthiazol-2-yl)-2,5-diphenyltetrazolium bromide (MTT). At least three independent experiments were performed in triplicate.

Figure 3A:
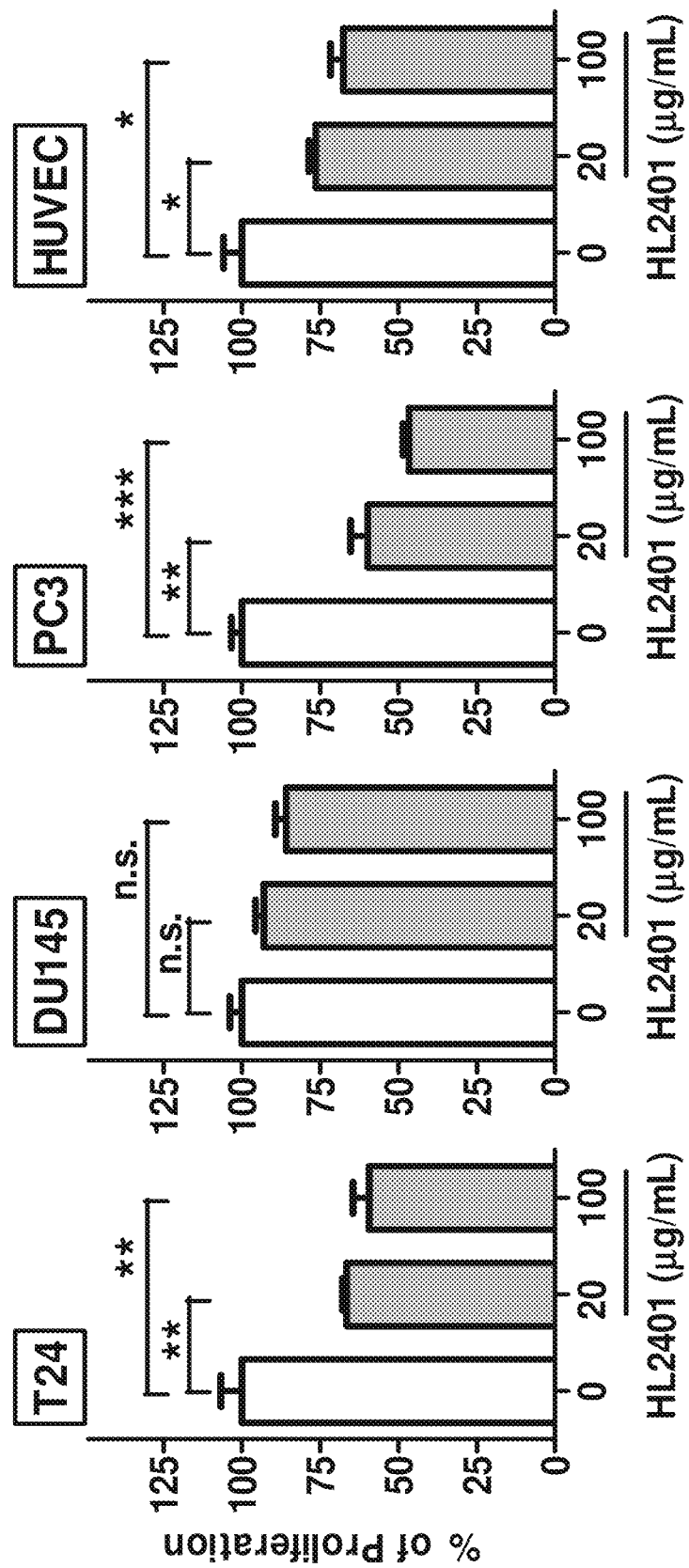
FIG. 3A shows, in an in vitro proliferation assay, the effect of HL2401 on proliferation of human cells.

FIG. 3A shows, in an in vitro proliferation assay at 72 hours, proliferation of T24, PC3, and HUVEC cell lines, but not DU145 cells, were significantly inhibited by HL2401 (20 and 100 µg/mL). The anti-CXCL1 mAb can completely block CXCL1-induced HUVEC proliferation and sprouting.

To test whether anti-CXCL1 neutralizing monoclonal mouse antibody (HL2401) could affect tumor cell invasion, T24, DU145 and PC3 cells ($10^5$ cells/mL/well) were exposed to 0-200 µg/ml of CXCL1 monoclonal antibody (HL2401) in RPMI media. The lower chamber contained RPMI media with 10% FBS as chemoattractant. After 24 hours, the T24, DU145 and PC3 cells on the top of the polycarbonate membrane were removed, while T24, DU145 and PC3 cells attached to the bottom of the membrane were stained for 1 hour with cell viability indicator Calcein AM Fluorscent Dye and quantified using the FLUOstar OPTIMA. For the migration and invasion assays, at least three independent experiments consisting of each condition tested in triplicate wells was used to calculate mean±SD values.

Figure 3B:
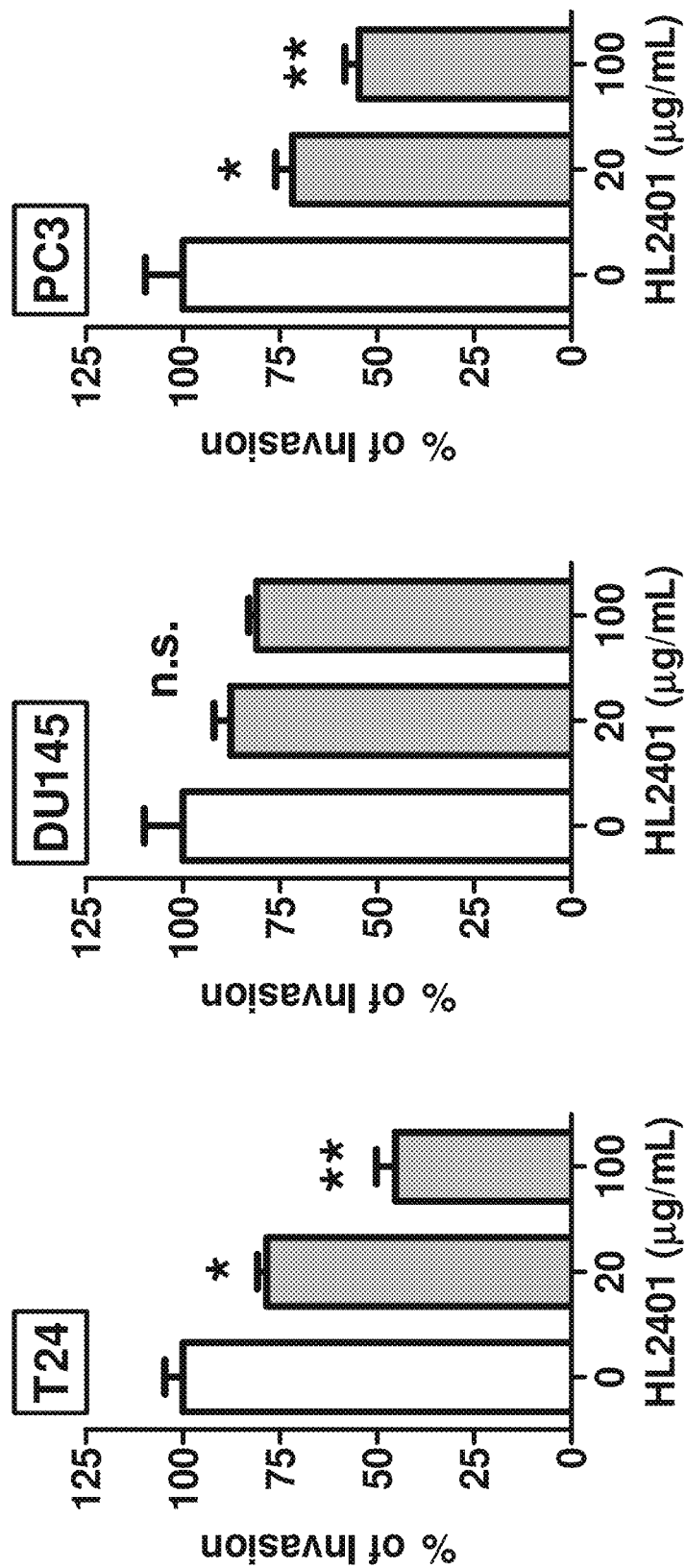
FIG. 3B shows, in an in vitro invasion assay, the effect of HL2401 on the invasive potential of human cell lines.

FIG. 3B shows, in an in vitro invasion assay, the invasive potential of T24 and PC3 was significantly reduced with the addition of HL2401 (20 µg/mL) (p<0.01). DU145 invasive potential was unchanged by the addition of HL2401. These results suggest CXCL1 inhibitors, such as HL2401, can inhibit invasion of tumor cells that express CXCL1.

To demonstrate anti-angiogenic effects of this anti-CXCL1 antibody, the antibody was evaluated in an in vitro HUVEC tube formation assay. Briefly, HUVEC cells were seeded into 96-well plates coated with Matrigel. After 30 minutes, cells previously fed with serum and growth factor free EBM2 basal medium for 5 hours were plated with the above media supplemented with 0, 20 or 100 ug/ml of CXCL1 mAb (HL2401). After 6 hours, photographic images of each well were obtained. Images were acquired with a Nikon ECLIPS E400 microscope (Nikon, Melville, N.Y.). The total lengths of the tube structures were recorded. The total length of tube-like structures in at least 4 viewed fields per well was measured using ImageJ. At least three independent experiments consisting of each condition tested in triplicate wells was used to calculate mean±SD values.

Figure 3C:
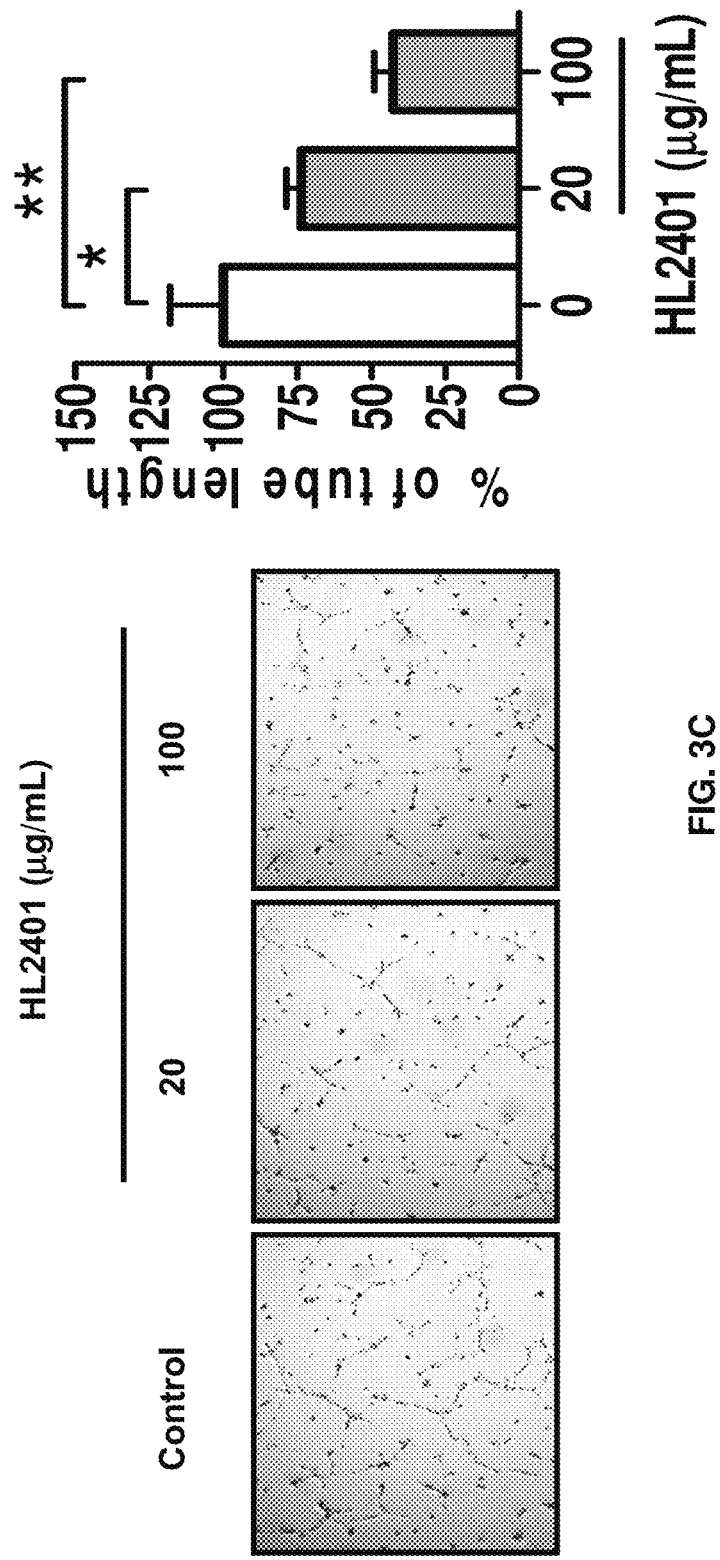
FIG. 3C shows the effect of HL2401 on HUVEC tube length.

FIG. 3C shows that in the wells that contain 20 µg/ml of anti-CXCL1 mAb (HL2401), HUVEC tube length was significantly reduced and all sprouting was inhibited at 100 µg/ml. In contrast, in the control wells in which the same amount (1 µg/ml) of normal antibody was added, no inhibitory effect on HUVEC tube formation was observed. Hence, the anti-CXCL1 antibody of the present disclosure can completely inhibit vascular endothelial cell proliferation and sprouting; thus, this antibody is capable of blocking angiogenesis. In a further study, it was shown that the HL2401 antibody does not bind to mouse CXCL1. Therefore, it is not suitable to assess the biological activity of this antibody in regular mouse in vivo models.

Example 4

Pharmacokinetic Studies and Bio-Distribution

To determine the effect on HL2401 by in vivo administration, pharmacokinetics studies were performed in female C57BL/6 mice to determine plasma exposure to CXCL1 antibody after single administration. CXCL1 antibody was radiolabeled. Briefly, $^{64}$Cu was produced with an onsite cyclotron (GE PETrace). $^{64}$CuCl$_2$ (74 MBq) was diluted in 300 µL of 0.1 M sodium acetate buffer (pH 5.5) and mixed with 200 µL of NOTA-CXCL1 antibody (0.5 mg/mL). The reaction was conducted at 37° C. for 45 min with constant shaking. The resulting $^{64}$Cu-NOTA-CXCL1 antibody was purified by PD-10 size exclusion column chromatography, using PBS as the mobile phase. The radioactive fraction containing $^{64}$Cu-NOTA-CXCL1 antibody was collected for in vivo studies.

Plasma samples at the following time points post-injection were taken: time zero (no treatment), 12, 24 and 48 hours. Plasma was derived from the whole blood by centrifugation at 3,000 rpm at 4° C. in plasma separator tubes for 10 minutes. All samples were stored at −80° C. until subsequent analysis. Samples were analyzed for CXCL1 antibody using an indirect ELISA. The lower limit of quantifications was 0.94 ng/mL in plasma. Pharamcokinetics parameters were calculated using noncompartmental analysis in WinNonLin v 5.0.3.

At different time points post-injection (p.i.) of 5-10 MBq of 64Cu-NOTA-CXCL1 antibody via tail vein, PET scans of ICR mice (Envigo, Indianapolis, Ind.; n=4) were carried out using a microPET/microCT Inveon rodent model scanner (Siemens Medical Solutions USA, Inc.). Data acquisition, image reconstruction, and region-of-interest (ROI) analysis of the PET data were performed. Briefly, the images were acquired by 40 million-count static PET scans and reconstructed using maximum a posteriori (MAP) algorithm, without attenuation or scatter correction. ROI analysis of each PET scan was carried out using software (Inveon Research Workplace, IRW) based on decay-corrected whole-body images, calculated with the injected dose measured by a dose calibrator (Capintec, Inc., Ramsey, N.J.). Quantitative PET data of the tumor and major organs was presented in the format of percentage injected dose per gram of tissue (% ID/g). After the last scan at 48 h p.i., biodistribution studies were performed to corroborate PET data. Mice were euthanized and blood and major organs/tissues were collected and wet-weighed. The radioactivity in the tissue was measured using a γ counter (Perkin-Elmer, Norwalk, Conn.) and presented as % ID/g (mean±SD).

Figure 4B:
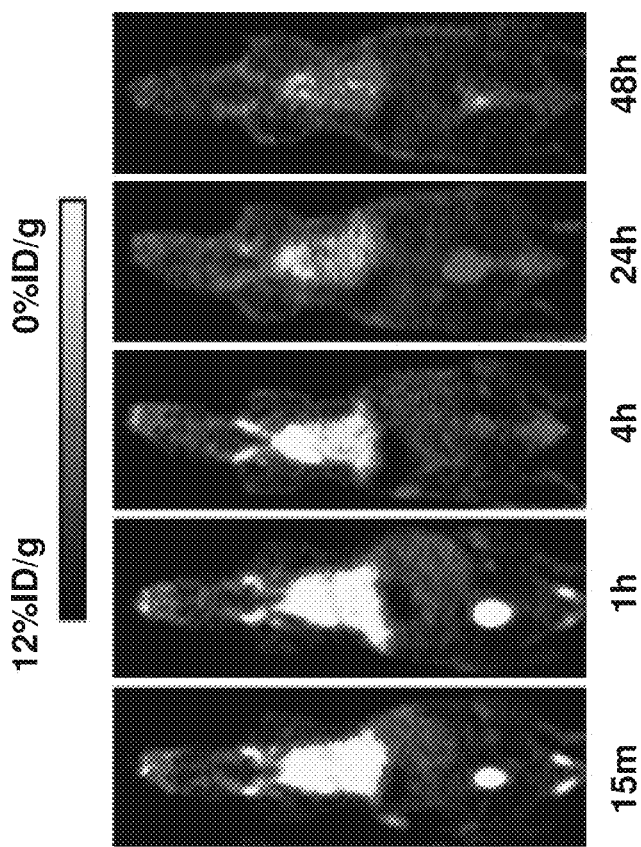
FIGS. 4B and 4C show, after a single injection of HL2401, the radiolabeled HL2401 antibody was rapidly distributed.
Figure 4A:
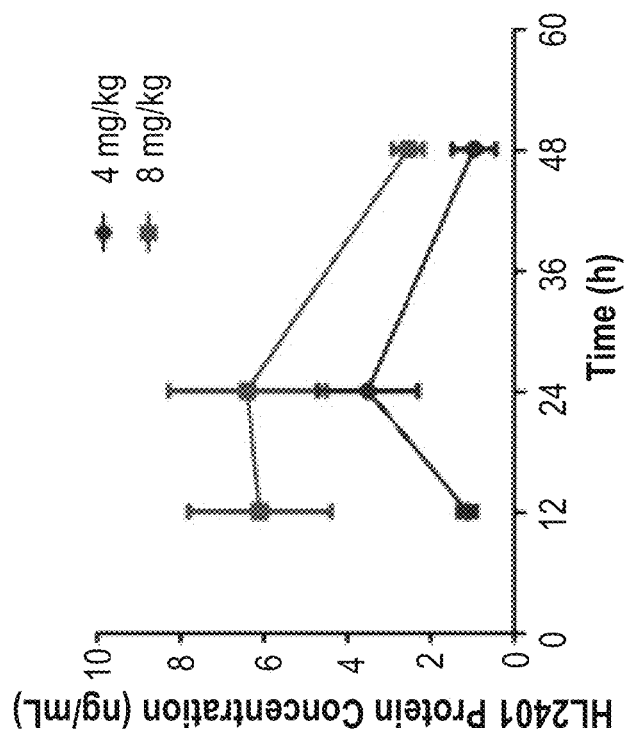
FIG. 4A shows, following intraperitoneal administration, the plasma concentration of HL2401.

FIG. 4A shows, following intraperitoneal administration, the plasma concentration of HL2401 declined rapidly, due to rapid distribution to peripheral components. Limitations of assay sensitivity prevented characterization of terminal elimination (i.e., excretion). Concentration time analysis of HL2401 in plasma after a single dose of 4 mg/kg or 8 mg/kg was 22.89 ng/g and 46.71 ng/g ($C_{max}$), 2.49 hours and 2.71 hours ($t_{1/2}$) and 0.046 units and 0.044 units (clearance), respectively.

Figure 4D:
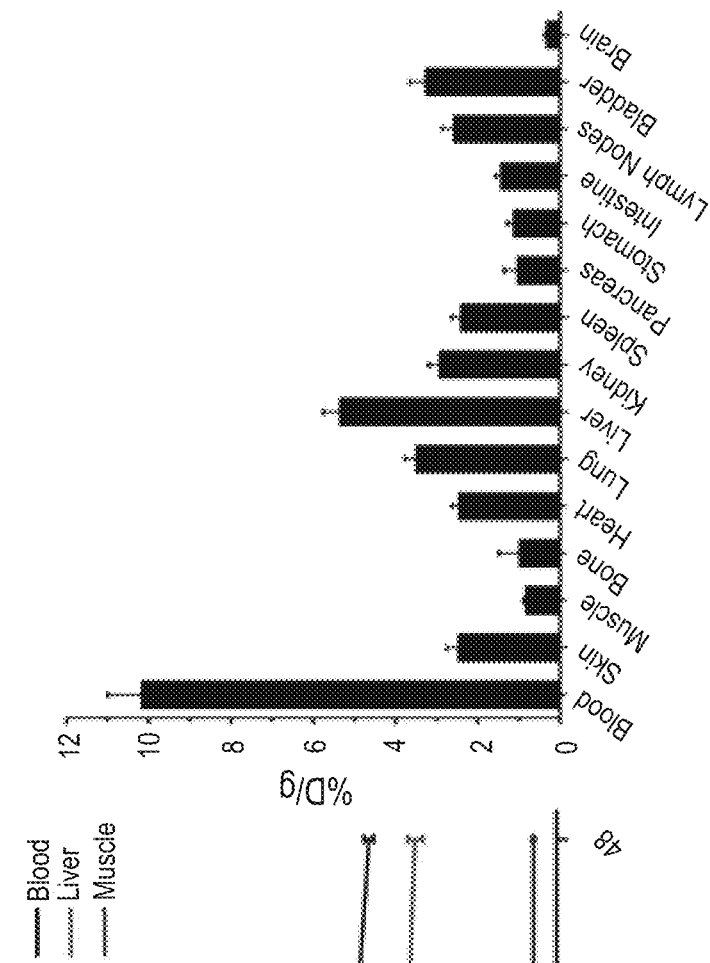
FIG. 4D shows the ex vivo bio-distribution data.
Figure 4C:
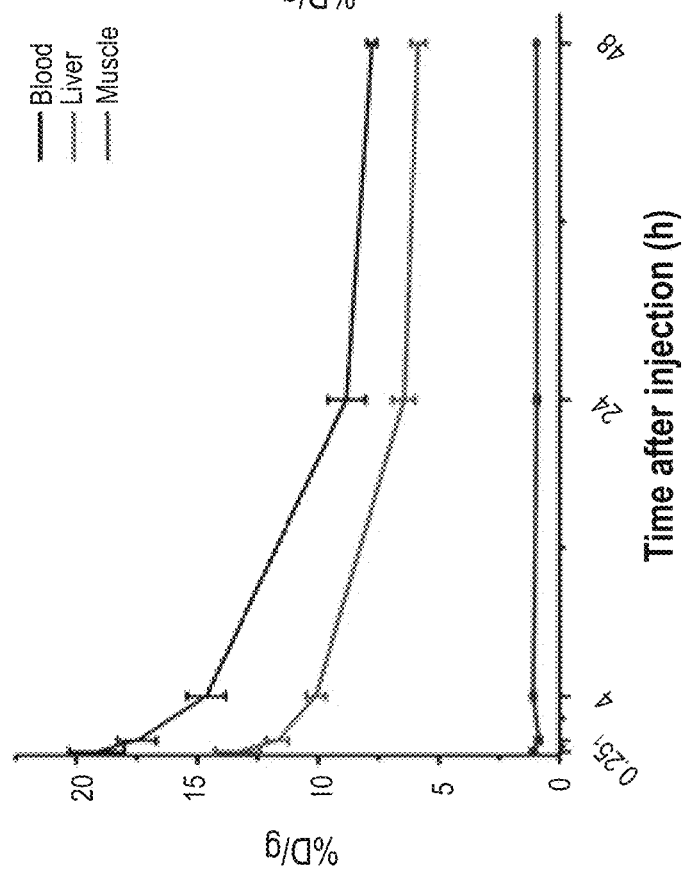

Similarly, FIGS. 4B and 4C show, after a single injection of 0.5 mg/kg, the radiolabeled antibody was rapidly distributed, remaining above the limits of detection for over 48 hours on PET imaging ($C_{max}$=19.15% D/g at 15 min, $t_{1/2\alpha} \approx 3.5$ min, $t_{1/2\beta} \approx 44.0$ hours).

FIG. 4D shows the ex vivo bio-distribution data that is well matched with the imaging results, thus, confirming the accuracy of PET imaging.

Example 5

Inhibition of Tumor Growth by HL2401 in Xenograft Model

The importance of CXCL1 expression for tumorigenicity and angiogenesis was assessed in vivo using bladder cancer (T24) and prostate cancer (PC3) mouse xenograft models. DU145 xenografts were not generated because DU145 cells do not express CXCL1 or CXCR2. As such, HL2401 may generate minimal therapeutic response in DU145 xenografts. To determine whether targeting CXCL1 with a monoclonal antibody could inhibit xenograft tumor growth, CXCL1 antibody HL2401 was administered In vivo. Animal care was in compliance with the recommendations of The Guide for Care and Use of Laboratory Animals (National Research Council) and approved by University of Hawaii local IACUC. Subcutaneous tumorigenicity assay was performed in athymic BALB/c nu/nu male mice (6 to 8 weeks old) purchased from Envigo by inoculating 2×10⁶ parental T24 cells and 2×10⁶ parental PC3 cells, as described previously (Miyake et al, 2015; Sakai et al, 2009b). After one week, mice bearing subcutaneously xenograft tumors were divided randomly into three groups (Control, 4 mg/kg or 8 mg/kg) of HL2401 and treatment was initiated. Each group contains at least 10 mice. No toxicity or weight loss was noted in any of the treatment groups. HL2401 (100 μl diluted in sterile PBS) was administered via intraperitoneal injection twice weekly for four weeks. Control mice received IgG alone on the same schedule. Tumor volumes were measured weekly with digital calipers and calculated by V (mm³)=length×(width)²×0.5236. After five weeks of cell inoculation, the mice were sacrificed, tumors resected and analyzed by immunohistochemical staining.

Figure 5A:
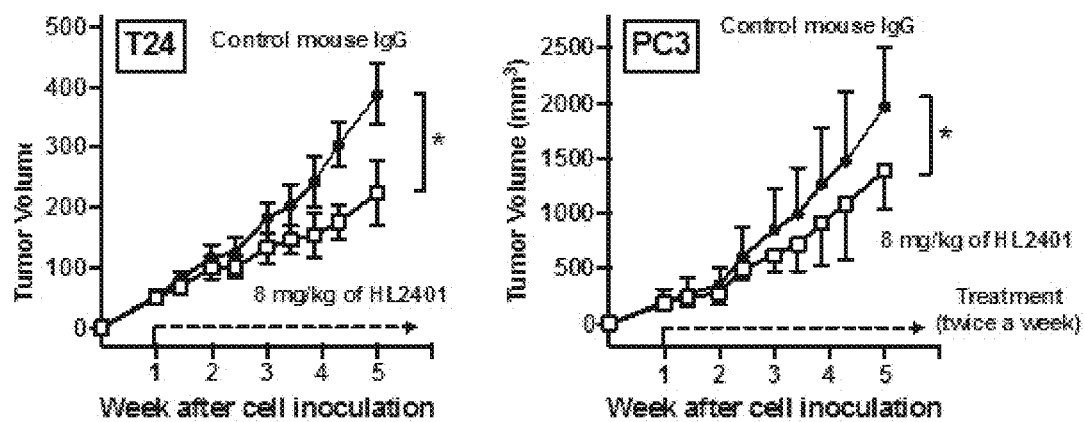
FIG. 5A shows no toxicity with HL2401 administration.

FIG. 5A shows no toxicity (i.e., no weight change or activity change) in mice treated with HL2401 (8 mg/kg). At the end of 5 wk endpoint of an in vivo study, control T24 xenografts reached an average of 388 mm³ in size. T24 xenografts treated twice weekly with 4 mg/kg of HL2401 reached 274 mm³ (p=0.22) and only 224 mm³ when treated with 8 mg/kg (p<0.05). Similarly, PC3 tumors in mice treated with 4 mg/kg and 8 mg/kg of HL2401 were reduced (p=0.15 and p<0.05, respectively) in size at the experimental endpoint (only 8 mg/kg of HL2401 data shown).

Figure 5B:
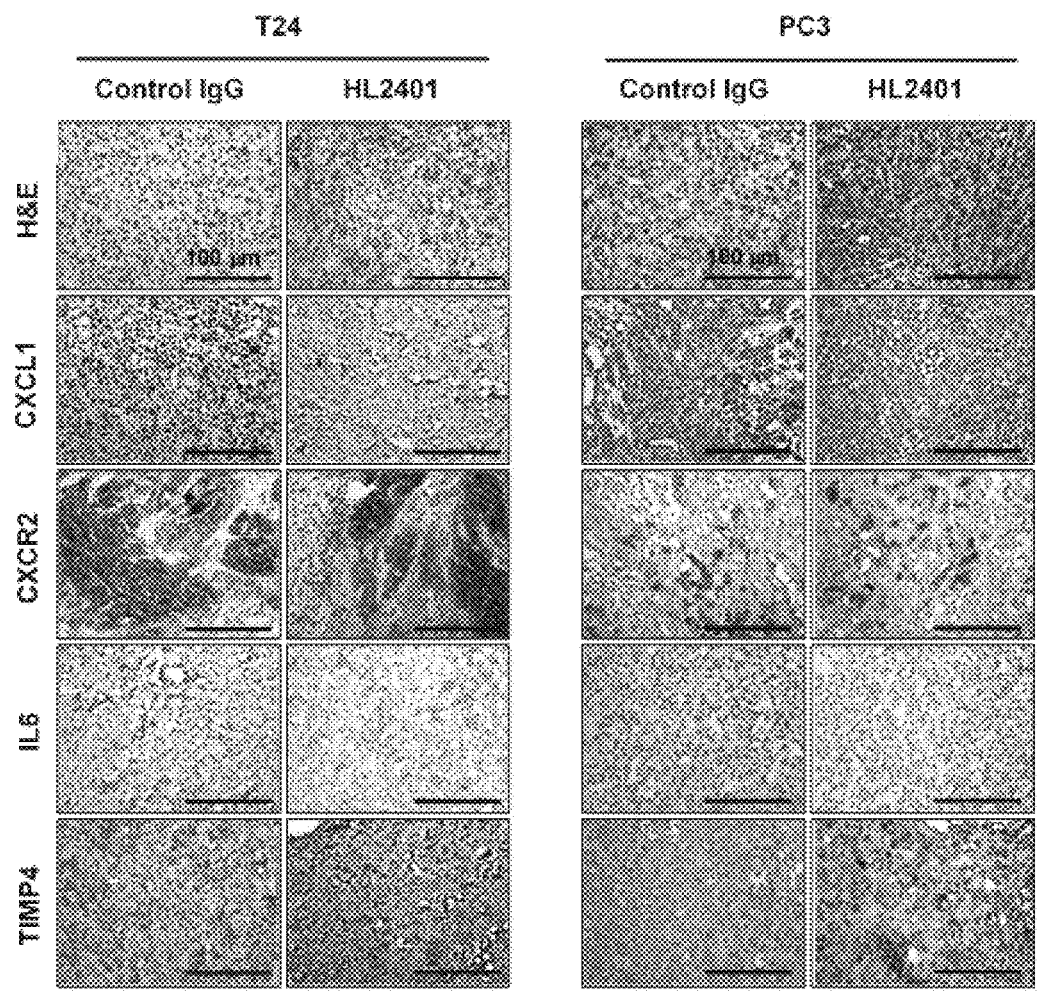
FIG. 5B shows immunofluorescent staining on the T24 and PC3 xenograft tumors for CXCL1.

FIG. 5B shows immunofluorescent staining on the T24 and PC3 xenograft tumors for CXCL1 and PECAM-1 to indicate the location of CXCL1. In both T24 and PC3 xenografts, CXCL1 was expressed in the tumor cells in addition to the tumor-associated endothelial cells. IHC analysis of excised xenografts revealed a reduction in CXCL1 expression when treated with 8 mg/kg of HL2401. CXCR2 expression was more prevalent in T24 xenografts compared to PC3 xenografts and CXCR2 expression levels in these tumors treated with HL2401. Furthermore, a reduction of interleukin 6 (IL-6) and an increase in metalloproteinase inhibitor 4 (TIMP4) are shown in both T24 and PC3 tumors from animals treated with 8 mg/kg of HL2401. This result is consistent with the data of an angiogenesis PCR array, in which 84 targets was queried from two independent experiments and significant fold change deviations were recorded. Table 2 shows IL-6 is among the genes that were noted to consistently correlate with CXCL1 expression, others include Jagged 1 protein (JAG1) and Chondromodulin-1 (LECT1). A Tumor Metastasis PCR array containing 84 targets was also queried from two independent experiments and significant fold change deviations (p<0.05) were recorded. Table 2 shows TIMP4 is among the genes that were noted to consistently correlate with CXCL1 expression, others include Insulin-like growth factor 1 (IGF1) and Matrix metalloproteinase 2 (MMP2).

TABLE 2

Fold change angiogenesis- or metastasis-related genes in PCR arrays

| PCR array | Genes | T24(vs. shSCR) CXCL1 KD4 | DU145 (vs. Empty) CXCL1 OE8 | PC3 (vs. shSCR) CXCL1 KD7 |
|---|---|---|---|---|
| Angiogenesis array (PAHS-024Z) | Interleukin 6 (IL6) | 0.41 ± 0.08 | 3.2 ± 0.19 | 0.52 ± 0.05 |
| | Jagged 1 protein (JAG1) | 0.49 ± 0.11 | 3.4 ± 0.16 | 0.61 ± 0.09 |
| | Chondromodulin-1 (LECT1) † | 6.13 ± 0.24 | 1.23 ± 0.19 | 3.94 ± 0.18 |
| Tumor Metastasis array (PAHS-028Z) | Insulin-like growth factor 1 (IGF1) | 0.49 ± 0.07 | 2.6 ± 0.29 | 0.59 ± 0.11 |
| | matrix metalloproteinase 2 (MMP2) | 0.04 ± 0.02 | 1.0 ± 0.16 | 0.45 ± 0.11 |
| | Metalloproteinase inhibitor 4 (TIMP4) ‡ | 2.11 ± 0.21 | 0.22 ± 0.04 | 1.52 ± 0.30 |

† Anti-angiogenic factor
‡ inhibitor of tumor invasion

This mechanistic finding of this study is that CXCL1 induces angiogenesis and invasion by regulating IL-6 and TIMP4, respectively. TIMP4 is a member of the tissue inhibitors of metalloproteinases (MMPs) family, which is comprised of four members (TIMP1-4) with high sequence homology and structural identity, but with different tissue expression, regulation and inhibitory characteristics. The TIMPs regulate such diverse processes as extracellular matrix (ECM) remodeling, and growth factors and their receptors' activities through the inhibition of MMPs. Numerous tumors, including bladder and prostate, have been noted to have lower levels of TIMP4 (Melendez-Zajgla et al, 2008). IL-6 is a multifunctional pro-inflammatory cytokine that functions in inflammation and the maturation of B cells. IL-6 expression and function are altered in inflammatory-associated disease states (e.g., arthritis) as well as in several human cancers, including prostate (Culig, 2014) and bladder cancer (Chen et al, 2013). Binding of IL-6 to its membrane receptor is followed by initiation of signal transduction through one of several pathways: JAK/STAT, MAPK and/or PI3K pathways. In addition to regulation through its membrane receptor, IL-6 also acts through trans-signaling in regulation of proliferation, migration, and invasion (Santer et al, 2010). Thus, these results suggest that CXCL1 influences tumor growth through a) the induction of IL-6, which leads to enhancement of cellular proliferation, migration and invasion and b) the inhibition of TIMP4 may facilitate the activation of MMPs further enabling cellular growth and motility, while therapeutically targeting CXCL1 inhibits these molecules and halts these processes.

The apoptotic index in xenografts was evaluated using cleaved caspase-3 immunostaining. Analyses revealed a significant increase in cleaved caspase-3 (indication of apoptosis) in both T24 and PC3 xenografts treated with 8 mg/kg of HL2401.

Figure 6A:
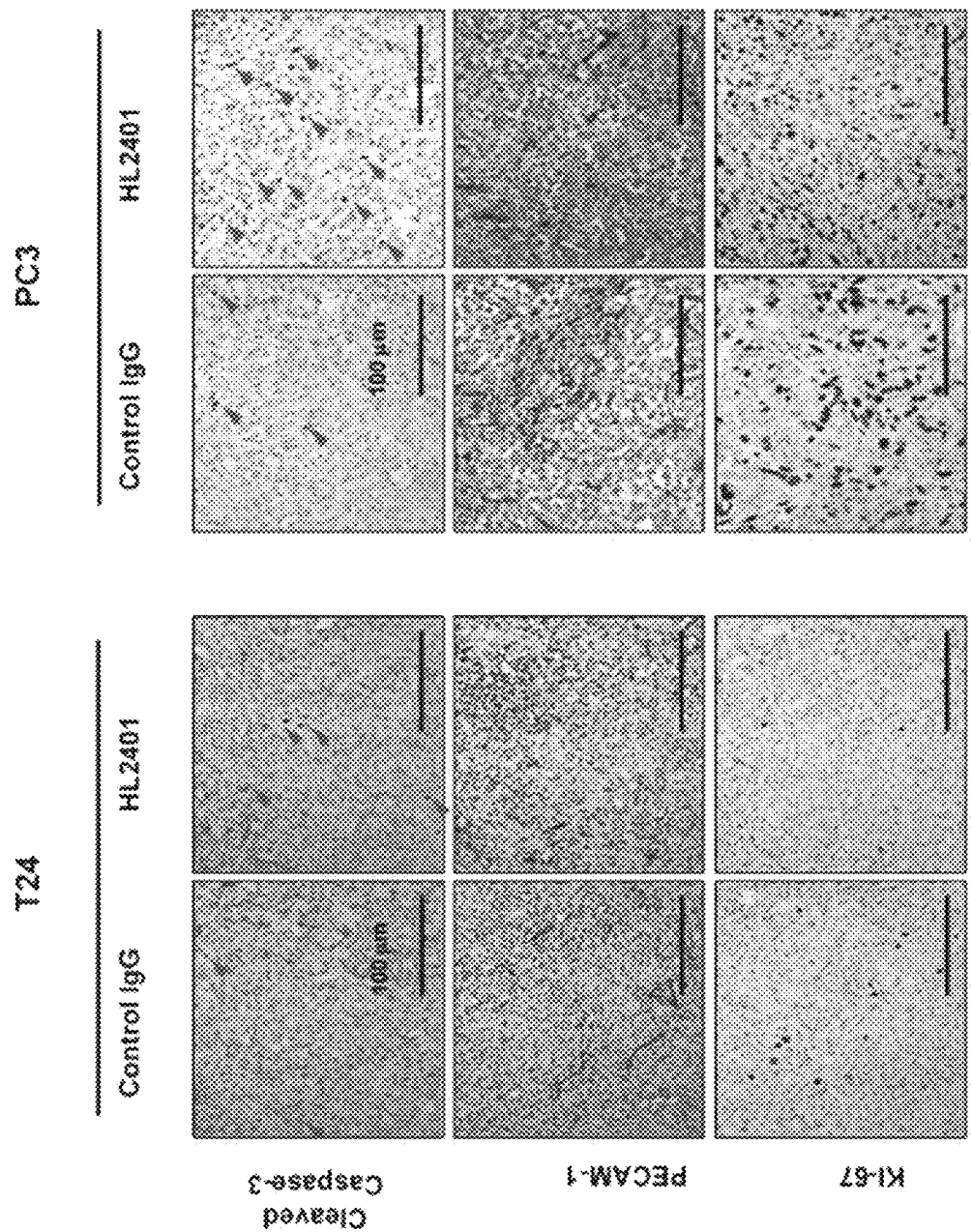
FIGS. 6A and 6B show apoptotic index in tumors from animals treated with HL2401.
Figure 6B:
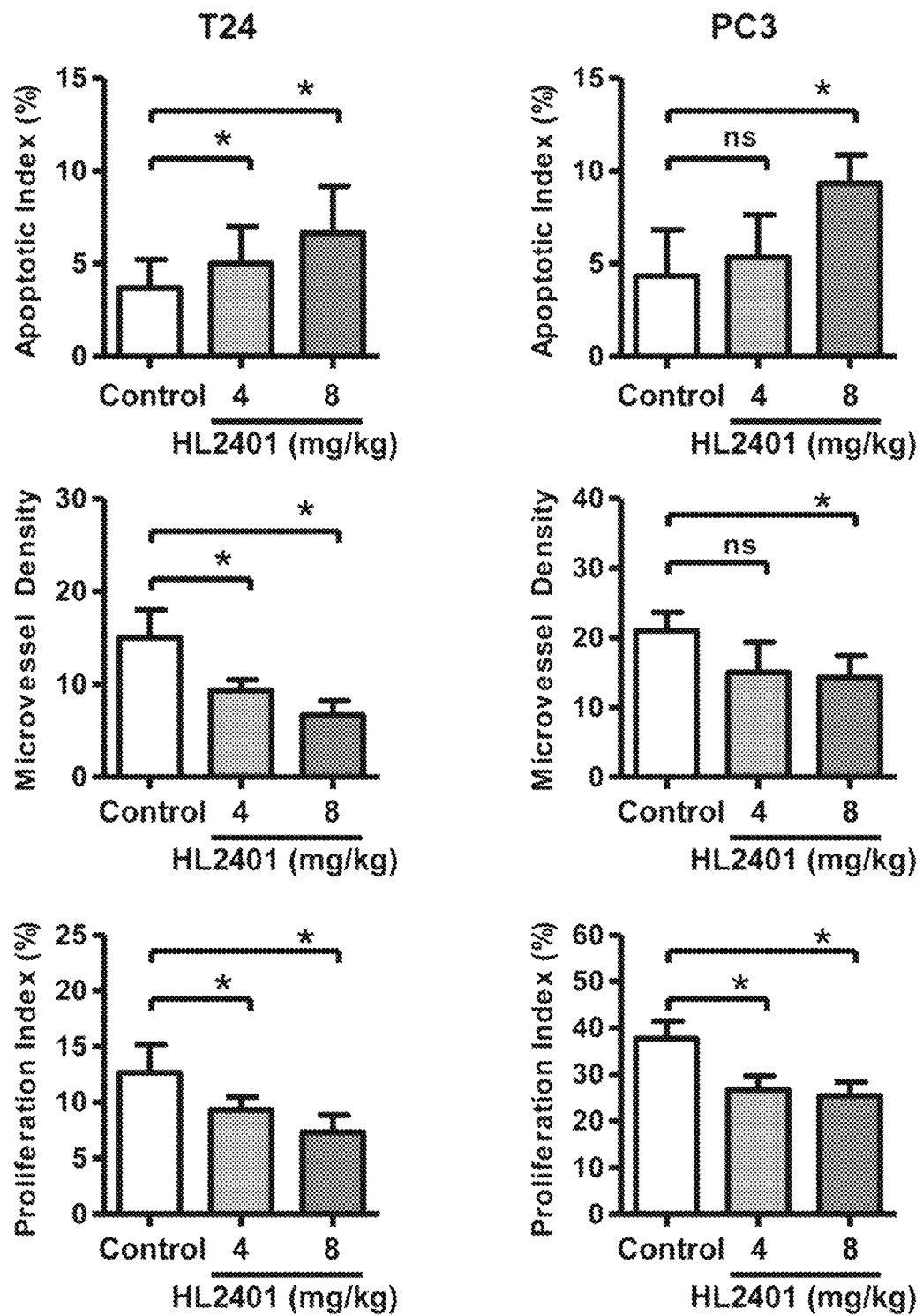

FIGS. 6A and 6B show that apoptotic index was increased in T24 by 35% ($p<0.05$) in tumors from animals treated with 8 mg/kg of HL2401. Apoptotic index in PC3 xenograft tumors was increased by 42% ($p<0.05$) in tumors treated with 8 mg/kg of HL2401. To monitor associated angiogenic index in these xenografts, microvessel density (MVD) was evaluated using PECAM-1 immunostaining. Analyses revealed a significant reduction of MVD (angiogenesis) in both T24 and PC3 xenografts treated with 8 mg/kg of HL2401. MVD was reduced in T24 by 52% ($p<0.05$) and by 43% ($p<0.05$) in PC3 tumors from animals treated with 8 mg/kg of HL2401.

To evaluate associated proliferative capability in these xenografts, proliferation index was evaluated using Ki-67 immunostaining. FIGS. 6A and 6B show, in line with the observed reduction in MVD, a reduction in proliferation index was evident in both T24 and PC3 xenografts treated with 8 mg/kg of HL2401. Proliferative index was reduced in T24 by 50% ($p<0.05$) and by 39% ($p<0.05$) in tumors from animals treated with 8 mg/kg of HL2401. These in vivo observations corroborate the in vitro findings and confirm a role for CXCL1 regulation of tumor growth associated with an increase in IL-6 expression and a reduction in TIMP4 expression, and support a role for CXCL1 as well as a role as a viable therapeutic target.

These results show administration of a neutralizing antibody that targets CXCL1, such as HL2401, resulted in the inhibition of endothelial sprouting, the inhibition of cellular invasion and the diminution of bladder and prostate xenograft growth through the inhibition of angiogenesis and proliferation, and the induction of apoptosis (REF). Therefore, therapeutic targeting of the chemokine CXCL1 could offer a novel strategy to inhibit tumor establishment and growth.

Furthermore, CXCL1, an inflammatory chemokine, may lead to the recruitment of inflammatory cells, such as lymphocytes and neutrophils. It is known that expression of the CXCL1 gene is accompanied by neutrophil infiltration. Therefore, anti-CXCL1 mAb of the present disclosure may be used to treat various conditions, such as cancer and other proliferative or inflammatory diseases.

In sum, CXCL1 expression in human cancer epithelial cells stimulates cells to invade and stimulates sprouting of endothelial cells. In addition, anti-CXCL1 neutralizing monoclonal antibody (HL2401) of the present disclosure can: a) inhibit cellular proliferation, b) inhibit cellular invasion, c) inhibit endothelial sprouting, and d) result in the inhibition of subcutaneous xenograft tumors expressing CXCL1 via reduction in both proliferation and angiogenesis, and the induction of apoptosis. Subsequently, the CXCL1 expression is positively correlated with the expression of IL-6 and inversely correlated with TIMP4 expression.

Example 6

Humanization of HL2401 Clone

A humanized single chain variable fragment (scFv) antibody (Hum HL2401_scFv)

It is common in the field of recombinant humanized antibodies to graft murine CDR sequences onto a well-established human immunoglobulin framework previously used in human therapies such as the framework regions of Herceptin [Trastuzumab]. In the construction of the human ScFv disclosed in this study a novel approach was taken to engineer a unique human immunoglobulin framework in order to avoid previous intellectual property issues surrounding the Herceptin framework [Genentech]. The humanized ScFv disclosed is thus anticipated to constitute a distinct patentable composition of matter.

The design strategy for this human ScFv antibody was to engineer optimal human consensus sequences for each of the variable heavy chain and light chains framework regions. This genetic engineering was achieved by first identifying human immunoglobulin germline genes orthologous to the murine heavy and light chain genes that comprise the murine mAb HL2401_scFv. Through analysis of human germline genes, a human consensus sequence was then designed that constituted a minimal positional template and afforded optimal chain packing residues of sufficient length to maintain overall 3-D conformation of the critical CDR residues. The template of this human consensus sequence was predicted, based on spacing and topological considerations, to retain the binding properties of the original mouse monoclonal antibody. The human consensus gene that was engineered, Hum HL2401_scFv, was predicted to encode an immunoglobulin sequence most similar in sequence and to reproduce the three-dimensional protein conformation and charge orientations within the paratope of the original 'parent" murine HL2401_scFv sequence.

As a key design strategy for the creation of this immunochemically active human ScFv that retains immunoreactivity with its cognate antigen, the approach outlined above may constitute a patentable method or process in its own right. The genetic engineering strategy for creating humanization murine monoclonal antibodies is thus based on selected germlines sequences that originate from un-rearranged immunoglobulin genes, based on the assumption that such frameworks should therefore be free from idiosyncratic mutations and are minimally immunogenic. Coupled with design tools that permit 3-D homology modelling of the resultant humanized ScFvs, comparisons can be made of the predicted humanized ScFv with the mouse monoclonal antibody protein structures and optimal CDR conformations can be maintained by editing and reshaping the variable region through varying the selection of packing residues at the interface of VH/VL. For patent disclosure purposes this genetic engineering strategy may constitute process claims in addition to claims covering composition of matter.

In this disclosure, the design of framework and complementarity determining regions of the humanized scFv Hum HL2401_scFv are outlined, including the 15-amino acid serine/glycine linker arm joining the heavy and light chains; the humanized ScFv is modelled in three dimensions; the purification of the ScFv is documented, and the specific immunoreactivity of the ScFv Hum HL2401_scFv with human CXCL1 will be determined.

General Approach

The three CDR regions of the HL2401murine heavy chain [H-CDR$_1$, H-CDR$_2$ and H-CDR$_3$] and the three CDR regions of the murine light chain [L-CDR$_1$, L-CDR$_2$, L-CDR$_3$] were grafted onto optimized human immunoglobulin heavy and light chain frameworks.

Antibody Numbering Scheme and CDR Definitions

The antibody-numbering server that is part of the Kabat-Man database http://www.bioinf.org.uk/) was used to number all antibody sequences in this study according to the enhanced Chothia scheme. In the humanization strategy, we have combined the enhanced Chothia numbering scheme with the contact CDR definition of antibody sequence to position the CDRs of the murine antibody light chain and heavy chains at the following locations: H-CDR$_1$ 26-35, H-CDR$_2$ 47-65, H-CDR$_3$ 93-101, L-CDR$_1$ 24-36, L-CDR$_2$ 46-55, and L-CDR$_3$ 89-96.

Selection of the Germline Based Human Consensus Template

To generate a humanized ScFv gene, six complementary determine regions (CDRs) of mouse VH and VL were grafted onto selected germlines based human consensus frameworks (FRs) showing the highest amino acids sequence identity to optimize the humanization and thus the predicted immunogenicity of the resultant ScFv protein. Human immunoglobulin germlines sequence showing the highest amino acid sequences similarity in FRs between human and mouse Hum HL2401 VH and VL were identified independently using from VBASE2-quest server http://www.vbase2.org/V-base (http://www.imgt.org/IMGT_v-quest) and Ig-BLAST server (http://www.ncbi.nlm.nih.gov/igblast). The highest four conserved human germline immunoglobulin sequences for heavy chain and light chains were selected. From these four human germline immunoglobulin sequences consensus human frameworks were designed for the grafting of CDRs residues of the "parent" mouse HL2401_scFv. The amino acid sequences in FRs of mouse VH and VL that differed from germline-based consensus human FRs were substituted with appropriate human residues, while preserving mouse residues at position known as Vernier zone residues and chain packing residues. Important to the construction of this biologically active human ScFv was the substitution of appropriate human residues in the framework regions whenever murine sequences differed from consensus human framework sequences. This included human sequences considered "Vernier zone residues" as well as chain packing residues.

Table 3 summarizes antibody gene after humanization.

TABLE 3

| Gene sequence | Z value (humanness of VH) | Z value (humanness of VL) |
|---|---|---|
| Mouse Gene (MumHL2401 scFv) | −1.4 | −0.6 |
| HumBB2401 scFv humanized version 1 | −0.5 | 0.7 |
| HUM2401-ScFv_1 humanized version 2 | 0.8 | 0.7 |

TABLE 4

| Humanized Version | Domain | Protein sequence | DNA sequence |
|---|---|---|---|
| HumBB2401 scFv (humanized version 1) | VL | SEQ ID NO: 12 | SEQ ID NO: 13 |
|  | VH | SEQ ID NO: 14 | SEQ ID NO: 15 |
|  | Full length | SEQ ID NO: 16 | SEQ ID NO: 17 |
| HUM2401-ScFv_1 humanized version 2 | VL | SEQ ID NO: 12 | SEQ ID NO: 13 |
|  | VH | SEQ ID NO: 18 | SEQ ID NO: 19 |
|  | Full length | SEQ ID NO: 20 | SEQ ID NO: 21 |

Figure 7:
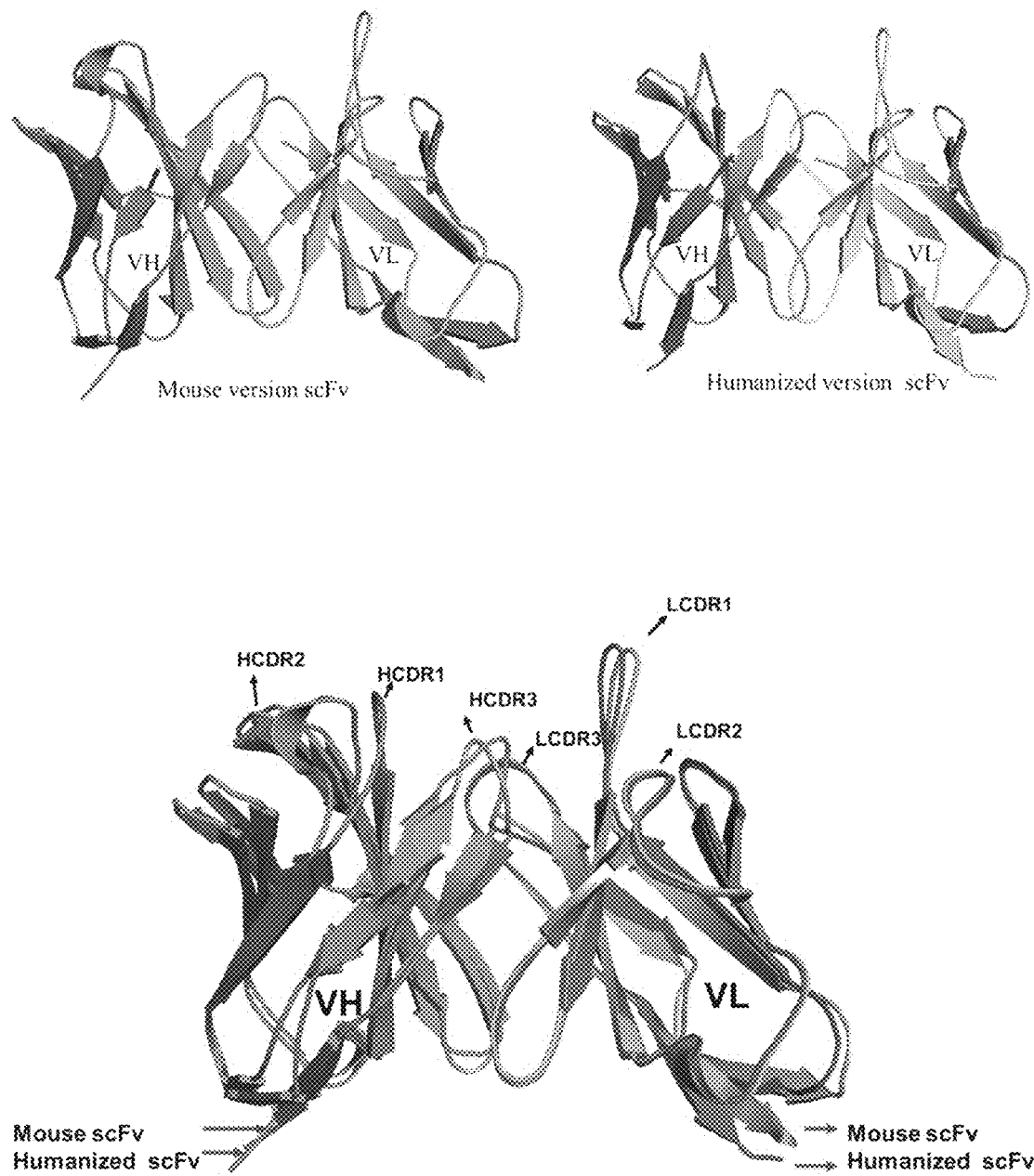
FIG. 7 shows homology modelling of mouse and humanization template sequence using Rosetta homology modelling server.

FIG. 7 shows homology modelling of mouse and humanization template sequence using Rosetta homology modelling server. Green color schematic model indicated for mouse sequence template and firebrick color schematic model indicated HumBB2401 scFv (humanized version 1). The diagram was generated using PyMole molecular graphic system.

Second Strategy

HUM2401-ScFv_1 (humanized version 2) was generated by fusing HumBB2401 scFv VL (SEQ ID NO: 12) with VH (SEQ ID NO: 18).

Figure 8:
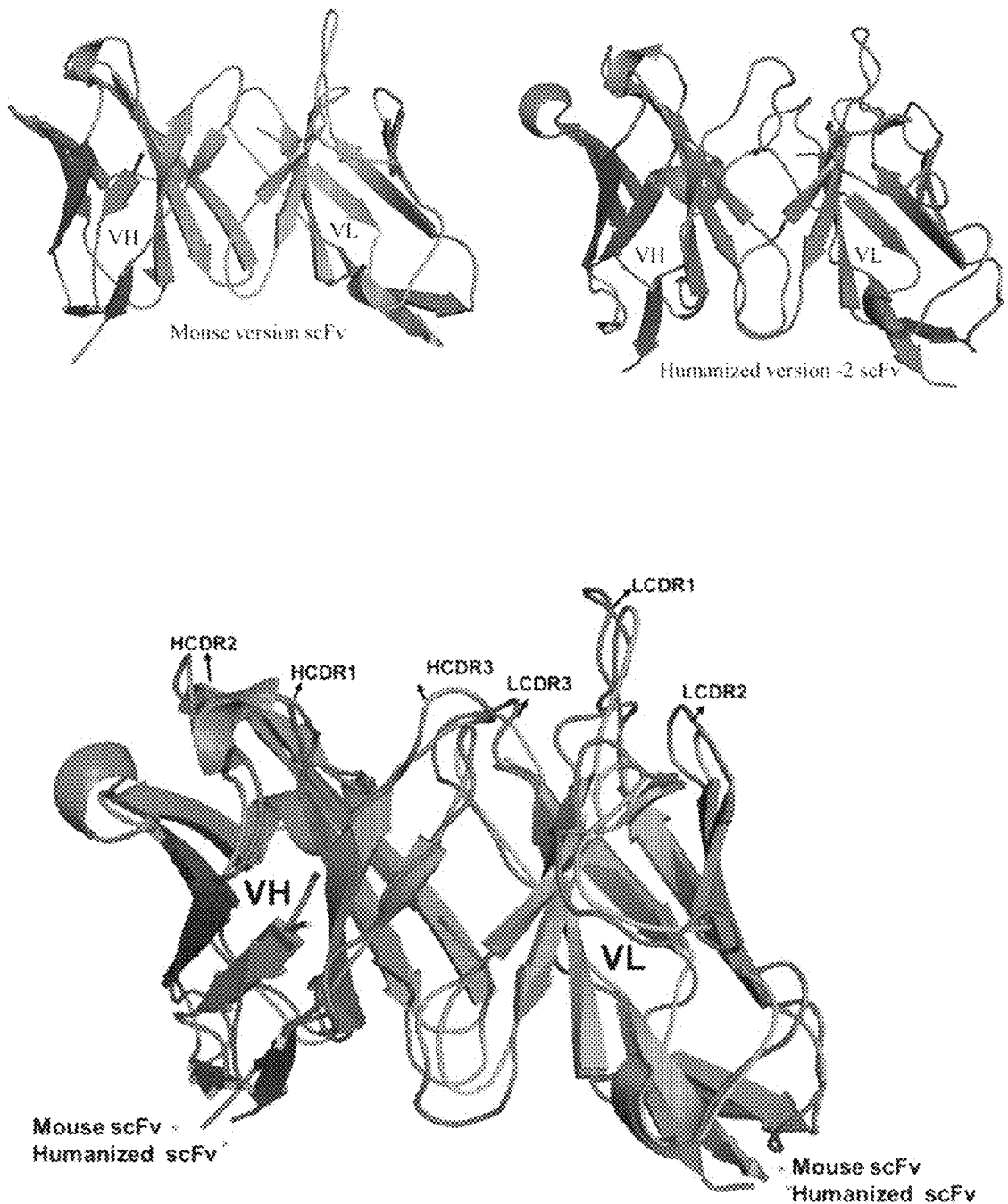
FIG. 8 shows homology modelling of mouse and humanization template sequence using Rosetta homology modelling server.

FIG. 8 shows homology modelling of mouse and humanization template sequence using Rosetta homology modelling server. Green color schematic model indicated for mouse sequence template and firebrick color schematic model indicated HUM2401-ScFv_1 (humanized version 2). The diagram was generated using PyMole molecular graphic system.

Figure 9:
FIG. 9 shows sequence alignment according to one embodiment of the present disclosure.

FIG. 9 shows sequence alignment between mouse gene, MumHL2401 scFv and humanized genes, i.e., HumBB2401 scFv (humanized version 1) and HUM2401-ScFv_1 (humanized version 2).

Additional humanized clones are shown in Table 5.

TABLE 5

| Humanized Version | Protein sequence | DNA sequence |
|---|---|---|
| Hum2401 scFv-3 | SEQ ID NO: 22 | SEQ ID NO: 23 |
| HumBB2401-3 | SEQ ID NO: 24 | SEQ ID NO: 25 |

FIG. 10 shows sequence alignment between Hum2401 scFv-3 and HumBB2401-3.

Induction of ScFv Proteins in Bacterial Host

The humanized HL2401_scFv clones were constructed into bacterial expression vector and transformed into T7 shuffle bacterial strain. T7 shuffle cells and was grown in 1.5 L 2×YT plus ampicillin medium at 37° C. until log-phage (OD600=0.5), induced with 0.3 mM IPTG, and allowed to grow at 30° C. for an additional 16 hrs. After induction, the bacteria were harvested by centrifugation at 8000 g for 15 min at 4° C., and the pellets were stored in −20° C. for at least 2 hrs. The frozen pellets were briefly thawed and suspended in 40 ml of lysis buffer (1 mg/ml lysozyme in PBS plus EDTA-free protease inhibitor cocktail (Thermo Scientific, Waltham, Mass.). The lysis mixture was incubated on ice for an hour, and then 10 mM MgCL2 and 1 µg/ml DNase I were added and the mixture was incubated at 25° C. for 20 min. The final lysis mixture was centrifuged at 12000 g for 20 min and the supernatants were collected. This supernatant was termed the periplasmic extract used for Protein L column affinity chromatography.

Western Blots Analysis Using HL2401_scFv Protein

Purified recombinant human CXCL1 protein was used as antigen target in Western blot analyses. 500 ng human CXCL1 protein and 1 µg purified protein as negative control were loaded onto 4-20% gradient Tris-glycine SDS-PAGE and transferred onto intracellular membranes. The membrane was blocked using 3% skimmed milk in PBS for 3 h at room temperature. After that, the membrane was incubated with partial purified humanized HL2401_scFv protein overnight at 4° C. The membrane was washed with sodium phosphate buffered saline with 0.05% tween 20 buffer (PBST) 3 times. The washed membrane was incubated with anti-c Myc mouse IgG for 1 h at room temperature to recognize the c-Myc tag on the scFv and identify the position of antigens bound by the scFv. After washing with PBST, the membrane was incubated with the goat anti-mouse IgG (H+L) HRP conjugate diluted (1:3000 v/v) in PBS for 1 h at RT, and specific immunoreactive bands were visualized with a mixture of TMB substrate.

Figure 11:
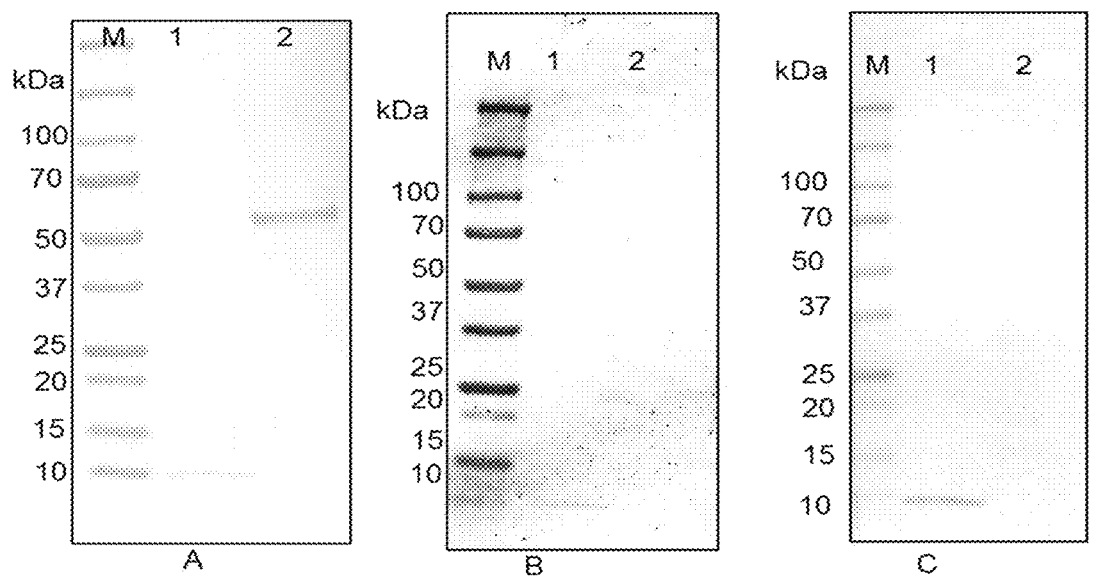
FIG. 11A-11C shows the antigen CXCL1 and a negative control protein was electrophoresed and transblotted to the nitrocellulose membrane.

FIG. 11 shows the antigen CXCL1 and a negative control protein was electrophoresed and transblotted to the nitrocellulose membrane. The antigens were probed with the humanized version of scFvs antibodies, followed by anti-C Myc mouse monoclonal antibody and a respective secondary antibody conjugated to HRP. Bound antibodies were visualized by using TMB. Lane M indicated for molecular marker, Lane 1 indicates for human CXCL1 protein (300 ng) and lane 2 indicates as negative control. Panel A represents for ponceau staining, Panel B represents Western blot analysis using purified Hum2401scFv antibody and Panel C represents Western blot analysis using purified HumBB2401scFv antibody.

On the other hand, an anti-Myc tag monoclonal antibody, used to recognize the Myc tag on the expressed of scFv protein. The antigen loaded membrane was incubated with anti-myc-HRP (1/2000) antibody and specific immunoreactive bands were visualized with a mixture of TMB substrate.

Figure 12:
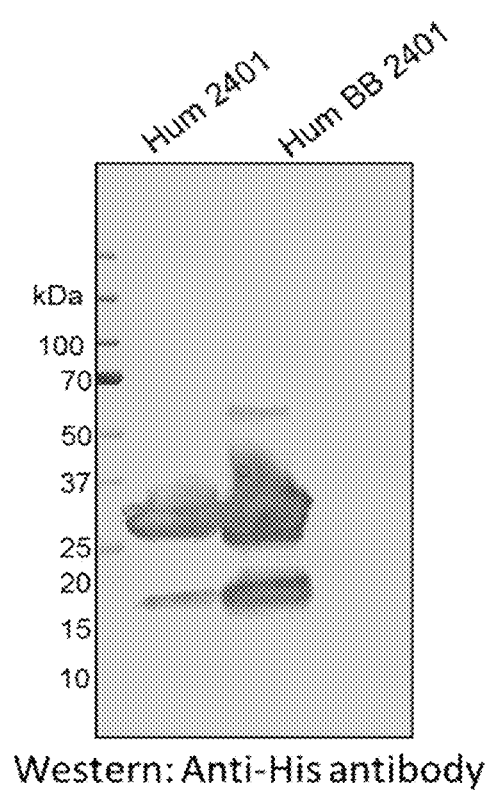
FIG. 12 shows humanized version of HL2401_scFv protein expressed in *E. coli* and purified that was detected by anti-His tag antibody.

FIG. 12 shows humanized version of HL2401_scFv protein expressed in E. coli and purified that was detected by anti-His tag antibody.

ELISA test for confirm the binding activity of HL2401_scFv protein

The human CXCL1 protein was coated onto 96-well, 30 ng for well at 4° C. overnight. The plate was blocked by 3% skim milk in PBS 2 h at room temperature. The plate was washed 3 times with PBST and applied anti-human CXCL1 humanized version scFv antibodies at different dilution concentration. The anti-Myc mouse monoclonal antibody with HRP conjugate antibody was applied and developed with TMB solution.

Figure 13:
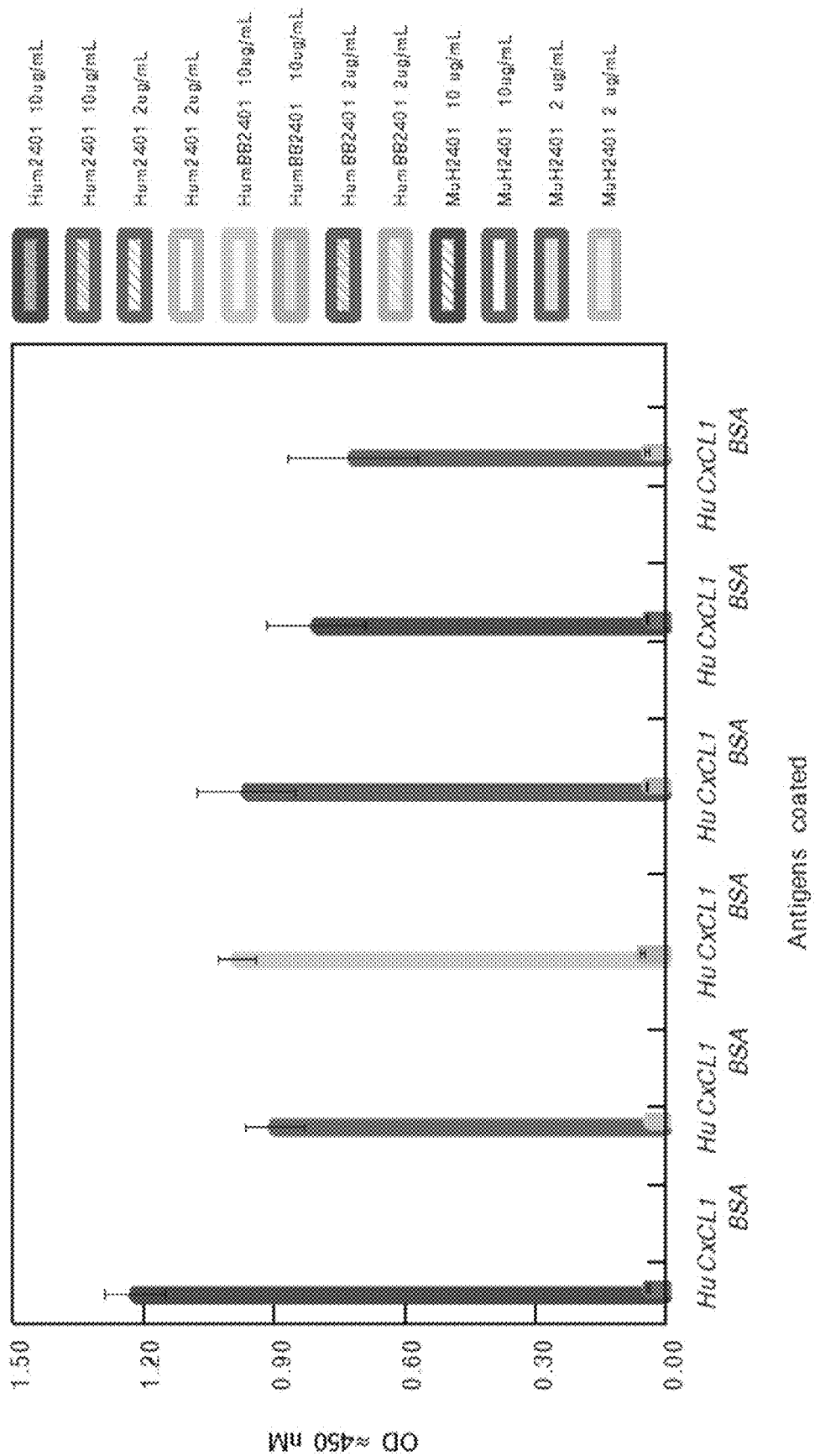
FIG. 13 shows the humanization version of H2407 scFvs format antibody proteins are specially binding to human CXCL1 antigen in ELISA and Western blot analysis.

FIG. 13 shows the humanization version of H2407 scFvs format antibody proteins are specially binding to human CXCL1 antigen in ELISA and Western blot analysis. This ELISA and Western blot analysis results do not correlate as dose depend activity of these antibody.

Example 7

Design the Reformatting Hum2401 Derivatives

Light chain of both humanize version may be fused with a signal peptide:

```
                              (SEQ ID NO: 26)
        MDSQAQVLMLLLLWVSGTCG.
```

Heavy chain of humanize version Hum2401 derivatives may be fused with a signal peptide:

```
                              (SEQ ID NO: 27)
        MEFGLSWVFLVAILKGVQC.
```

The fusion proteins of the Hum2401 derivatives are summarized in Table 6.

TABLE 6

| Hum2401 fusion protein | Protein sequence | DNA sequence |
| --- | --- | --- |
| Hum2401 VL-signal | SEQ ID NO: 28 | SEQ ID NO: 29 |
| Hum2401 VH-signal | SEQ ID NO: 30 | SEQ ID NO: 31 |
| HumBB 2401 VH-signal | SEQ ID NO: 32 | SEQ ID NO: 33 |

Sub-Cloning Into Mammalian Expression Vector

Figure 14:
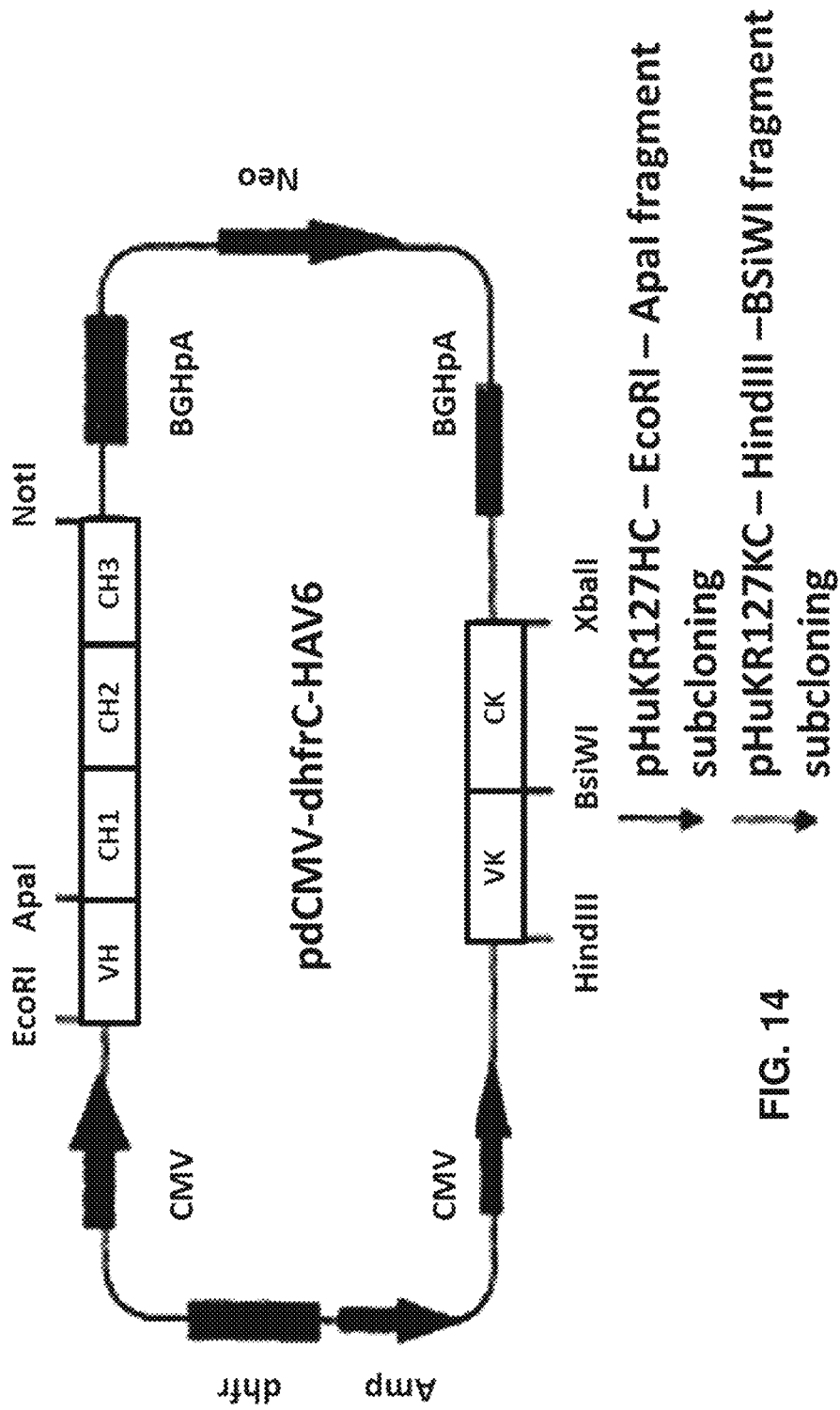
FIG. 14 shows schematics for cloning of the light chain and heavy chain of humanized gene according to one embodiment of the present disclosure.

As shown in FIG. 14, the light chain and heavy chain of humanized gene were sub-cloned using EcoR I and Apa I for heavy chain and Hind III and BsiWi for light chain. First, the light chain gene was cloned into vector and plasmid DNA was sequenced. The correct light chain inserted clone was used for second step sub-cloning for heavy chain of two version of humanization. The ligated clones were amplified and send for sequencing. The correct inserted heavy chain clones were used for large scale DNA preparation. Preparation of large amount of plasmid DNA using endotoxin free Kit. The clones are summarized in Table 7.

TABLE 7

| Clone | Protein sequence | DNA sequence |
| --- | --- | --- |
| PCMV-dhfr-H2401 Light chain clone 5 | SEQ ID NO: 34 | SEQ ID NO: 35 |
| Pcmv-dhfrhumBB2401VH clone 1 | SEQ ID NO: 36 | SEQ ID NO: 37 |
| Pcmv dhfr-HumBB2401 clone 4 | SEQ ID NO: 38 | SEQ ID NO: 39 |

Cell Line HEK293 F Suspension Culture

Transient Transfection and Production in Suspension HEK 293-F Cells

1. Approximately 24 hours before transfection, pass Freestyle 293-F cells at $0.6 \times 10^6$-$0.7 \times 10^6$ cells/mL. Place the flasks (125 mL or 100 mL Erlenmeyer flasks with ventilation membrane caps) on an orbital shaker platform rotating at 135 rpm at 37° C., 8% CO2.
2. On the day of transfection, the cell density should be about $1.2 \times 10^6$-$1.5 \times 10^6$/mL. Dilute the cells to $1 \times 10^6$ cells/mL. Add 30 mL of the cells into each 125-mL shake flask.
   a. For small scale productions in Erlenmeyer flasks containing 100 mL total working volume of cell suspension incubated at 150 rpm in a linear shaker.
   b. A total of 1 µg high quality plasmid-DNA (prepared using Takara Clontech Nucleobond Xtra Midi EF plasmid isolation kit) and 2.5 µg PEI per mL culture volume (total 100 µg DNA) was prepared in 1/10 volume of fresh serum free culture medium.
   c. Dilute PEI in appropriate volume of serum free medium in a polystyrol Plate or tube (Do not use polypropylene tubes).
   d. Dilute Plasmid-DNA in appropriate volume DMEM and mix with the PEI Suspension.
   e. Incubate the mixture at RT for 30 min to allow formation of PEI::DNA complexes.
   f. Disperse PEI::DNA suspension evenly over the cells.
   g. Cells are further cultured for 6-day.
   h. Test yield of human IgG.

Preparation of the Transfection Reagent, PEI:

PEI (polyethylenimine), a cationic polymer is a 25 kDa linear from Polysciences (Polysciences, Cat. No. 23966-2) Note: Portolano et al (2014) used branched form of PEI (Sigma Aldrich cat. No. 408727).

Assay for Activity of Humanized IgG Version

ELISA test for confirm the binding activity of HL2401_scFv protein

The human CXCL1 protein was coated onto 96-well, 30 ng for well at 4° C. overnight. The plate was blocked by 3% skim milk in PBS 2 h at room temperature. The plate was washed 3 times with PBST and applied anti-human CXCL1 humanized version IgG antibodies were diluted 1/100 and 1/10 in PBS and subjected into antigen coated plate for 1 h at room temperature. The donkey anti-human monoclonal antibody with HRP conjugate antibody was diluted 1/3000 and applied for 45 min at room temperature, afterwards washed 3 times with PBST and developed with TMB solution.

Figure 15:
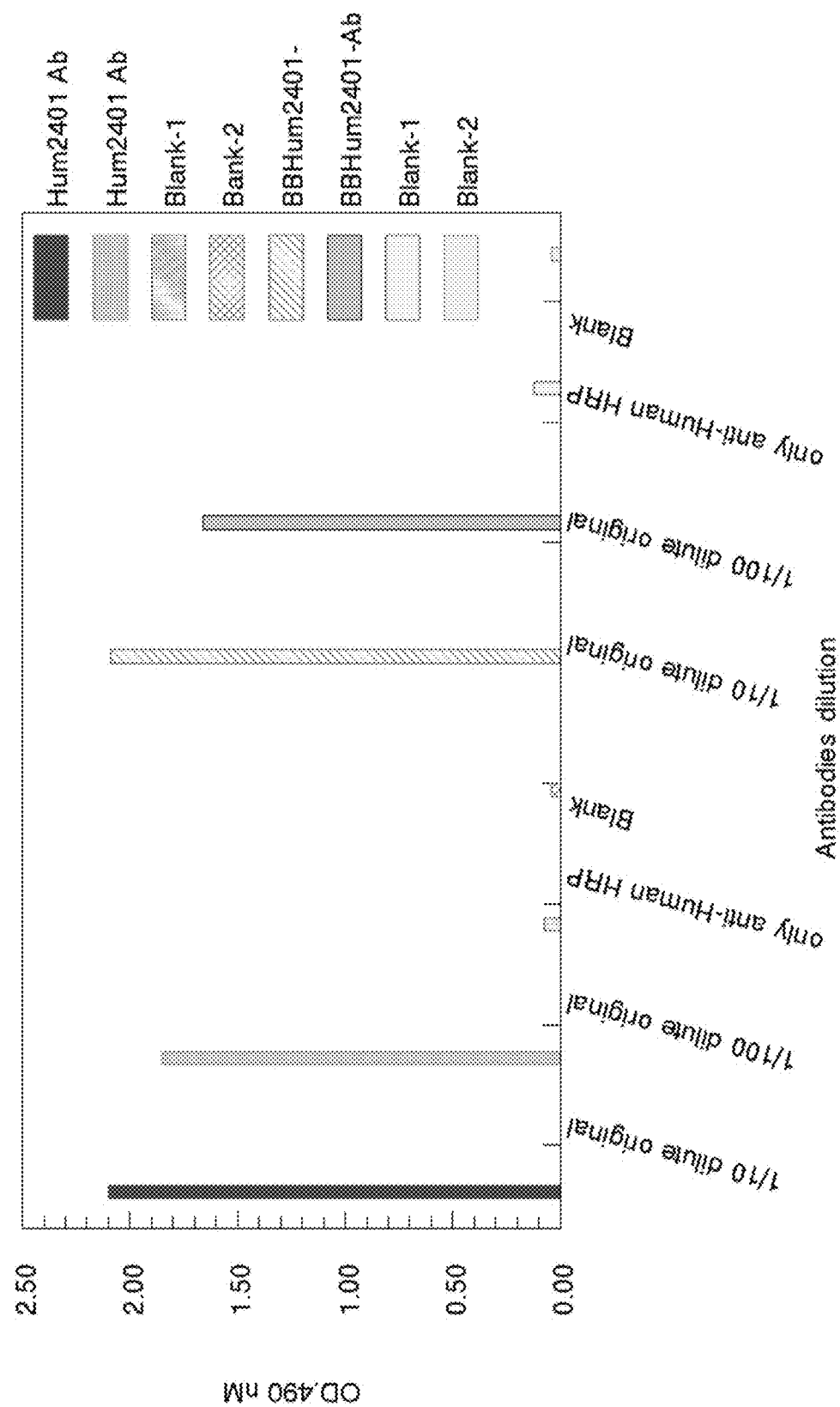
FIG. 15 shows ELISA results.

Table 8 and FIG. 15 show the ELISA results.

TABLE 8

| Hum2401 Ab | ELISA signals | | Min |
|---|---|---|---|
| 1/10 dilute original | 2.098 | 2.098 | 2.098 |
| 1/100 dilute original | 1.848 | 1.908 | 1.848 |
| only anti-Human HRP | 0.206 | 0.075 | 0.075 |
| Blank | 0.044 | 0.044 | 0.044 |
| HumBB2401 Ab | ELISA signals | | Min |
| 1/10 dilute original | 2.091 | 2.094 | 2.091 |
| 1/100 dilute original | 1.662 | 1.665 | 1.662 |
| only anti-Human HRP | 0.151 | 0.121 | 0.121 |
| Blank | 0.043 | 0.048 | 0.043 |

Western Blots Analysis Using Humanized HL2401_IgG Derivatives

Purified recombinant human CXCL1 protein was used as antigen target in Western blot analyses. 200 ng and 500 ng human CXCL1 protein and bacterial cell lysate with chicken lysozyme protein as negative control were loaded onto 4-20% gradient Tris-glycine SDS-PAGE and transferred onto intracellular membranes. The membrane was blocked using 3% skimmed milk in PBS for 3 h at room temperature. After that, the membrane was incubated with transfected supernatant of humanized HL2401_IgG variants protein overnight at 4° C. The membrane was washed with sodium phosphate buffered saline with 0.05% tween 20 buffer (PBST) 3 times. The washed membrane was incubated with donkey anti-Human (H+L) HRP conjugate antibody for 1 h at room temperature to recognize the humane heavy and light chain of constant region and identify the position of antigens bound by the reformatting humanized antibodies, and specific immunoreactive bands were visualized with a mixture of TMB substrate.

Figure 16:
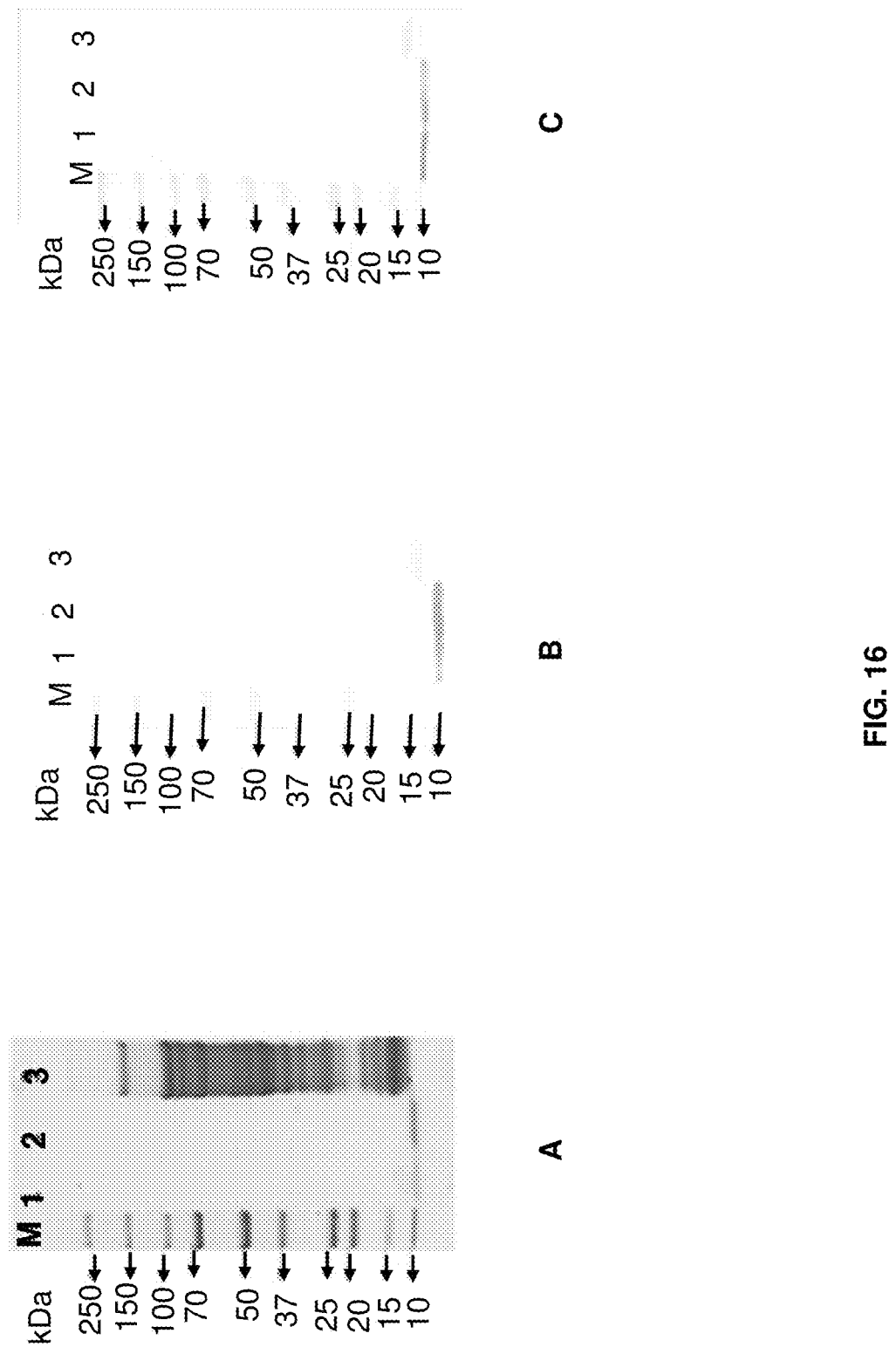
FIG. 16A-16C shows the antigen human CXCL1 and a negative control bacterial cell lysate with chicken lysozyme protein were electrophoresed and transblotted to the nitrocellulose membrane.

FIG. 16 shows the antigen human CXCL1 and a negative control bacterial cell lysate with chicken lysozyme protein were electrophoresed and transblotted to the nitrocellulose membrane. The antigens were probed with the humanized version of IgG antibodies, followed by anti-human (H+L) secondary antibody conjugated to HRP. Bound antibodies were visualized by using TMB. Lane M indicated for molecular marker, Lane 1 represents for human CXCL1 protein (200 ng) and lane 2 represents human CXCL1 protein (200 ng) Lane 3 represents as negative control. Panel A represents for SDS-PAGE staining, Panel B represents Western blot analysis using purified Hum2401 IgG antibody and Panel C represents Western blot analysis using purified HumBB2401 IgG antibody, respectively.

Purification of Transfected Culture Supernatant Using Protein G Affinity Chromatography The transfected cells were harvested and filter the supernatant using 0.45 u and loaded protein G affinity chromatography using AKTA pure L system. The protein was eluted using 0.2M Glycine pH2.5 and neutralized with 1M Tris-HCL pH: 9. the eluted fractions were analyzed into SDS-PAGE.

Figure 17:
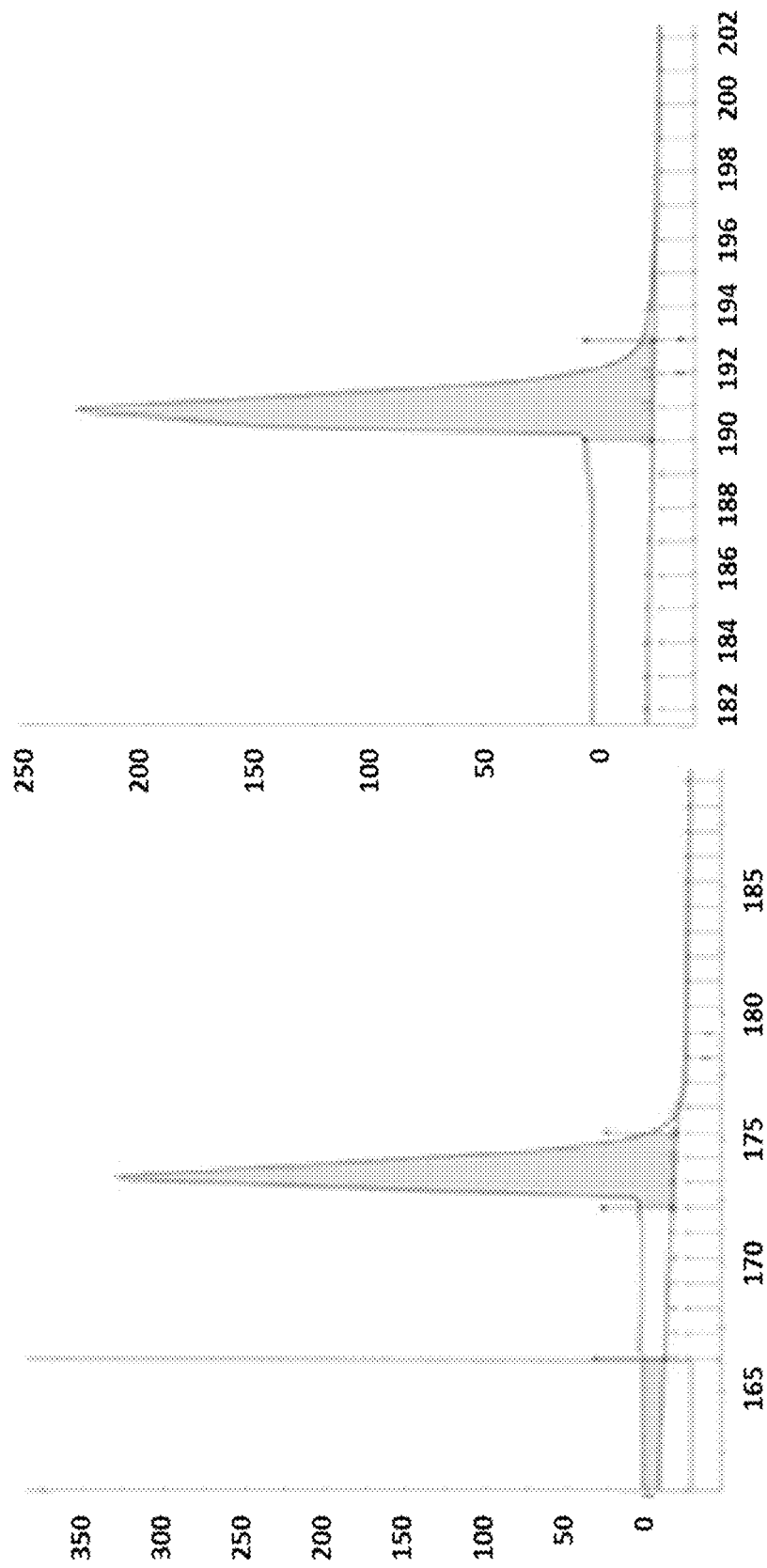
FIGS. 17A and 17B show affinity purification chromatogram of purified samples according to one embodiment of the present disclosure.

FIGS. 17A and 17B show affinity purification chromatogram of Hum2401 and HumBB2401 IgG, respectively.

Table 9 summarized the affinity purification chromatogram results.

TABLE 9

| Protein | Approx. Concentration | Total Volume | Concentration mg/ml |
|---|---|---|---|
| Hum2401IgG | 1.6 mg | 3 ml | 0.539 mg/ml |
| HumBB2401 | 1 mg | 3 ml | 0.35 mg/ml |

Figure 18:
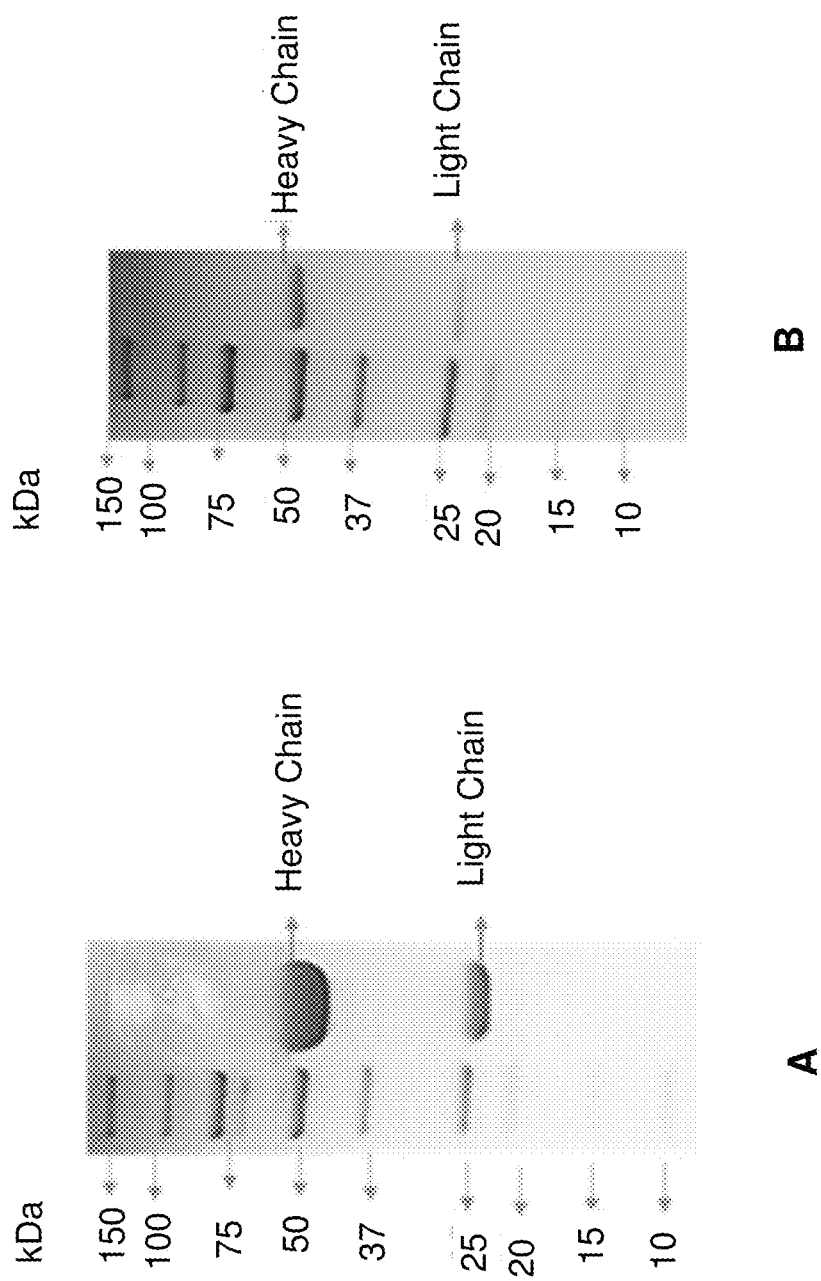
FIGS. 18A and 18B shows SDS-PAGE gel electrophoresis of purified samples according to one embodiment of the present disclosure.

FIG. 18 shows SDS-PAGE gel electrophoresis of purified samples, Panel A represents for SDS-PAGE staining of purified protein Hum2401 peak 9 and Panel B represents for SDS-PAGE staining of purified protein Hum2401 peak 10.

List of Deliverable Samples

| 1. Protein samples | | | |
|---|---|---|---|
| Sample name | Approx. Concentration total | Total Volume | Concentration mg/ml |
| Hum2401IgG | 1.6 mg | 3 ml | 0.539 mg/ml |
| HumBB2401 | 1 mg | 3 ml | 0.35 mg/ml |

| 2. Plasmid DNA samples | | | |
|---|---|---|---|
| Sample name | Specification | Plasmid Name | Sample |
| POE-mu H2401scFv | Mouse scFv | ScFv expression vector under T7 promoter (periplasmic) | Plasmid DNA |
| POE-HumH2401scFv | Humanized scFv | ScFv expression vector under T7 promoter (periplasmic) | Plasmid DNA |
| POE-HumBBH2401scFv | Humanized scFv | ScFv expression vector under T7 promoter (periplasmic) | Plasmid DNA |
| Pcmvdhfr-Hum2401(H + L) | Reformatting humanized IgG version | Mammalian expression vector including humanized gene | Plasmid DNA |
| Pcmvdhfr-HumBB2401(H + L) | Reformatting humanized IgG version | Mammalian expression vector including humanized gene | Plasmid DNA |

Example 8

Effects on Angiogenesis by Humanized Anti-CXCL1 Antibodies

Humanized Anti-CXCL1 Antibodies Inhibit Endothelial Cell Sprouting

FIGS. 19A-19H show that humanized anti-human CXCL1 antibodies BB2401 and Hum2401 are as effective as Avastin in the inhibition of endothelial cell sprouting.

Figure 19:
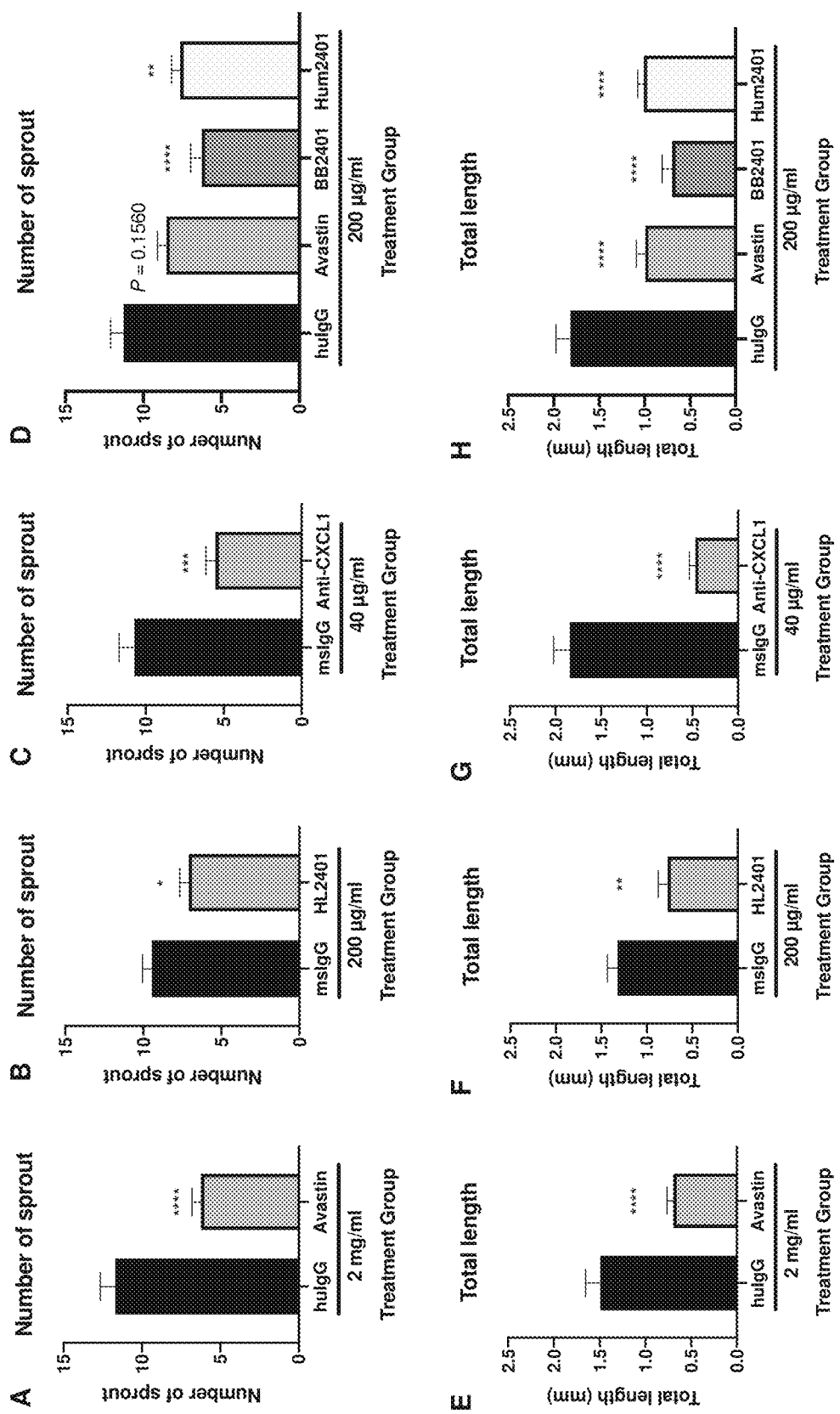
FIGS. 19A-19H show that humanized anti-human CXCL1 antibodies HumBB2401 (a.k.a. BB2401) and Hum2401 are as effective as Avastin in the inhibition of endothelial cell sprouting.

Briefly, the positive control Bevacizumab (Avastin) at frequently used concentration (2 mg/ml) significantly reduced number of sprout (FIG. 19A) and total length of sprouts (FIG. 19E). Mouse anti-human CXCL1 antibody HL2401 and commercial anti-human CXCL1 antibody (Anti-CXCL1) also significantly reduced number of sprout (FIGS. 19B and 19C) and total length of sprouts (FIGS. 19F and 19G). The effect of anti-human CXCL1 antibodies BB2401 and Hum2401 were tested in comparison with Avastin at the concentration of 200 pg/ml. Avastin at the concentration of 200 μg/ml showed similar level of inhibitory effects as 2 mg/ml on the reduction in number of sprout (FIG. 19D) and total length of sprouts (FIG. 19H). Hum2401 had the same level of inhibitory effects as Avastin (FIGS. 19D and 19H). Notably, BB2401 demonstrated stronger inhibitory effects than Avastin on number of sprout (FIG. 19D) and total length of sprouts (FIG. 19H). Taken together, neutralization of CXCL1 by humanized anti-human CXCL1 antibodies BB2401 and Hum2401 leads to inhibition of angiogenesis. The asterisks *, , *, and **** indicate the p value is ≤0.05, <0.01, <0.001 and <0.0001, respectively.

Humanized Anti-CXCL1 Antibodies Inhibit Endothelial Cell Tube Formation

Figure 20:
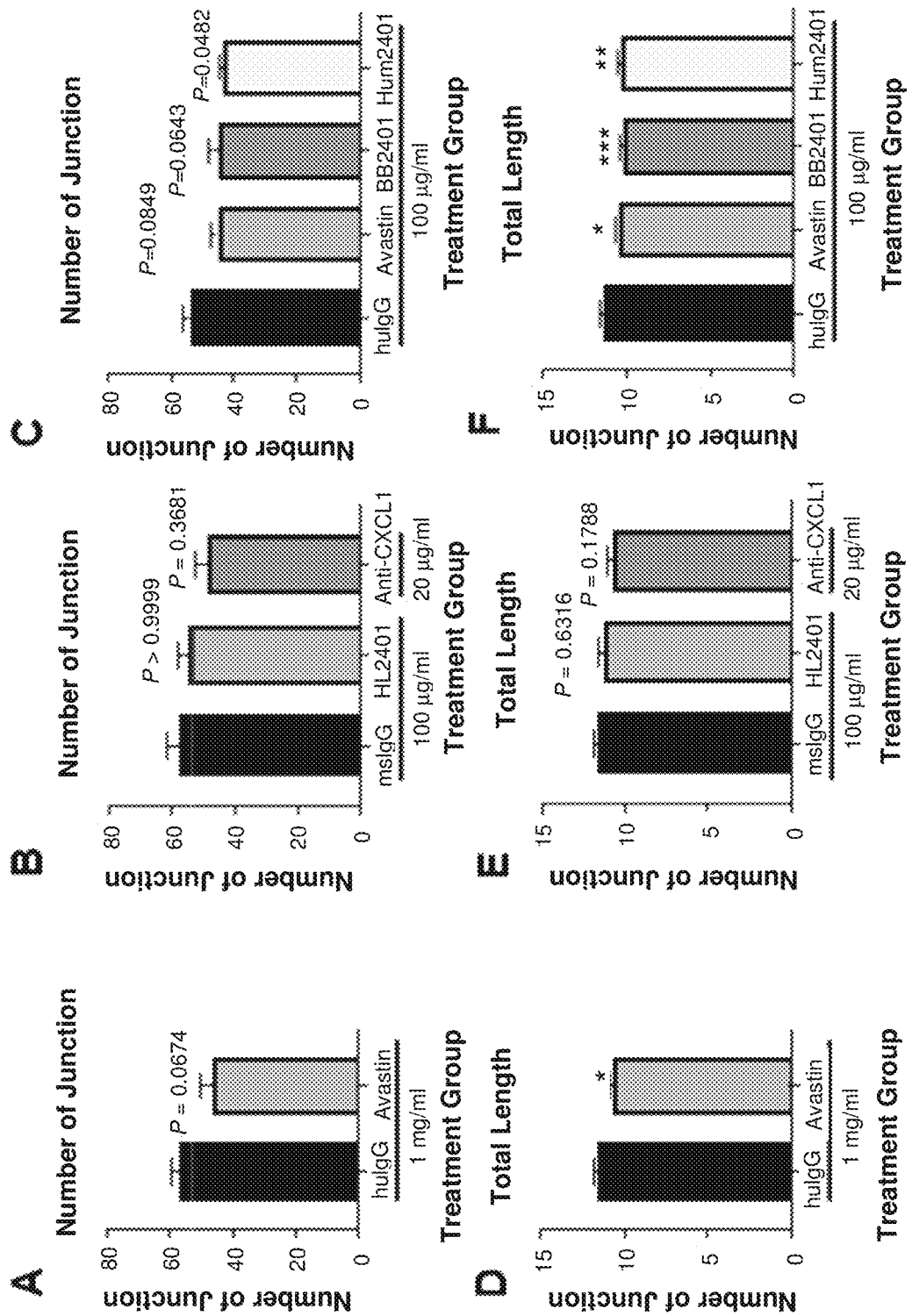
FIGS. 20A-20F show that humanized anti-human CXCL1 antibodies HumBB2401 (a.k.a. BB2401) and Hum2401 are as effective as Avastin in the inhibition of endothelial cell tube formation.

FIGS. 20A-20F show that humanized anti-human CXCL1 antibodies BB2401 and Hum2401 are as effective as Avastin in the inhibition of endothelial cell tube formation. Briefly, the positive control Avastin at frequently used concentration (1 mg/ml) significantly reduced total length of tubing (FIG. 20D), but not number of junction (FIG. 20A). As comparative control, mouse anti-human CXCL1 antibody HL2401 and commercial anti-human CXCL1 antibody (anti-CXCL1) did not significantly reduce the number of junction (FIG. 20B) and total length of tubing (FIG. 20E). The effect of BB2401 and Hum2401 in comparison with Avastin at the concentration of 100 μg/ml was tested. FIG. 20F shows Avastin at the concentration of 100 μg/ml has a similar inhibitory effects on total length of tubing as at the concentration of 1 mg/ml (FIG. 20D). FIG. 20F also shows both BB2401 and Hum2401 had the same levels of inhibitory effects as Avastin on total length of tubing. The asterisks *,  and * indicate the p value is ≤0.05, <0.01 and <0.001, respectively.

All methods described herein can be performed in any suitable order unless otherwise indicated herein or otherwise clearly contradicted by context.

The use of any and all examples, or exemplary language (e.g., "such as") provided herein, is intended merely to better illuminate the disclosure and does not pose a limitation on the scope of the disclosure unless otherwise indicated. No language in the specification should be construed as indicating any element is essential to the practice of the disclosure unless as much is explicitly stated.

The citation and incorporation of patent documents herein is done for convenience only and does not reflect any view of the validity, patentability and/or enforceability of such patent documents.

The present disclosure includes all modifications and equivalents of the subject matter recited in the aspects or claims presented herein to the maximum extent permitted by applicable law.

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior disclosure.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

What is claimed is:

1. A method of treating a patent who has cancer, comprising administering to the patient an antibody comprising a heavy chain variable domain comprising
CDR1 comprising the amino acid sequence of SEQ ID NO: 6,
CDR2 comprising the amino acid sequence of SEQ ID NO: 7, and
CDR3 comprising the amino acid sequence of SEQ ID NO: 8, and a light chain variable domain comprising
CDR1 comprising the amino acid sequence of SEQ ID NO: 9,
CDR2 comprising the amino acid sequence of SEQ ID NO: 10, and
CDR3 comprising the amino acid sequence of SEQ ID NO: 11,
wherein the cancer is bladder cancer or prostate cancer.

2. The method of claim 1, wherein the light chain variable domain comprises the amino acid sequence of SEQ ID NO: 12 and the heavy chain variable domain comprises the amino acid sequence of SEQ ID NO: 14 or 18 .

3. The method of claim 1, wherein the light chain variable domain comprises the amino acid sequence of SEQ ID NO: 28 and the heavy chain variable domain comprises the amino acid sequence of SEQ ID NO: 30 or 32 .

4. The method of claim 1, wherein the light chain variable domain comprises CDR regions CDR1, CDR2, and CDR3 of the amino acid sequence of SEQ ID NO: 12, and the heavy chain variable domain comprises CDR regions CDR1, CDR2, and CDR3 of the amino acid sequence of SEQ ID NO: 14 or 18.

5. The method of claim 1, wherein the light chain variable domain comprises CDR regions CDR1, CDR2, and CDR3 of the amino acid sequence of SEQ ID NO: 28, and the heavy chain variable domain comprises CDR regions CDR1, CDR2, and CDR3 of the amino acid sequence of SEQ ID NO: 30 or 32.

6. The method of claim 1, wherein the heavy chain variable domain comprises
CDR1 consisting of the amino acid sequence of SEQ ID NO: 6,
CDR2 consisting of the amino acid sequence of SEQ ID NO: 7, and
CDR3 consisting of the amino acid sequence of SEQ ID NO: 8, and the light chain variable domain comprises
CDR1 consisting of the amino acid sequence of SEQ ID NO: 9,
CDR2 consisting of the amino acid sequence of SEQ ID NO: 10, and
CDR3 consisting of the amino acid sequence of SEQ ID NO: 11.

7. The method of claim 1, wherein the antibody comprises the amino acid sequence of SEQ ID NO: 16, 20, 22, or 24 .

8. The method of claim 1, wherein the light chain variable domain comprises a signal peptide comprising the amino acid sequence of SEQ ID NO: 26 and the heavy chain variable domain comprises a signal peptide comprising the amino acid sequence of SEQ ID NO: 27.

9. The method of claim 1, wherein the antibody is in the form of a composition comprising an adjuvant, and optionally, a pharmaceutically acceptable carrier, and optionally, pharmaceutically acceptable excipients and/or stabilizers.

10. The method of claim 9, wherein the adjuvant is selected from the group consisting of anti-CD40 antibody, imiquimod, resiquimod, GM-CSF, cyclophosphamide, sunitinib, bevacizumab, interferon-alpha, interferon-beta, CpG oligonucleotides and derivatives, poly-(I:C) and derivatives, RNA, sildenafil, particulate formulations with poly(lactide co-glycolide) (PLG), virosomes, interleukin (IL)-1, IL-2, IL-4, IL-7, IL-12, IL-13, IL-15, IL-21, and IL-23.

11. The method of claim 1, wherein the light chain variable domain comprises the amino acid sequence of SEQ ID NO: 12, and the heavy chain variable domain comprises the amino acid sequence of SEQ ID NO: 14.

12. The method of claim 1, wherein the light chain variable domain comprises the amino acid sequence of SEQ ID NO: 12, and the heavy chain variable domain comprises the amino acid sequence of SEQ ID NO: 18.

13. The method of claim 1, wherein the light chain variable domain comprises the amino acid sequence of SEQ ID NO: 28, and the heavy chain variable domain comprises the amino acid sequence of SEQ ID NO: 30.

14. The method of claim 1, wherein the light chain variable domain comprises the amino acid sequence of SEQ ID NO: 28, and the heavy chain variable domain comprises the amino acid sequence of SEQ ID NO: 32.

15. The method of claim 1, wherein the antibody comprises the amino acid sequence of SEQ ID NO: 16.

16. The method of claim 1, wherein the antibody comprises the amino acid sequence of SEQ ID NO: 20.

17. The method of claim 1, wherein the antibody comprises the amino acid sequence of SEQ ID NO: 22.

18. The method of claim 1, wherein the antibody comprises the amino acid sequence of SEQ ID NO: 24.

19. The method of claim 1, wherein the antibody binds to a human chemokine CXCL1 protein comprising the amino acid sequence of SEQ ID NO: 5.

* * * * *

SEQUENCE LISTING

<160> NUMBER OF SEQ ID NOS: 39

<210> SEQ ID NO 1
<211> LENGTH: 336
<212> TYPE: DNA
<213> ORGANISM: Mus musculus

<400> SEQUENCE: 1

```
gacattgtgc tgacccaatc tccagcttct ttggctgtgt ctctagggca gagggccacc      60
atctcctgca aggccagcca aagtgttgat tatgatggtg atagttatgt gaactggtac     120
caacagaaac caggacagcc acccaaactc ctcatctatg ctgcatccaa tctagaatct     180
cggatcccag ccaggtttag tggcagtggg tctgggacag acttcaccct caacatcctt     240
cctgtggagg aggatgatgg tgcaacctat tactgtcagc aaagtagtga ggatccgtgg     300
acgttcggtg gaggcaccaa gctggaaatc aaacgg                               336
```

<210> SEQ ID NO 2
<211> LENGTH: 112
<212> TYPE: PRT
<213> ORGANISM: Mus musculus

<400> SEQUENCE: 2

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Val Asn Trp Tyr Gln Gln Lys Pro Gly Gln Pro Pro
            35                  40                  45

Lys Leu Leu Ile Tyr Ala Ala Ser Asn Leu Glu Ser Arg Ile Pro Ala
    50                  55                  60

Arg Phe Ser Gly Ser Gly Ser Gly Thr Asp Phe Thr Leu Asn Ile Leu
65                  70                  75                  80

Pro Val Glu Glu Asp Asp Gly Ala Thr Tyr Tyr Cys Gln Gln Ser Ser
                85                  90                  95

Glu Asp Pro Trp Thr Phe Gly Gly Gly Thr Lys Leu Glu Ile Lys Arg
            100                 105                 110

<210> SEQ ID NO 3
<211> LENGTH: 356
<212> TYPE: DNA
<213> ORGANISM: Mus musculus

<400> SEQUENCE: 3
gaagtgaagc tggtggagtc tggggctgaa ctggtgaagc ctggggcttc agtgaagttg        60
tcctgcaagg cttctggcta caccttcacc agctactata tatactgggt gaaacagagg       120
cctggacaag ccttgagtg gattggagag attgatccta gccatggtgg tcctaccttc        180
aatgagaagt tcaagaacaa ggccacactg actgtagaca atcatccag cacagcatac        240
atgcaactca gcagcctgac atctgacgac tctgcggtct attactgtac aagagagtcg       300
gggacgggag ctatggacta ctggggtcaa ggaaccactc tcacagtctc ctcggg           356

<210> SEQ ID NO 4
<211> LENGTH: 118
<212> TYPE: PRT
<213> ORGANISM: Mus musculus

<400> SEQUENCE: 4

Glu Val Lys Leu Val Glu Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Tyr Ile Tyr Trp Val Lys Gln Arg Pro Gly Gln Gly Leu Glu Trp Ile
            35                  40                  45

Gly Glu Ile Asp Pro Ser His Gly Gly Pro Thr Phe Asn Glu Lys Phe
    50                  55                  60

Lys Asn Lys Ala Thr Leu Thr Val Asp Lys Ser Ser Ser Thr Ala Tyr
65                  70                  75                  80

Met Gln Leu Ser Ser Leu Thr Ser Asp Asp Ser Ala Val Tyr Tyr Cys
                85                  90                  95

Thr Arg Glu Ser Gly Thr Gly Ala Met Asp Tyr Trp Gly Gln Gly Thr
            100                 105                 110

Thr Leu Thr Val Ser Ser
            115

<210> SEQ ID NO 5
<211> LENGTH: 73
<212> TYPE: PRT

-continued

```
<213> ORGANISM: Artificial Sequence
<220> FEATURE:
<223> OTHER INFORMATION: Synthetic

<400> SEQUENCE: 5

Ala Ser Val Ala Thr Glu Leu Arg Cys Gln Cys Leu Gln Thr Leu Gln
1               5                   10                  15

Gly Ile His Pro Lys Asn Ile Gln Ser Val Asn Val Lys Ser Pro Gly
                20                  25                  30

Pro His Cys Ala Gln Thr Glu Val Ile Ala Thr Leu Lys Asn Gly Arg
            35                  40                  45

Lys Ala Cys Leu Asn Pro Ala Ser Pro Ile Val Lys Lys Ile Ile Glu
        50                  55                  60

Lys Met Leu Asn Ser Asp Lys Ser Asn
65                  70

<210> SEQ ID NO 6
<211> LENGTH: 5
<212> TYPE: PRT
<213> ORGANISM: Artificial Sequence
<220> FEATURE:
<223> OTHER INFORMATION: Synthetic

<400> SEQUENCE: 6

Ser Tyr Tyr Ile Tyr
1               5

<210> SEQ ID NO 7
<211> LENGTH: 12
<212> TYPE: PRT
<213> ORGANISM: Artificial Sequence
<220> FEATURE:
<223> OTHER INFORMATION: Synthetic

<400> SEQUENCE: 7

Glu Ile Asp Pro Ser His Gly Gly Pro Thr Phe Asn
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic

<400> SEQUENCE: 8

Thr Arg Glu Ser Gly Thr Gly Ala Met Asp Tyr
1               5                   10

<210> SEQ ID NO 9
<211> LENGTH: 15
<212> TYPE: PRT
<213> ORGANISM: Artificial Sequence
<220> FEATURE:
<223> OTHER INFORMATION: Synthetic

<400> SEQUENCE: 9

Lys Ala Ser Gln Ser Val Asp Tyr Asp Gly Asp Ser Tyr Val Asn
1               5                   10                  15

<210> SEQ ID NO 10
<211> LENGTH: 7
<212> TYPE: PRT
<213> ORGANISM: Artificial Sequence
<220> FEATURE:
```

-continued

<223> OTHER INFORMATION: Synthetic

<400> SEQUENCE: 10

Ala Ala Ser Asn Leu Glu Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic

<400> SEQUENCE: 11

Gln Gln Ser Ser Glu Asp Pro Trp Thr
1               5

<210> SEQ ID NO 12
<211> LENGTH: 112
<212> TYPE: PRT
<213> ORGANISM: Artificial Sequence
<220> FEATURE:
<223> OTHER INFORMATION: Synthetic

<400> SEQUENCE: 12

Asp Ile Gln Met Thr Gln Ser Pro Ser Ser Leu Ser Ala Ser Val Gly
1               5                   10                  15

Asp Arg Ala Thr Ile Ser Cys Lys Ala Ser Gln Ser Val Asp Tyr Asp
                20                  25                  30

Gly Asp Ser Tyr Val Asn Trp Tyr Gln Gln Lys Pro Gly Lys Ala Pro
            35                  40                  45

Lys Leu Leu Ile Tyr Ala Ala Ser Asn Leu Glu Ser Gly Ile Pro Ser
        50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Ser
                85                  90                  95

Glu Asp Pro Trp Thr Phe Gly Gln Gly Thr Lys Val Glu Ile Lys Arg
            100                 105                 110

<210> SEQ ID NO 13
<211> LENGTH: 336
<212> TYPE: DNA
<213> ORGANISM: Artificial Sequence
<220> FEATURE:
<223> OTHER INFORMATION: Synthetic

<400> SEQUENCE: 13
gacatccaga tgacccagag ccccagcagc ctgagcgcca gcgtgggcga cagggccacc    60
atcagctgca aggccagcca gagcgtggac tacgacggcg acagctacgt gaactggtac   120
cagcagaagc ccggcaaggc ccccaagctg ctgatctacg ccgccagcaa cctggagagc   180
ggcatcccca gcaggttcag cggcagcggc agcggcaccg acttcaccct gaccatcagc   240
agcctgcagc ccgaggactt cgccacctac tactgccagc agagcagcga ggacccctgg   300
accttcggcc agggcaccaa ggtggagatc aagagg                              336

<210> SEQ ID NO 14
<211> LENGTH: 118
<212> TYPE: PRT
<213> ORGANISM: Artificial Sequence
<220> FEATURE:

<223> OTHER INFORMATION: Synthetic

<400> SEQUENCE: 14

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Ser Tyr
            20                  25                  30

Tyr Ile Tyr Trp Val Arg Gln Ala Pro Gly Gln Gly Leu Glu Trp Ile
        35                  40                  45

Gly Glu Ile Asp Pro Ser His Gly Gly Pro Thr Phe Asn Glu Lys Phe
    50                  55                  60

Lys Asn Arg Ala Thr Leu Thr Val Asp Lys Ser Lys Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Ser Gly Thr Gly Ala Met Asp Tyr Trp Gly Gln Gly Thr
            100                 105                 110

Leu Val Thr Val Ser Ser
        115

<210> SEQ ID NO 15
<211> LENGTH: 354
<212> TYPE: DNA
<213> ORGANISM: Artificial Sequence
<220> FEATURE:
<223> OTHER INFORMATION: Synthetic

<400> SEQUENCE: 15
caggtgcagc tggtgcagag cggcgccgag gtgaagaagc ccggcgccag cgtgaagctg     60
agctgcaagg ccagcggcta caccttcacc agctactaca tctactgggt gaggcaggcc    120
cccggccagg gcctggagtg gatcggcgag atcgacccca gccacggcgg ccccaccttc    180
aacgagaagt tcaagaacag ggccaccctg accgtggaca agagcaagag caccgcctac    240
atggagctga gcagcctgag gagcgaggac accgccgtgt actactgcac cagggagagc    300
ggcaccggcg ccatggacta ctggggccag ggcaccctgg tgaccgtgag cagc           354

<210> SEQ ID NO 16
<211> LENGTH: 250
<212> TYPE: PRT
<213> ORGANISM: Artificial Sequence
<220> FEATURE:
<223> OTHER INFORMATION: Synthetic

<400> SEQUENCE: 16

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Ser Tyr
            20                  25                  30

Tyr Ile Tyr Trp Val Arg Gln Ala Pro Gly Gln Gly Leu Glu Trp Ile
        35                  40                  45

Gly Glu Ile Asp Pro Ser His Gly Gly Pro Thr Phe Asn Glu Lys Phe
    50                  55                  60

Lys Asn Arg Ala Thr Leu Thr Val Asp Lys Ser Lys Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Ser Gly Thr Gly Ala Met Asp Tyr Trp Gly Gln Gly Thr

Leu Val Thr Val Ser Ser Gly Gly Gly Gly Ser
            100             105             110

Gly Gly Gly Ala Arg Gly Gly Gly Ser Asp Ile Gln Met Thr Gln
            115             120             125

Ser Pro Ser Ser Leu Ser Ala Ser Val Gly Asp Arg Ala Thr Ile Ser
145             150             155             160

Cys Lys Ala Ser Gln Ser Val Asp Tyr Asp Gly Asp Ser Tyr Val Asn
                165             170             175

Trp Tyr Gln Gln Lys Pro Gly Lys Ala Pro Lys Leu Leu Ile Tyr Ala
                180             185             190

Ala Ser Asn Leu Glu Ser Gly Ile Pro Ser Arg Phe Ser Gly Ser Gly
            195             200             205

Ser Gly Thr Asp Phe Thr Leu Thr Ile Ser Ser Leu Gln Pro Glu Asp
            210             215             220

Phe Ala Thr Tyr Tyr Cys Gln Gln Ser Ser Glu Asp Pro Trp Thr Phe
225             230             235             240

Gly Gln Gly Thr Lys Val Glu Ile Lys Arg
                245             250

<210> SEQ ID NO 17
<211> LENGTH: 750
<212> TYPE: DNA
<213> ORGANISM: Artificial Sequence
<220> FEATURE:
<223> OTHER INFORMATION: Synthetic

<400> SEQUENCE: 17
caggttcagc tggttcagtc tggtgcggaa gttaaaaaac cgggtgcgtc tgttaaactg      60
tcttgcaaag cgtctggtta caccttcacc tcttactaca tctactgggt tcgtcaggcg    120
ccgggtcagg gtctggaatg gatcggtgaa atcgacccgt ctcacggtgg tccgaccttc    180
aacgaaaaat tcaaaaaccg tgcgaccctg accgttgaca atctaaatc taccgcgtac    240 atggaactgt cttctctgcg ttctgaagac accgcggttt actactgcac ccgtgaatct    300
ggtaccggtg cgatggacta ctgggtcag ggtaccctgg ttaccgtttc ttctggtggt    360
ggtggttctg gcggcggcgg ctctggcgga ggtgctcgag gcggtggcgg atcggacatc    420
cagatgaccc agtctccgtc ttctctgtct cgtctgttg gtgaccgtgc gaccatctct    480
tgcaaagcgt ctcagtctgt tgactacgac ggtgactctt acgttaactg gtaccagcag    540
aaaccgggta aagcgccgaa actgctgatc tacgcgcgt ctaacctgga atctggtatc    600
ccgtctcgtt tctctggttc tggttctggt accgacttca ccctgaccat ctcttctctg    660
cagccggaag acttcgcgac ctactactgc cagcagtctt ctgaagaccc gtggaccttc    720
ggtcagggta ccaaagttga aatcaaacgt                                     750

<210> SEQ ID NO 18
<211> LENGTH: 118
<212> TYPE: PRT
<213> ORGANISM: Artificial Sequence
<220> FEATURE:
<223> OTHER INFORMATION: Synthetic

<400> SEQUENCE: 18

Gln Val Gln Leu Val Glu Ser Gly Gly Gly Leu Val Gln Pro Gly Gly
1               5                   10                  15

Ser Leu Arg Leu Ser Cys Lys Ala Ser Gly Tyr Thr Phe Thr Ser Tyr

```
            20                  25                  30
Tyr Ile Tyr Trp Val Arg Gln Ala Pro Gly Lys Gly Leu Glu Trp Ile
        35                  40                  45

Gly Glu Ile Asp Pro Ser His Gly Gly Pro Thr Phe Asn Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Glu Ser Gly Thr Gly Ala Met Asp Tyr Trp Gly Gln Gly Thr
            100                 105                 110

Leu Val Thr Val Ser Ser
        115

<210> SEQ ID NO 19
<211> LENGTH: 354
<212> TYPE: DNA
<213> ORGANISM: Artificial Sequence
<220> FEATURE:
<223> OTHER INFORMATION: Synthetic

<400> SEQUENCE: 19
caggtgcagc tggtggagag cggcggcggc ctggtgcagc ccggcggcag cctgaggctg      60
agctgcaagg ccagcggcta caccttcacc agctactaca tctactgggt gaggcaggcc     120
cccggcaagg gcctggagtg gatcggcgag atcgacccca gccacggcgg ccccaccttc     180
aacgagaagt tcaagaacag gttcaccatc agcagggaca cagcaagaa caccctgtac      240 ctgcagatga acagcctgag ggccgaggac accgccgtgt actactgcac caggagagc     300 ggcaccggcg ccatggacta ctggggccag ggcaccctgg tgaccgtgag cagc           354

<210> SEQ ID NO 20
<211> LENGTH: 250
<212> TYPE: PRT
<213> ORGANISM: Artificial Sequence
<220> FEATURE:
<223> OTHER INFORMATION: Synthetic

<400> SEQUENCE: 20

Gln Val Gln Leu Val Glu Ser Gly Gly Gly Leu Val Gln Pro Gly Gly
1               5                   10                  15

Ser Leu Arg Leu Ser Cys Lys Ala Ser Gly Tyr Thr Phe Thr Ser Tyr
            20                  25                  30

Tyr Ile Tyr Trp Val Arg Gln Ala Pro Gly Lys Gly Leu Glu Trp Ile
        35                  40                  45

Gly Glu Ile Asp Pro Ser His Gly Gly Pro Thr Phe Asn Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Glu Ser Gly Thr Gly Ala Met Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Ala Arg Gly Gly Gly Ser Asp Ile Gln Met Thr Gln
    130                 135                 140
```

```
Ser Pro Ser Ser Leu Ser Ala Ser Val Gly Asp Arg Ala Thr Ile Ser
145                 150                 155                 160

Cys Lys Ala Ser Gln Ser Val Asp Tyr Asp Gly Asp Ser Tyr Val Asn
                165                 170                 175

Trp Tyr Gln Gln Lys Pro Gly Lys Ala Pro Lys Leu Leu Ile Tyr Ala
            180                 185                 190

Ala Ser Asn Leu Glu Ser Gly Ile Pro Ser Arg Phe Ser Gly Ser Gly
        195                 200                 205

Ser Gly Thr Asp Phe Thr Leu Thr Ile Ser Ser Leu Gln Pro Glu Asp
    210                 215                 220

Phe Ala Thr Tyr Tyr Cys Gln Gln Ser Ser Glu Asp Pro Trp Thr Phe
225                 230                 235                 240

Gly Gln Gly Thr Lys Val Glu Ile Lys Arg
                245                 250

<210> SEQ ID NO 21
<211> LENGTH: 750
<212> TYPE: DNA
<213> ORGANISM: Artificial Sequence
<220> FEATURE:
<223> OTHER INFORMATION: Synthetic

<400> SEQUENCE: 21
caggtgcagc tggtggagag cggcggcggc ctggtgcagc ccggcggcag cctgaggctg      60
agctgcaagg ccagcggcta caccttcacc agctactaca tctactgggt gaggcaggcc     120
cccggcaagg gcctggagtg gatcggcgag atcgacccca gccacggcgg ccccaccttc     180
aacgagaagt tcaagaacag gttcaccatc agcagggaca cagcaagaa caccctgtac     240 ctgcagatga acagcctgag ggccgaggac accgccgtgt actactgcac cagggagagc     300
ggcaccggcg ccatggacta ctggggccag ggcaccctgg tgaccgtgag cagcggtggt     360
ggtggttctg gcggcggcgg ctctggcgga ggtgctcgag gcggtggcgg atcggacatc     420
cagatgaccc agagccccag cagcctgagc gccagcgtgg gcgacagggc caccatcagc     480
tgcaaggcca gccagagcgt ggactacgac ggcgacagct acgtgaactg gtaccagcag     540
aagcccggca aggcccccaa gctgctgatc tacgccgcca gcaacctgga gagcggcatc     600
cccagcaggt tcagcggcag cggcagcggc accgacttca ccctgaccat cagcagcctg     660
cagcccgagg acttcgccac ctactactgc cagcagagca gcgaggaccc ctggaccttc     720
ggccagggca ccaaggtgga gatcaagagg                                       750

<210> SEQ ID NO 22
<211> LENGTH: 273
<212> TYPE: PRT
<213> ORGANISM: Artificial Sequence
<220> FEATURE:
<223> OTHER INFORMATION: Synthetic

<400> SEQUENCE: 22

Gln Val Gln Leu Val Glu Ser Gly Gly Gly Leu Val Gln Pro Gly Gly
1               5                   10                  15

Ser Leu Arg Leu Ser Cys Lys Ala Ser Gly Tyr Thr Phe Thr Ser Tyr
            20                  25                  30

Tyr Ile Tyr Trp Val Arg Gln Ala Pro Gly Lys Gly Leu Glu Trp Ile
        35                  40                  45

Gly Glu Ile Asp Pro Ser His Gly Gly Pro Thr Phe Asn Glu Lys Phe
    50                  55                  60
```

Lys Asn Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Arg Glu Ser Gly Thr Gly Ala Met Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Ala Arg Gly Gly Gly Ser Asp Ile Gln Met Thr Gln
    130                 135                 140

Ser Pro Ser Ser Leu Ser Ala Ser Val Gly Asp Arg Ala Thr Ile Ser
145                 150                 155                 160

Cys Lys Ala Ser Gln Ser Val Asp Tyr Asp Gly Asp Ser Tyr Val Asn
                165                 170                 175

Trp Tyr Gln Gln Lys Pro Gly Lys Ala Pro Lys Leu Leu Ile Tyr Ala
            180                 185                 190

Ala Ser Asn Leu Glu Ser Gly Ile Pro Ser Arg Phe Ser Gly Ser Gly
        195                 200                 205

Ser Gly Thr Asp Phe Thr Leu Thr Ile Ser Ser Leu Gln Pro Glu Asp
    210                 215                 220

Phe Ala Thr Tyr Tyr Cys Gln Gln Ser Ser Glu Asp Pro Trp Thr Phe
225                 230                 235                 240

Gly Gln Gly Thr Lys Val Glu Ile Lys Arg Ala Ser Gly Ala Glu Gln
                245                 250                 255

Lys Leu Ile Ser Glu Glu Asp Leu Asn Gly Ala His His His His
            260                 265                 270

His

<210> SEQ ID NO 23
<211> LENGTH: 822
<212> TYPE: DNA
<213> ORGANISM: Artificial Sequence
<220> FEATURE:
<223> OTHER INFORMATION: Synthetic

<400> SEQUENCE: 23
caggtgcagc tggtggagag cggcggcggc ctggtgcagc ccggcggcag cctgaggctg      60
agctgcaagg ccagcggcta caccttcacc agctactaca tctactgggt gaggcaggcc     120
cccggcaagg gcctggagtg gatcggcgag atcgacccca ccacggcgg ccccaccttc     180 aacgagaagt tcaagaacag gttcaccatc agcagggaca caagcaagaa caccctgtac     240
ctgcagatga caagcctgag ggccgaggac accgccgtgt actactgcac cagggagagc     300
ggcaccggcg ccatggacta ctggggccag ggcaccctgg tgaccgtgag cagcggtggt     360
ggtggttctg gcggcggcgg ctctggcgga ggtgctcgag gcggtggcgg atcggacatc     420
cagatgaccc agagcccag cagcctgagc gccagcgtgg gcgacagggc caccatcagc     480
tgcaaggcca gccagagcgt ggactacgac ggcgacagct acgtgaactg gtaccagcag     540
aagcccggca aggcccccaa gctgctgatc tacgccgcca gcaacctgga gagcggcatc     600
cccagcaggt tcagcggcag cggcagcggc accgacttca ccctgaccat cagcagcctg     660
cagcccgagg acttcgccac ctactactgc cagcagagca gcgaggaccc ctggaccttc     720
ggccagggca ccaaggtgga gatcaagagg gctagcggtg ctgaacagaa actgatctct     780
gaagaagacc tgaacggtgc tcaccaccac caccaccact ag                         822

<210> SEQ ID NO 24
<211> LENGTH: 273
<212> TYPE: PRT
<213> ORGANISM: Artificial Sequence
<220> FEATURE:
<223> OTHER INFORMATION: Synthetic

<400> SEQUENCE: 24

```
Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Ser Tyr
            20                  25                  30

Tyr Ile Tyr Trp Val Arg Gln Ala Pro Gly Gln Gly Leu Glu Trp Ile
        35                  40                  45

Gly Glu Ile Asp Pro Ser His Gly Gly Pro Thr Phe Asn Glu Lys Phe
    50                  55                  60

Lys Asn Arg Ala Thr Leu Thr Val Asp Lys Ser Lys Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Ser Gly Thr Gly Ala Met Asp Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Ala Arg Gly Gly Gly Ser Asp Ile Gln Met Thr Gln
    130                 135                 140

Ser Pro Ser Ser Leu Ser Ala Ser Val Gly Asp Arg Ala Thr Ile Ser
145                 150                 155                 160

Cys Lys Ala Ser Gln Ser Val Asp Tyr Asp Gly Asp Ser Tyr Val Asn
                165                 170                 175

Trp Tyr Gln Gln Lys Pro Gly Lys Ala Pro Lys Leu Leu Ile Tyr Ala
            180                 185                 190

Ala Ser Asn Leu Glu Ser Gly Ile Pro Ser Arg Phe Ser Gly Ser Gly
        195                 200                 205

Ser Gly Thr Asp Phe Thr Leu Thr Ile Ser Ser Leu Gln Pro Glu Asp
    210                 215                 220

Phe Ala Thr Tyr Tyr Cys Gln Gln Ser Ser Glu Asp Pro Trp Thr Phe
225                 230                 235                 240

Gly Gln Gly Thr Lys Val Glu Ile Lys Arg Ala Ser Gly Ala Glu Gln
                245                 250                 255

Lys Leu Ile Ser Glu Glu Asp Leu Asn Gly Ala His His His His
            260                 265                 270

His
```

<210> SEQ ID NO 25
<211> LENGTH: 822
<212> TYPE: DNA
<213> ORGANISM: Artificial Sequence
<220> FEATURE:
<223> OTHER INFORMATION: Synthetic

<400> SEQUENCE: 25

```
caggttcagc tggttcagtc tggtgcggaa gttaaaaaac cgggtgcgtc tgttaaactg      60
tcttgcaaag cgtctggtta caccttcacc tcttactaca tctactgggt cgtcaggcg     120 ccgggtcagg gtctggaatg gatcggtgaa atcgacccgt ctcacggtgg tccgaccttc    180
```

```
aacgaaaaat tcaaaaaccg tgcgaccctg accgttgaca atctaaatc taccgcgtac    240 atggaactgt cttctctgcg ttctgaagac accgcggttt actactgcac ccgtgaatct    300
ggtaccggtg cgatggacta ctggggtcag ggtaccctgg ttaccgtttc ttctggtggt    360
ggtggttctg gcggcggcgg ctctggcgga ggtgctcgag gcggtggcgg atcggacatc    420
cagatgaccc agtctccgtc ttctctgtct gcgtctgttg gtgaccgtgc gaccatctct    480
tgcaaagcgt ctcagtctgt tgactacgac ggtgactctt acgttaactg gtaccagcag    540
aaaccgggta aagcgccgaa actgctgatc tacgcggcgt ctaacctgga atctggtatc    600
ccgtctcgtt tctctggttc tggttctggt accgacttca ccctgaccat ctcttctctg    660
cagccggaag acttcgcgac ctactactgc cagcagtctt ctgaagaccc gtggaccttc    720
ggtcagggta ccaaagttga aatcaaacgt gctagcggtg ctgaacagaa actgatctct    780
gaagaagacc tgaacggtgc tcaccaccac caccaccact ag                        822
```

```
<210> SEQ ID NO 26
<211> LENGTH: 20
<212> TYPE: PRT
<213> ORGANISM: Artificial Sequence
<220> FEATURE:
<223> OTHER INFORMATION: Synthetic

<400> SEQUENCE: 26

Met Asp Ser Gln Ala Gln Val Leu Met Leu Leu Leu Leu Trp Val Ser
1               5                   10                  15

Gly Thr Cys Gly
            20

<210> SEQ ID NO 27
<211> LENGTH: 19
<212> TYPE: PRT
<213> ORGANISM: Artificial Sequence
<220> FEATURE:
<223> OTHER INFORMATION: Synthetic

<400> SEQUENCE: 27

Met Glu Phe Gly Leu Ser Trp Val Phe Leu Val Ala Ile Leu Lys Gly
1               5                   10                  15

Val Gln Cys

<210> SEQ ID NO 28
<211> LENGTH: 135
<212> TYPE: PRT
<213> ORGANISM: Artificial Sequence
<220> FEATURE:
<223> OTHER INFORMATION: Synthetic

<400> SEQUENCE: 28

Met Asp Ser Gln Ala Gln Val Leu Met Leu Leu Leu Leu Trp Val Ser
1               5                   10                  15

Gly Thr Cys Gly Asp Ile Gln Met Thr Gln Ser Pro Ser Ser Leu Ser
            20                  25                  30

Ala Ser Val Gly Asp Arg Ala Thr Ile Ser Cys Lys Ala Ser Gln Ser
        35                  40                  45

Val Asp Tyr Asp Gly Asp Ser Tyr Val Asn Trp Tyr Gln Gln Lys Pro
    50                  55                  60

Gly Lys Ala Pro Lys Leu Leu Ile Tyr Ala Ala Ser Asn Leu Glu Ser
65                  70                  75                  80

Gly Ile Pro Ser Arg Phe Ser Gly Ser Gly Ser Gly Thr Asp Phe Thr
```

```
                     85                  90                  95
Leu Thr Ile Ser Ser Leu Gln Pro Glu Asp Phe Ala Thr Tyr Tyr Cys
                100                 105                 110

Gln Gln Ser Ser Glu Asp Pro Trp Thr Phe Gly Gln Gly Thr Lys Val
        115                 120                 125

Glu Ile Lys Arg Arg Thr His
    130                 135

<210> SEQ ID NO 29
<211> LENGTH: 405
<212> TYPE: DNA
<213> ORGANISM: Artificial Sequence
<220> FEATURE:
<223> OTHER INFORMATION: Synthetic

<400> SEQUENCE: 29
atggattcac aggcccaggt tcttatgtta ctgctgctat gggtatctgg tacctgtggg     60
gacatccaga tgacccagag ccccagcagc ctgagcgcca gcgtgggcga cagggccacc    120
atcagctgca aggccagcca gagcgtggac tacgacggcg acagctacgt gaactggtac    180
cagcagaagc ccggcaaggc ccccaagctg ctgatctacg ccgccagcaa cctggagagc    240
ggcatcccca gcaggttcag cggcagcggc agcggcaccg acttcaccct gaccatcagc    300
agcctgcagc ccgaggactt cgccacctac tactgccagc agagcagcga ggaccctggg    360
accttcggcc agggcaccaa ggtggagatc aagaggcgta cgcac                    405

<210> SEQ ID NO 30
<211> LENGTH: 146
<212> TYPE: PRT
<213> ORGANISM: Artificial Sequence
<220> FEATURE:
<223> OTHER INFORMATION: Synthetic

<400> SEQUENCE: 30

Val Leu Glu Phe Ala Thr Met Glu Phe Gly Leu Ser Trp Val Phe Leu
1               5                   10                  15

Val Ala Ile Leu Lys Gly Val Gln Cys Gln Val Gln Leu Val Glu Ser
            20                  25                  30

Gly Gly Gly Leu Val Gln Pro Gly Gly Ser Leu Arg Leu Ser Cys Lys
        35                  40                  45

Ala Ser Gly Tyr Thr Phe Thr Ser Tyr Tyr Ile Tyr Trp Val Arg Gln
    50                  55                  60

Ala Pro Gly Lys Gly Leu Glu Trp Ile Gly Glu Ile Asp Pro Ser His
65                  70                  75                  80

Gly Gly Pro Thr Phe Asn Glu Lys Phe Lys Asn Arg Phe Thr Ile Ser
                85                  90                  95

Arg Asp Asn Ser Lys Asn Thr Leu Tyr Leu Gln Met Asn Ser Leu Arg
                100                 105                 110

Ala Glu Asp Thr Ala Val Tyr Tyr Cys Thr Arg Glu Ser Gly Thr Gly
            115                 120                 125

Ala Met Asp Tyr Trp Gly Gln Gly Thr Leu Val Thr Val Ser Ser Gly
        130                 135                 140

Pro Tyr
145

<210> SEQ ID NO 31
<211> LENGTH: 438
<212> TYPE: DNA
```

```
<213> ORGANISM: Artificial Sequence
<220> FEATURE:
<223> OTHER INFORMATION: Synthetic

<400> SEQUENCE: 31
gtgctggaat tcgccaccat ggagtttggg ctgagctggg ttttcttgt ggctatttta    60
aaaggtgtcc agtgtcaggt gcagctggtg gagagcggcg gcggcctggt gcagcccggc   120
ggcagcctga ggctgagctg caaggccagc ggctacacct tcaccagcta ctacatctac   180
tgggtgaggc aggcccccgg caagggcctg gagtggatcg gcgagatcga ccccagccac   240
ggcggcccca ccttcaacga aagttcaag aacaggttca ccatcagcag ggacaacagc   300
aagaacaccc tgtacctgca gatgaacagc ctgagggccg aggacaccgc cgtgtactac   360
tgcaccaggg agagcggcac cggcgccatg gactactggg gccagggcac cctggtgacc   420
gtgagcagcg ggccctac                                                 438

<210> SEQ ID NO 32
<211> LENGTH: 146
<212> TYPE: PRT
<213> ORGANISM: Artificial Sequence
<220> FEATURE:
<223> OTHER INFORMATION: Synthetic

<400> SEQUENCE: 32

Val Leu Glu Phe Ala Thr Met Glu Phe Gly Leu Ser Trp Val Phe Leu
1               5                   10                  15

Val Ala Ile Leu Lys Gly Val Gln Cys Gln Val Gln Leu Val Gln Ser
            20                  25                  30

Gly Ala Glu Val Lys Lys Pro Gly Ala Ser Val Lys Leu Ser Cys Lys
        35                  40                  45

Ala Ser Gly Tyr Thr Phe Thr Ser Tyr Tyr Ile Tyr Trp Val Arg Gln
    50                  55                  60

Ala Pro Gly Gln Gly Leu Glu Trp Ile Gly Glu Ile Asp Pro Ser His
65                  70                  75                  80

Gly Gly Pro Thr Phe Asn Glu Lys Phe Lys Asn Arg Ala Thr Leu Thr
                85                  90                  95

Val Asp Lys Ser Lys Ser Thr Ala Tyr Met Glu Leu Ser Ser Leu Arg
            100                 105                 110

Ser Glu Asp Thr Ala Val Tyr Tyr Cys Thr Arg Glu Ser Gly Thr Gly
        115                 120                 125

Ala Met Asp Tyr Trp Gly Gln Gly Thr Leu Val Thr Val Ser Ser Gly
    130                 135                 140

Pro Tyr
145

<210> SEQ ID NO 33
<211> LENGTH: 438
<212> TYPE: DNA
<213> ORGANISM: Artificial Sequence
<220> FEATURE:
<223> OTHER INFORMATION: Synthetic

<400> SEQUENCE: 33
gtgctggaat tcgccaccat ggagtttggg ctgagctggg ttttcttgt ggctatttta    60
aaaggtgtcc agtgtcaggt tcagctggtt cagtctggtg cggaagttaa aaaaccgggt   120
gcgtctgtta aactgtcttg caaagcgtct ggttacacct tcacctctta ctacatctac   180
tgggttcgtc aggcgccggg tcagggtctg gaatggatcg gtgaaatcga cccgtctcac   240
```

```
ggtggtccga ccttcaacga aaaattcaaa aaccgtgcga ccctgaccgt tgacaaatct        300
aaatctaccg cgtacatgga actgtcttct ctgcgttctg aagacaccgc ggtttactac        360
tgcacccgtg aatctggtac cggtgcgatg gactactggg gtcagggtac cctggttacc        420
gtttcttctg ggccctac                                                      438
```

```
<210> SEQ ID NO 34
<211> LENGTH: 136
<212> TYPE: PRT
<213> ORGANISM: Artificial Sequence
<220> FEATURE:
<223> OTHER INFORMATION: Synthetic

<400> SEQUENCE: 34
```

```
Ala Thr Met Asp Ser Gln Ala Gln Val Leu Met Leu Leu Leu Leu Trp
1               5                   10                  15

Val Ser Gly Thr Cys Gly Asp Ile Gln Met Thr Gln Ser Pro Ser Ser
            20                  25                  30

Leu Ser Ala Ser Val Gly Asp Arg Ala Thr Ile Ser Cys Lys Ala Ser
        35                  40                  45

Gln Ser Val Asp Tyr Asp Gly Asp Ser Tyr Val Asn Trp Tyr Gln Gln
    50                  55                  60

Lys Pro Gly Lys Ala Pro Lys Leu Leu Ile Tyr Ala Ala Ser Asn Leu
65                  70                  75                  80

Glu Ser Gly Ile Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Ser Ser Glu Asp Pro Trp Thr Phe Gly Gln Gly Thr
        115                 120                 125

Lys Val Glu Ile Lys Arg Arg Thr
    130                 135
```

```
<210> SEQ ID NO 35
<211> LENGTH: 408
<212> TYPE: DNA
<213> ORGANISM: Artificial Sequence
<220> FEATURE:
<223> OTHER INFORMATION: Synthetic

<400> SEQUENCE: 35
```

```
gccaccatgg attcacaggc ccaggttctt atgttactgc tgctatgggt atctggtacc         60
tgtggggaca tccagatgac ccagagcccc agcagcctga gcgccagcgt gggcgacagg        120
gccaccatca gctgcaaggc cagccagagc gtggactacg acggcgacag ctacgtgaac        180
tggtaccagc agaagcccgg caaggccccc aagctgctga tctacgccgc cagcaacctg        240
gagagcggca tccccagcag gttcagcggc agcggcagcg gcaccgactt caccctgacc        300
atcagcagcc tgcagcccga ggacttcgcc acctactact gccagcagag cagcgaggac        360
ccctggacct tcggccaggg caccaaggtg gagatcaaga ggcgtacg                     408
```

```
<210> SEQ ID NO 36
<211> LENGTH: 279
<212> TYPE: PRT
<213> ORGANISM: Artificial Sequence
<220> FEATURE:
<223> OTHER INFORMATION: Synthetic

<400> SEQUENCE: 36
```

Gly Tyr Phe Lys Gly Val Gln Cys Gln Val Gln Leu Val Glu Ser Gly
1               5                   10                  15

Gly Gly Leu Val Gln Pro Gly Gly Ser Leu Arg Leu Ser Cys Lys Ala
            20                  25                  30

Ser Gly Tyr Thr Phe Thr Ser Tyr Tyr Ile Tyr Trp Val Arg Gln Ala
            35                  40                  45

Pro Gly Lys Gly Leu Glu Trp Ile Gly Glu Ile Asp Pro Ser His Gly
        50                  55                  60

Gly Pro Thr Phe Asn Glu Lys Phe Lys Asn Arg Phe Thr Ile Ser Arg
65              70                  75                  80

Asp Asn Ser Lys Asn Thr Leu Tyr Leu Gln Met Asn Ser Leu Arg Ala
                85                  90                  95

Glu Asp Thr Ala Val Tyr Tyr Cys Thr Arg Glu Ser Gly Thr Gly Ala
            100                 105                 110

Met Asp Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
            165                 170                 175

His Thr Phe Pro Ala Val Leu Gln Ser Ser Gly Leu Tyr Ser Leu Phe
        180                 185                 190

Ser Val Val Thr Val Pro Ser Asn Asn Leu Gly Thr His Thr Tyr Ile
            195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Thr
225                 230                 235                 240

Pro Glu Leu Leu Gly Asp Arg His Ser Ser Ser Pro Gln Asn Pro
            245                 250                 255

Arg Asp Thr Leu Met Ile Ser Arg Thr Pro Glu Val Thr Gly Leu Val
            260                 265                 270

Val Asp Met Lys His Glu Asp
        275

<210> SEQ ID NO 37
<211> LENGTH: 837
<212> TYPE: DNA
<213> ORGANISM: Artificial Sequence
<220> FEATURE:
<223> OTHER INFORMATION: Synthetic

<400> SEQUENCE: 37
ggctatttta aaggtgtcca gtgtcaggtg cagctggtgg agagcggcgg cggcctggtg    60
cagcccggcg gcagcctgag gctgagctgc aaggccagcg gctacacctt caccagctac   120
tacatctact gggtgaggca ggccccccggc aagggcctgg agtggatcgg cgagatcgac   180
cccagccacg gcggccccac cttcaacgag aagttcaaga acaggttcac catcagcagg   240
gacaacagca agaacaccct gtacctgcag atgaacagcc tgagggccga ggacaccgcc   300
gtgtactact gcaccaggga gagcggcacc ggcgccatgg actactgggg ccagggcacc   360
ctggtgaccg tgagcagcgc cagcacgaag ggcccatcgg tcttccccct ggcaccctcc   420

```
tccaagagca cctctggggg cacagcggcc ctgggctgcc tggtcaagga ctacttcccc    480
gaaccggtga cggtgtcgtg gaactcaggc gccctgacca gcggcgtgca caccttcccg    540
gctgtcctac agtcctcagg actctactcc ctcttcagcg tggtgaccgt gccctccaac    600
aacttgggca cccacaccta catctgcaac gtgaatcaca agcccagcaa caccaaggtg    660
gacaagaaag ttgagcccaa atcttgtgac aaaactcaca catgcccacc gtgcccaaca    720
cctgaactcc tggggaccg tcactcttcc tcttcccccc aaaacccaag agacaccctc     780
atgatctccc ggaccctga ggtcacaggc ctggtggtgg acatgaagca cgaagac       837
```

```
<210> SEQ ID NO 38
<211> LENGTH: 186
<212> TYPE: PRT
<213> ORGANISM: Artificial Sequence
<220> FEATURE:
<223> OTHER INFORMATION: Synthetic

<400> SEQUENCE: 38

Gly Tyr Phe Lys Gly Val Gln Cys Gln Val Gln Leu Val Gln Ser Gly
1               5                   10                  15

Ala Glu Val Lys Lys Pro Gly Ala Ser Val Lys Leu Ser Cys Lys Ala
            20                  25                  30

Ser Gly Tyr Thr Phe Thr Ser Tyr Tyr Ile Tyr Trp Val Arg Gln Ala
        35                  40                  45

Pro Gly Gln Gly Leu Glu Trp Ile Gly Glu Ile Asp Pro Ser His Gly
    50                  55                  60

Gly Pro Thr Phe Asn Glu Lys Phe Lys Asn Arg Ala Thr Leu Thr Val
65                  70                  75                  80

Asp Lys Ser Lys Ser Thr Ala Tyr Met Glu Leu Ser Ser Leu Arg Ser
                85                  90                  95

Glu Asp Thr Ala Val Tyr Tyr Cys Thr Arg Glu Ser Gly Thr Gly Ala
            100                 105                 110

Met Asp Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Met
                165                 170                 175

His Thr Phe Pro Ser Val Leu Arg Ser Ser
            180                 185
```

```
<210> SEQ ID NO 39
<211> LENGTH: 558
<212> TYPE: DNA
<213> ORGANISM: Artificial Sequence
<220> FEATURE:
<223> OTHER INFORMATION: Synthetic

<400> SEQUENCE: 39
ggctatttta aggtgtcca gtgtcaggtt cagctggttc agtctggtgc ggaagttaaa     60
aaaccgggtg cgtctgttaa actgtcttgc aaagcgtctg gttacacctt cacctcttac    120
tacatctact gggttcgtca ggcgccgggt cagggtctgg aatggatcgg tgaaatcgac    180
ccgtctcacg gtggtccgac cttcaacgaa aaattcaaaa accgtgcgac cctgaccgtt    240
gacaaatcta aatctaccgc gtacatggaa ctgtcttctc tgcgttctga agacaccgcg    300
```

```
gtttactact gcacccgtga atctggtacc ggtgcgatgg actactgggg tcagggtacc      360
ctggttaccg tttcttctgc cagcacgaag ggcccatcgg tcttcccct ggcaccctcc      420 tccaagagca cctctggggg cacagcggcc ctgggctgcc tggtcaagga ctacttcccc     480
gaaccggtga cggtgtcgtg gaactcaggc gccctgacca gcggcatgca caccttcccg     540
tctgtcctac ggtcctct                                                   558
```